US011864849B2

(12) United States Patent
Chin et al.

(10) Patent No.: US 11,864,849 B2
(45) Date of Patent: Jan. 9, 2024

(54) SYSTEMS AND INSTRUMENTS FOR SUCTION AND IRRIGATION

(71) Applicant: Auris Health, Inc., Redwood City, CA (US)

(72) Inventors: Erica Ding Chin, Redwood City, CA (US); Spencer James Witte, Los Altos, CA (US); Barry Nichols Gardiner, Orinda, CA (US)

(73) Assignee: Auris Health, Inc., Redwood City, CA (US)

( * ) Notice: Subject to any disclaimer, the term of this patent is extended or adjusted under 35 U.S.C. 154(b) by 116 days.

(21) Appl. No.: 16/546,129

(22) Filed: Aug. 20, 2019

(65) Prior Publication Data

US 2020/0093549 A1    Mar. 26, 2020

Related U.S. Application Data

(60) Provisional application No. 62/736,746, filed on Sep. 26, 2018.

(51) Int. Cl.
*A61B 10/04* (2006.01)
*A61B 17/29* (2006.01)
(Continued)

(52) U.S. Cl.
CPC .......... *A61B 34/30* (2016.02); *A61B 1/00149* (2013.01); *A61B 1/2676* (2013.01);
(Continued)

(58) Field of Classification Search
CPC ............ A61B 17/28; A61B 2017/2926; A61B 2017/293; A61B 2034/301;
(Continued)

(56) References Cited

U.S. PATENT DOCUMENTS

| 3,763,860 A | 10/1973 | Clarke |
| 4,040,413 A | 8/1977 | Ohshiro |

(Continued)

FOREIGN PATENT DOCUMENTS

| CN | 101443069 | 5/2009 |
| CN | 100515347 | 7/2009 |

(Continued)

OTHER PUBLICATIONS

International search report and written opinion dated Oct. 17, 2019 for PCT/US2019/047342.

*Primary Examiner* — Martin T Ton
(74) *Attorney, Agent, or Firm* — Frost Brown Todd LLP

(57) ABSTRACT

Provided is a robotic system that includes a surgical instrument with a wrist including an elongate shaft extending between a proximal end and a distal end, a wrist extending from the distal end of the elongate shaft, and an end effector extending from the wrist. The end effector may include a first jaw and a second jaw, the first and second jaw being moveable between an open position in which ends of the jaws are separated from each other, and a closed position in which the ends of the jaws are closer to each other as compared to the open position. The surgical instrument may also include a tube extending through the elongate shaft and the wrist, the tube having an outlet in fluid communication with a passage formed by an interior of the first and second jaws when the jaws are in the closed position.

19 Claims, 40 Drawing Sheets

(51) Int. Cl.
    *A61B 34/30*   (2016.01)
    *A61B 1/267*   (2006.01)
    *A61B 34/20*   (2016.01)
    *A61B 1/307*   (2006.01)
    *A61B 17/22*   (2006.01)
    *A61B 18/26*   (2006.01)
    *A61B 1/00*    (2006.01)
    *A61B 17/34*   (2006.01)
    *A61B 50/13*   (2016.01)
    *A61B 18/00*   (2006.01)
    *A61B 6/03*    (2006.01)

(52) U.S. Cl.
    CPC .............. *A61B 1/307* (2013.01); *A61B 10/04* (2013.01); *A61B 17/2202* (2013.01); *A61B 17/2909* (2013.01); *A61B 17/3423* (2013.01); *A61B 18/26* (2013.01); *A61B 34/20* (2016.02); *A61B 50/13* (2016.02); *A61B 6/032* (2013.01); *A61B 2010/045* (2013.01); *A61B 2017/2947* (2013.01); *A61B 2018/00511* (2013.01); *A61B 2034/2051* (2016.02); *A61B 2034/301* (2016.02); *A61B 2034/305* (2016.02); *A61B 2217/005* (2013.01); *A61B 2217/007* (2013.01)

(58) Field of Classification Search
    CPC ........ A61B 2034/305; A61B 2034/306; A61B 2017/2933; A61B 2017/2934; A61B 2017/2936; A61B 2017/2939; A61B 2017/2941; A61B 2017/2947
    See application file for complete search history.

(56) References Cited

U.S. PATENT DOCUMENTS

| | | |
|---|---|---|
| 4,198,960 A | 4/1980 | Utsugi |
| 4,470,407 A | 9/1984 | Hussein |
| 4,532,935 A | 8/1985 | Wang et al. |
| 4,685,458 A | 8/1987 | Leckrone |
| 4,747,405 A | 5/1988 | Leckrone |
| 4,854,301 A | 8/1989 | Nakajima |
| 4,898,574 A | 2/1990 | Uchiyama et al. |
| 4,983,165 A | 1/1991 | Loiterman |
| 5,029,574 A | 7/1991 | Shimamura et al. |
| 5,085,659 A | 2/1992 | Rydell |
| 5,196,023 A | 3/1993 | Martin |
| 5,217,465 A | 6/1993 | Steppe |
| 5,308,323 A | 5/1994 | Sogawa et al. |
| 5,318,589 A | 6/1994 | Lichtman |
| 5,325,848 A | 7/1994 | Adams et al. |
| 5,342,381 A | 8/1994 | Tidemand |
| 5,344,395 A | 9/1994 | Whalen et al. |
| 5,353,783 A | 10/1994 | Nakao et al. |
| 5,370,609 A | 12/1994 | Drasler et al. |
| 5,372,124 A | 12/1994 | Takayama et al. |
| 5,411,016 A | 5/1995 | Kume |
| 5,431,649 A | 7/1995 | Mulier et al. |
| 5,441,485 A | 8/1995 | Peters |
| 5,449,356 A | 9/1995 | Walbrink |
| 5,450,843 A | 9/1995 | Moll et al. |
| 5,472,426 A | 12/1995 | Bonati et al. |
| 5,496,267 A | 3/1996 | Drasler |
| 5,501,667 A | 3/1996 | Verduin, Jr. |
| 5,520,684 A | 5/1996 | Imran |
| 5,545,170 A | 8/1996 | Hart |
| 5,562,239 A | 10/1996 | Boiarski et al. |
| 5,562,648 A | 10/1996 | Peterson |
| 5,562,678 A | 10/1996 | Booker |
| 5,572,999 A | 11/1996 | Funda et al. |
| 5,573,535 A | 11/1996 | Viklund |
| 5,603,724 A * | 2/1997 | O'Connor ........... A61B 17/1608 606/174 |
| 5,613,973 A | 3/1997 | Jackson et al. |
| 5,645,083 A | 7/1997 | Essig et al. |
| 5,653,374 A | 8/1997 | Young et al. |
| 5,658,311 A | 8/1997 | Baden |
| 5,695,500 A | 12/1997 | Taylor et al. |
| 5,697,949 A | 12/1997 | Giurtino et al. |
| 5,710,870 A | 1/1998 | Ohm |
| 5,716,325 A | 2/1998 | Bonutti |
| 5,788,667 A | 8/1998 | Stoller |
| 5,792,165 A | 8/1998 | Klieman |
| 5,797,900 A | 8/1998 | Madhani |
| 5,810,770 A | 9/1998 | Chin et al. |
| 5,893,869 A | 4/1999 | Barnhart |
| 5,897,491 A | 4/1999 | Kastenbauer et al. |
| 5,924,175 A | 7/1999 | Lippitt |
| 5,989,230 A | 11/1999 | Frassica |
| 6,071,281 A | 6/2000 | Burnside et al. |
| 6,093,157 A | 7/2000 | Chandrasekaran |
| 6,110,171 A | 8/2000 | Rydell |
| 6,120,476 A | 9/2000 | Fung et al. |
| 6,120,498 A | 9/2000 | Jani et al. |
| 6,156,030 A | 12/2000 | Neev |
| 6,174,318 B1 | 1/2001 | Bates et al. |
| 6,206,903 B1 | 3/2001 | Ramans |
| 6,183,435 B1 | 6/2001 | Bumbalough et al. |
| 6,322,557 B1 | 11/2001 | Nikolaevich |
| 6,375,635 B1 | 4/2002 | Moutafis |
| 6,394,998 B1 | 5/2002 | Wallace et al. |
| 6,405,078 B1 | 6/2002 | Moaddeb et al. |
| 6,436,117 B1 * | 8/2002 | Waller ........... A61B 17/320016 606/167 |
| 6,440,061 B1 | 8/2002 | Wenner et al. |
| 6,508,823 B1 | 1/2003 | Gonon |
| 6,522,906 B1 | 2/2003 | Salisbury et al. |
| 6,577,891 B1 | 6/2003 | Jaross et al. |
| 6,676,668 B2 | 1/2004 | Mercereau et al. |
| 6,685,698 B2 | 2/2004 | Morley et al. |
| 6,706,050 B1 | 3/2004 | Giannadakis |
| 7,282,055 B2 | 10/2007 | Tsuruta |
| 7,559,934 B2 | 7/2009 | Teague et al. |
| 7,736,356 B2 | 6/2010 | Cooper et al. |
| 7,963,911 B2 | 6/2011 | Turliuc |
| 7,987,046 B1 | 7/2011 | Peterman |
| 8,002,713 B2 | 8/2011 | Heske |
| 8,038,598 B2 | 10/2011 | Khachi |
| 8,092,397 B2 | 1/2012 | Wallace et al. |
| 8,187,173 B2 | 5/2012 | Miyoshi |
| 8,257,303 B2 | 9/2012 | Moll et al. |
| 8,480,595 B2 | 7/2013 | Speeg |
| 8,523,762 B2 | 9/2013 | Miyamoto et al. |
| 8,540,748 B2 | 9/2013 | Murphy et al. |
| 8,820,603 B2 | 9/2014 | Shelton et al. |
| 8,882,660 B2 | 11/2014 | Phee et al. |
| 8,945,163 B2 | 2/2015 | Voegele et al. |
| 8,956,280 B2 | 2/2015 | Eversull et al. |
| 9,345,456 B2 | 5/2016 | Tsonton et al. |
| 9,460,536 B2 | 10/2016 | Hasegawa et al. |
| 9,504,604 B2 | 11/2016 | Alvarez |
| 9,561,083 B2 | 2/2017 | Yu et al. |
| 9,592,042 B2 | 3/2017 | Titus |
| 9,597,152 B2 | 3/2017 | Schaeffer |
| 9,622,827 B2 | 4/2017 | Yu et al. |
| 9,636,184 B2 | 5/2017 | Lee et al. |
| 9,713,509 B2 | 7/2017 | Schuh et al. |
| 9,727,963 B2 | 8/2017 | Mintz et al. |
| 9,730,757 B2 | 8/2017 | Brudniok |
| 9,737,371 B2 | 8/2017 | Romo et al. |
| 9,737,373 B2 | 8/2017 | Schuh |
| 9,744,335 B2 | 8/2017 | Jiang |
| 9,763,741 B2 | 9/2017 | Alvarez et al. |
| 9,788,910 B2 | 10/2017 | Schuh |
| 9,844,412 B2 | 12/2017 | Bogusky et al. |
| 9,867,635 B2 | 1/2018 | Alvarez et al. |
| 9,918,681 B2 | 3/2018 | Wallace et al. |
| 9,931,025 B1 | 4/2018 | Graetzel et al. |
| 9,949,749 B2 | 4/2018 | Noonan et al. |
| 9,955,986 B2 | 5/2018 | Shah |
| 9,962,228 B2 | 5/2018 | Schuh et al. |
| 9,980,785 B2 | 5/2018 | Schuh |
| 9,993,313 B2 | 6/2018 | Schuh et al. |

(56) References Cited

U.S. PATENT DOCUMENTS

| | | |
|---|---|---|
| 10,016,900 B1 | 7/2018 | Meyer et al. |
| 10,022,192 B1 | 7/2018 | Ummalaneni |
| 10,080,576 B2 | 9/2018 | Romo et al. |
| 10,136,959 B2 | 11/2018 | Mintz et al. |
| 10,145,747 B1 | 12/2018 | Lin et al. |
| 10,149,720 B2 | 12/2018 | Romo |
| 10,159,532 B1 | 12/2018 | Ummalaneni et al. |
| 10,159,533 B2 | 12/2018 | Moll et al. |
| 10,169,875 B2 | 1/2019 | Mintz et al. |
| 10,219,874 B2 | 3/2019 | Yu et al. |
| 10,231,793 B2 | 3/2019 | Romo |
| 10,231,867 B2 | 3/2019 | Alvarez et al. |
| 10,244,926 B2 | 4/2019 | Noonan et al. |
| 10,285,574 B2 | 5/2019 | Landey et al. |
| 10,299,870 B2 | 5/2019 | Connolly et al. |
| 10,314,463 B2 | 6/2019 | Agrawal et al. |
| 10,350,390 B2 | 7/2019 | Moll et al. |
| 10,383,765 B2 | 8/2019 | Alvarez et al. |
| 10,398,518 B2 | 9/2019 | Yu et al. |
| 10,405,939 B2 | 9/2019 | Romo et al. |
| 10,405,940 B2 | 9/2019 | Romo |
| 10,426,559 B2 | 10/2019 | Graetzel et al. |
| 10,426,661 B2 | 10/2019 | Kintz |
| 10,434,660 B2 | 10/2019 | Meyer |
| 10,464,209 B2 | 11/2019 | Ho et al. |
| 10,470,830 B2 | 11/2019 | Hill |
| 10,482,599 B2 | 11/2019 | Mintz et al. |
| 10,493,241 B2 | 12/2019 | Jiang |
| 10,500,001 B2 | 12/2019 | Yu et al. |
| 10,517,692 B2 | 12/2019 | Eyre et al. |
| 10,524,866 B2 | 1/2020 | Srinivasan |
| 10,639,114 B2 | 5/2020 | Schuh |
| 10,667,875 B2 | 6/2020 | DeFonzo |
| 10,751,140 B2 | 8/2020 | Wallace et al. |
| 10,765,487 B2 | 9/2020 | Ho |
| 2002/0019644 A1 | 2/2002 | Hastings |
| 2002/0111608 A1 | 8/2002 | Baerveldt |
| 2002/0111621 A1 | 8/2002 | Wallace et al. |
| 2003/0004455 A1 | 1/2003 | Kadziauskas |
| 2003/0040681 A1 | 2/2003 | Ng et al. |
| 2003/0065358 A1 | 4/2003 | Frecker |
| 2003/0109877 A1 | 6/2003 | Morley |
| 2003/0109889 A1 | 6/2003 | Mercereau |
| 2003/0158545 A1 | 8/2003 | Hovda et al. |
| 2003/0208189 A1 | 11/2003 | Payman |
| 2004/0068291 A1* | 4/2004 | Suzuki ............... A61B 10/0096 606/205 |
| 2004/0143253 A1 | 7/2004 | Vanney |
| 2004/0153093 A1 | 8/2004 | Donovan |
| 2004/0158261 A1 | 8/2004 | Vu |
| 2004/0186349 A1 | 9/2004 | Ewers |
| 2004/0193146 A1 | 9/2004 | Lee et al. |
| 2004/0210116 A1 | 10/2004 | Nakao |
| 2004/0253079 A1 | 12/2004 | Sanchez |
| 2005/0033270 A1 | 2/2005 | Ramans et al. |
| 2005/0054900 A1 | 3/2005 | Mawn |
| 2005/0159645 A1 | 7/2005 | Bertolero |
| 2005/0240178 A1 | 10/2005 | Morley et al. |
| 2005/0261705 A1 | 11/2005 | Gist |
| 2006/0015133 A1 | 1/2006 | Grayzel |
| 2006/0058813 A1 | 3/2006 | Teague |
| 2006/0116693 A1 | 6/2006 | Weisenburgh |
| 2006/0135963 A1 | 6/2006 | Kick |
| 2006/0156875 A1 | 7/2006 | McRury et al. |
| 2006/0189891 A1 | 8/2006 | Waxman et al. |
| 2007/0016164 A1 | 1/2007 | Dudney et al. |
| 2007/0027443 A1 | 2/2007 | Rose |
| 2007/0027534 A1 | 2/2007 | Bergheim |
| 2007/0032906 A1 | 2/2007 | Sutherland et al. |
| 2007/0106304 A1 | 5/2007 | Hammack |
| 2007/0135803 A1 | 6/2007 | Belson |
| 2007/0208375 A1 | 9/2007 | Nishizawa |
| 2007/0213668 A1 | 9/2007 | Spitz |
| 2007/0239178 A1 | 10/2007 | Weitzner et al. |
| 2007/0250111 A1 | 10/2007 | Lu |
| 2007/0299427 A1 | 12/2007 | Yeung et al. |
| 2008/0015566 A1 | 1/2008 | Livneh |
| 2008/0021440 A1 | 1/2008 | Solomon |
| 2008/0033467 A1 | 2/2008 | Miyamoto et al. |
| 2008/0046122 A1 | 2/2008 | Manzo et al. |
| 2008/0065111 A1 | 3/2008 | Blumenkranz |
| 2008/0125698 A1 | 5/2008 | Greg et al. |
| 2008/0187101 A1 | 8/2008 | Gertner |
| 2008/0196533 A1 | 8/2008 | Bergamasco |
| 2008/0228104 A1 | 9/2008 | Uber et al. |
| 2009/0012507 A1 | 1/2009 | Culbertson et al. |
| 2009/0036900 A1 | 2/2009 | Moll |
| 2009/0043305 A1 | 2/2009 | Brodbeck |
| 2009/0082634 A1 | 3/2009 | Kathrani et al. |
| 2009/0088774 A1 | 4/2009 | Swarup et al. |
| 2009/0105723 A1 | 4/2009 | Dillinger |
| 2009/0131885 A1 | 5/2009 | Akahoshi |
| 2009/0161827 A1 | 6/2009 | Gertner et al. |
| 2009/0227998 A1 | 9/2009 | Aljuri |
| 2009/0248041 A1 | 10/2009 | Williams et al. |
| 2009/0248043 A1 | 10/2009 | Tierney et al. |
| 2009/0264878 A1 | 10/2009 | Carmel et al. |
| 2009/0270760 A1 | 10/2009 | Leimbach et al. |
| 2009/0287188 A1 | 11/2009 | Golden et al. |
| 2009/0299352 A1 | 12/2009 | Zerfas |
| 2009/0312773 A1 | 12/2009 | Cabrera et al. |
| 2010/0004642 A1 | 1/2010 | Lumpkin |
| 2010/0010504 A1 | 1/2010 | Simaan et al. |
| 2010/0011900 A1 | 1/2010 | Burbank |
| 2010/0011901 A1 | 1/2010 | Burbank |
| 2010/0016852 A1 | 1/2010 | Manzo et al. |
| 2010/0082017 A1 | 4/2010 | Zickler |
| 2010/0179632 A1 | 7/2010 | Bruszewski et al. |
| 2010/0204605 A1 | 8/2010 | Blakley |
| 2010/0204646 A1 | 8/2010 | Plicchi et al. |
| 2010/0217235 A1 | 8/2010 | Thorstenson |
| 2010/0225209 A1 | 9/2010 | Goldberg |
| 2010/0228249 A1 | 9/2010 | Mohr |
| 2010/0268211 A1 | 10/2010 | Manwaring et al. |
| 2010/0312141 A1 | 12/2010 | Keast et al. |
| 2010/0331858 A1 | 12/2010 | Simaan et al. |
| 2011/0015483 A1 | 1/2011 | Barbagli |
| 2011/0071541 A1 | 3/2011 | Prisco et al. |
| 2011/0071543 A1 | 3/2011 | Prisco et al. |
| 2011/0106146 A1 | 5/2011 | Jeong |
| 2011/0125165 A1 | 5/2011 | Simaan et al. |
| 2011/0152880 A1 | 6/2011 | Alvarez et al. |
| 2011/0160713 A1 | 6/2011 | Neuberger |
| 2011/0167611 A1 | 7/2011 | Williams |
| 2011/0213362 A1 | 9/2011 | Cunningham |
| 2011/0224660 A1 | 9/2011 | Neuberger et al. |
| 2011/0237975 A1* | 9/2011 | Secrest ............... A61B 10/04 600/565 |
| 2011/0238064 A1 | 9/2011 | Williams et al. |
| 2011/0257641 A1 | 10/2011 | Hastings et al. |
| 2011/0276085 A1 | 11/2011 | Krzyzanowski |
| 2011/0313343 A1 | 12/2011 | Milutinovic et al. |
| 2012/0069167 A1 | 3/2012 | Liu et al. |
| 2012/0253277 A1 | 4/2012 | Tah et al. |
| 2012/0138586 A1 | 6/2012 | Webster et al. |
| 2012/0138660 A1 | 6/2012 | Shelton, IV et al. |
| 2012/0209315 A1 | 8/2012 | Amat |
| 2012/0232342 A1 | 9/2012 | Reydel |
| 2012/0253332 A1 | 10/2012 | Moll |
| 2012/0259320 A1 | 10/2012 | Loesel et al. |
| 2012/0296318 A1 | 11/2012 | Wellhofer et al. |
| 2013/0006144 A1 | 1/2013 | Clancy |
| 2013/0035537 A1 | 2/2013 | Wallace et al. |
| 2013/0053877 A1 | 2/2013 | BenMaamer |
| 2013/0066136 A1 | 3/2013 | Palese et al. |
| 2013/0085442 A1 | 4/2013 | Shtul et al. |
| 2013/0085486 A1 | 4/2013 | Boutoussov et al. |
| 2013/0096422 A1 | 4/2013 | Boctor |
| 2013/0096574 A1 | 4/2013 | Kang et al. |
| 2013/0110042 A1 | 5/2013 | Humphreys |
| 2013/0110107 A1 | 5/2013 | Smith et al. |
| 2013/0116716 A1* | 5/2013 | Bahls ............... A61B 17/3203 606/167 |

(56) References Cited

U.S. PATENT DOCUMENTS

| | | | |
|---|---|---|---|
| 2013/0144274 A1* | 6/2013 | Stefanchik | A61B 34/71 606/1 |
| 2013/0144395 A1 | 6/2013 | Stefanchik | |
| 2013/0190796 A1 | 7/2013 | Tilson et al. | |
| 2013/0225997 A1 | 8/2013 | Dillard et al. | |
| 2013/0226161 A1 | 8/2013 | Hickenbotham | |
| 2013/0233908 A1 | 9/2013 | Knodel | |
| 2013/0253267 A1 | 9/2013 | Collins | |
| 2013/0303876 A1 | 11/2013 | Gelfand et al. | |
| 2013/0310819 A1 | 11/2013 | Neuberger et al. | |
| 2013/0334281 A1 | 12/2013 | Williams | |
| 2013/0345686 A1 | 12/2013 | Brown | |
| 2014/0005681 A1 | 1/2014 | Gee et al. | |
| 2014/0039681 A1 | 2/2014 | Bowling | |
| 2014/0046308 A1 | 2/2014 | Bischoff | |
| 2014/0051985 A1 | 2/2014 | Fan et al. | |
| 2014/0058365 A1 | 2/2014 | Bille | |
| 2014/0058404 A1 | 2/2014 | Hammack | |
| 2014/0058428 A1 | 2/2014 | Christopher | |
| 2014/0100445 A1 | 4/2014 | Stenzel | |
| 2014/0142591 A1 | 5/2014 | Alvarez et al. | |
| 2014/0163318 A1 | 6/2014 | Swanstrom | |
| 2014/0194859 A1 | 7/2014 | Ianchulev | |
| 2014/0194905 A1 | 7/2014 | Kappel | |
| 2014/0243849 A1 | 8/2014 | Saglam | |
| 2014/0246473 A1 | 9/2014 | Auld | |
| 2014/0275956 A1 | 9/2014 | Fan | |
| 2014/0276723 A1 | 9/2014 | Parihar | |
| 2014/0276956 A1 | 9/2014 | Crainich | |
| 2014/0309655 A1 | 10/2014 | Gal et al. | |
| 2014/0316203 A1 | 10/2014 | Carroux et al. | |
| 2014/0357984 A1 | 12/2014 | Wallace et al. | |
| 2014/0364870 A1 | 12/2014 | Alvarez et al. | |
| 2015/0080879 A1 | 3/2015 | Trees | |
| 2015/0112335 A1* | 4/2015 | Boudreaux | A61B 18/14 606/49 |
| 2015/0127045 A1 | 5/2015 | Prestel | |
| 2015/0133960 A1 | 5/2015 | Lohmeier | |
| 2015/0164522 A1 | 6/2015 | Budiman | |
| 2015/0201917 A1 | 7/2015 | Snow | |
| 2015/0202085 A1 | 7/2015 | Lemonis | |
| 2015/0314110 A1 | 11/2015 | Park | |
| 2016/0001038 A1 | 1/2016 | Romo et al. | |
| 2016/0022289 A1 | 1/2016 | Wan | |
| 2016/0022466 A1 | 1/2016 | Pedtke | |
| 2016/0030073 A1 | 2/2016 | Lsakov | |
| 2016/0045208 A1 | 2/2016 | Ciulla | |
| 2016/0051318 A1 | 2/2016 | Manzo et al. | |
| 2016/0066935 A1 | 3/2016 | Nguyen et al. | |
| 2016/0158490 A1 | 6/2016 | Leeflang | |
| 2016/0183841 A1 | 6/2016 | Duindam et al. | |
| 2016/0199984 A1 | 7/2016 | Lohmeier et al. | |
| 2016/0228202 A1* | 8/2016 | Prindiville | A61B 34/30 |
| 2016/0235495 A1 | 8/2016 | Wallace et al. | |
| 2016/0249932 A1 | 9/2016 | Rogers et al. | |
| 2016/0270865 A1 | 9/2016 | Landey et al. | |
| 2016/0287279 A1 | 10/2016 | Bovay et al. | |
| 2016/0303743 A1 | 10/2016 | Rockrohr | |
| 2016/0310146 A1 | 10/2016 | Levy et al. | |
| 2016/0331358 A1 | 11/2016 | Gordon | |
| 2016/0367324 A1 | 12/2016 | Sato et al. | |
| 2017/0007337 A1 | 1/2017 | Dan | |
| 2017/0049471 A1 | 2/2017 | Gaffney et al. | |
| 2017/0055995 A1 | 3/2017 | Weier | |
| 2017/0065227 A1 | 3/2017 | Marrs | |
| 2017/0095234 A1 | 4/2017 | Prisco et al. | |
| 2017/0095295 A1 | 4/2017 | Overmyer | |
| 2017/0105789 A1* | 4/2017 | Boudreaux | A61B 18/1445 |
| 2017/0119481 A1 | 5/2017 | Romo et al. | |
| 2017/0135706 A1 | 5/2017 | Frey | |
| 2017/0151416 A1 | 6/2017 | Kutikov | |
| 2017/0165011 A1 | 6/2017 | Bovay et al. | |
| 2017/0172553 A1 | 6/2017 | Chaplin | |
| 2017/0172673 A1 | 6/2017 | Yu et al. | |
| 2017/0202627 A1 | 7/2017 | Sramek et al. | |
| 2017/0209073 A1 | 7/2017 | Sramek et al. | |
| 2017/0252096 A1* | 9/2017 | Felder | A61B 18/1445 |
| 2017/0265923 A1 | 9/2017 | Privitera | |
| 2017/0265954 A1 | 9/2017 | Burbank | |
| 2017/0290631 A1 | 10/2017 | Lee et al. | |
| 2017/0319289 A1 | 11/2017 | Neff et al. | |
| 2017/0333679 A1 | 11/2017 | Jiang | |
| 2017/0340396 A1 | 11/2017 | Romo et al. | |
| 2017/0367782 A1 | 12/2017 | Schuh et al. | |
| 2018/0000563 A1 | 1/2018 | Shanjani et al. | |
| 2018/0025666 A1 | 1/2018 | Ho et al. | |
| 2018/0049824 A1 | 2/2018 | Harris | |
| 2018/0177556 A1 | 6/2018 | Noonan et al. | |
| 2018/0193049 A1 | 7/2018 | Heck et al. | |
| 2018/0214011 A1 | 8/2018 | Graetzel et al. | |
| 2018/0221038 A1 | 8/2018 | Noonan et al. | |
| 2018/0221039 A1 | 8/2018 | Shah | |
| 2018/0250083 A1 | 9/2018 | Schuh et al. | |
| 2018/0271616 A1 | 9/2018 | Schuh et al. | |
| 2018/0279852 A1 | 10/2018 | Rafii-Tari et al. | |
| 2018/0280660 A1 | 10/2018 | Landey et al. | |
| 2018/0289431 A1 | 10/2018 | Draper et al. | |
| 2018/0296285 A1 | 10/2018 | Simi et al. | |
| 2018/0325499 A1 | 11/2018 | Landey et al. | |
| 2018/0333044 A1 | 11/2018 | Jenkins | |
| 2018/0360435 A1 | 12/2018 | Romo | |
| 2019/0000559 A1 | 1/2019 | Berman et al. | |
| 2019/0000560 A1 | 1/2019 | Berman et al. | |
| 2019/0000576 A1 | 1/2019 | Mintz et al. | |
| 2019/0083183 A1 | 3/2019 | Moll et al. | |
| 2019/0099231 A1 | 4/2019 | Bruehwiler | |
| 2019/0105776 A1 | 4/2019 | Ho et al. | |
| 2019/0107454 A1 | 4/2019 | Lin | |
| 2019/0110839 A1 | 4/2019 | Rafii-Tari et al. | |
| 2019/0110843 A1 | 4/2019 | Ummalaneni et al. | |
| 2019/0151148 A1 | 4/2019 | Alvarez et al. | |
| 2019/0167366 A1 | 6/2019 | Ummalaneni | |
| 2019/0175009 A1 | 6/2019 | Mintz | |
| 2019/0175062 A1 | 6/2019 | Rafii-Tari et al. | |
| 2019/0175287 A1 | 6/2019 | Hill | |
| 2019/0175799 A1 | 6/2019 | Hsu | |
| 2019/0183585 A1 | 6/2019 | Rafii-Tari et al. | |
| 2019/0183587 A1 | 6/2019 | Rafii-Tari et al. | |
| 2019/0216548 A1 | 7/2019 | Ummalaneni | |
| 2019/0216550 A1 | 7/2019 | Eyre | |
| 2019/0216576 A1 | 7/2019 | Eyre | |
| 2019/0223974 A1 | 7/2019 | Romo | |
| 2019/0228525 A1 | 7/2019 | Mintz et al. | |
| 2019/0228528 A1 | 7/2019 | Mintz et al. | |
| 2019/0246882 A1 | 8/2019 | Graetzel et al. | |
| 2019/0262086 A1 | 8/2019 | Connolly et al. | |
| 2019/0269468 A1 | 9/2019 | Hsu et al. | |
| 2019/0274764 A1 | 9/2019 | Romo | |
| 2019/0290109 A1 | 9/2019 | Agrawal et al. | |
| 2019/0298160 A1 | 10/2019 | Ummalaneni et al. | |
| 2019/0298458 A1 | 10/2019 | Srinivasan | |
| 2019/0298460 A1 | 10/2019 | Al-Jadda | |
| 2019/0298465 A1 | 10/2019 | Chin | |
| 2019/0314616 A1 | 10/2019 | Moll et al. | |
| 2019/0328213 A1 | 10/2019 | Landey et al. | |
| 2019/0336238 A1 | 11/2019 | Yu | |
| 2019/0365209 A1 | 12/2019 | Ye et al. | |
| 2019/0365479 A1 | 12/2019 | Rafii-Tari | |
| 2019/0365486 A1 | 12/2019 | Srinivasan et al. | |
| 2019/0375383 A1 | 12/2019 | Alvarez | |
| 2019/0380787 A1 | 12/2019 | Ye | |
| 2019/0380797 A1 | 12/2019 | Yu | |
| 2020/0000533 A1 | 1/2020 | Schuh | |
| 2020/0022767 A1 | 1/2020 | Hill | |
| 2020/0039086 A1 | 2/2020 | Meyer | |
| 2020/0046434 A1 | 2/2020 | Graetzel | |
| 2020/0054408 A1 | 2/2020 | Schuh et al. | |
| 2020/0060516 A1 | 2/2020 | Baez | |
| 2020/0093554 A1 | 3/2020 | Schuh | |
| 2020/0100845 A1 | 4/2020 | Julian | |
| 2020/0100855 A1 | 4/2020 | Leparmentier | |
| 2020/0101264 A1 | 4/2020 | Jiang | |
| 2020/0107894 A1 | 4/2020 | Wallace | |
| 2020/0121502 A1 | 4/2020 | Kintz | |

(56) References Cited

U.S. PATENT DOCUMENTS

| | | |
|---|---|---|
| 2020/0146769 A1 | 5/2020 | Eyre |
| 2020/0163726 A1 | 5/2020 | Tanner |
| 2020/0188043 A1 | 6/2020 | Yu |
| 2020/0197112 A1 | 6/2020 | Chin |
| 2020/0206472 A1 | 7/2020 | Ma |
| 2020/0217733 A1 | 7/2020 | Lin |
| 2020/0222134 A1 | 7/2020 | Schuh |
| 2020/0237458 A1 | 7/2020 | DeFonzo |
| 2020/0261172 A1 | 8/2020 | Romo |
| 2020/0268459 A1 | 8/2020 | Noonan et al. |
| 2020/0268460 A1 | 8/2020 | Tse |
| 2021/0022818 A1* | 1/2021 | Tsuji ................. B25J 9/106 |

FOREIGN PATENT DOCUMENTS

| | | |
|---|---|---|
| CN | 103298414 | 9/2013 |
| CN | 203953712 U | 11/2014 |
| CN | 205729413 | 11/2016 |
| EP | 1 321 106 | 6/2003 |
| EP | 1 849 423 | 10/2007 |
| JP | 2005-270464 | 10/2005 |
| WO | WO 11/161218 | 12/2011 |
| WO | WO 13/107468 | 7/2013 |
| WO | WO 13/130895 | 9/2013 |
| WO | WO 17/114855 | 7/2017 |
| WO | WO 18/069679 | 4/2018 |
| WO | WO 18/189722 | 10/2018 |

* cited by examiner

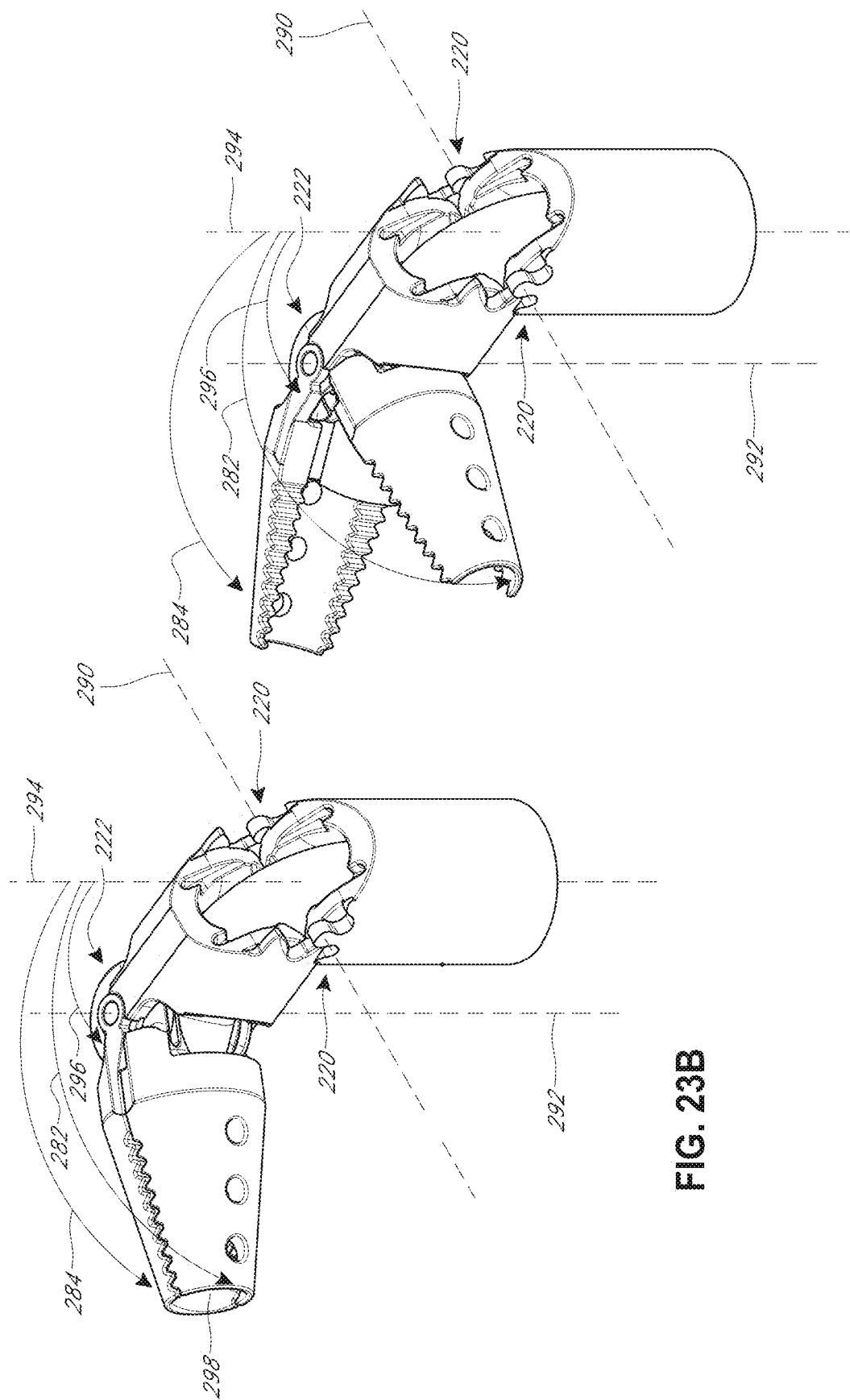

SYSTEMS AND INSTRUMENTS FOR SUCTION AND IRRIGATION

CROSS-REFERENCE TO RELATED APPLICATION(S)

This application claims the benefit of U.S. Provisional Application No. 62/736,746, filed Sep. 26, 2018, which is hereby incorporated by reference in its entirety.

TECHNICAL FIELD

The systems and methods disclosed herein are directed to a medical instrument, and in particular, to medical instrument capable of multiple functions.

BACKGROUND

Medical procedures, such as laparoscopy, may involve accessing and visualizing an internal region of a patient. In a laparoscopic procedure, a medical instrument can be inserted into the internal region through a laparoscopic access port.

In certain procedures, a robotically-enabled medical system may be used to control the insertion and/or manipulation of the medical instrument and end effector. The robotically-enabled medical system may include a robotic arm or any other instrument positioning device. The robotically-enabled medical system may also include a controller used to control the positioning of the instrument during the procedure.

SUMMARY

In a first aspect, a multi-functional surgical instrument comprises an elongate shaft extending between a proximal end and a distal end, a wrist extending from the distal end of the elongate shaft, and an end effector extending from the wrist, and a tube extending through the elongate shaft and the wrist, the tube having an outlet in fluid communication with a passage formed by an interior of the first and second jaws when the jaws are in the closed position. The end effector comprises a first jaw and a second jaw, the first and second jaw being moveable between an open position in which ends of the jaws are separated from each other and a closed position in which the ends of the jaws are closer to each other as compared to the open position.

The surgical instrument may further include one or more of the following features in any combination: (a) wherein the tube extends at least partially between the first and second jaws; (b) wherein a portion of the tube extending between the first and second jaws is a flexible tube; (c) wherein the flexible tube is between 4 and 6 millimeters in length; (d) wherein the tube is in communication with an irrigation and fluid source; (e) wherein the wrist comprises a distal clevis that comprises curved surfaces to support at least one pivot axis; (f) further comprising a first pivot pin that is pivotably supported within the first cup shaped opening and a second pivot pin that is pivotably supported within the second cup shaped opening; (g) wherein at least one pivot pin structure couples the first jaw to the second jaw; (h) wherein the wrist comprises a proximal clevis and a distal clevis; (i) wherein the distal clevis forms in part a first joint about which the first and second jaw can rotate and the proximal clevis forms a second joint about which the wrist can pivot with respect to the elongate shaft;(j) wherein the first joint is a different type of joint from the second joint; (k) wherein the second joint comprises a rolling joint and the first joint comprises a pin joint; (l) wherein the elongated shaft comprises a handle including one or more inputs, wherein at least one of the inputs enables robotic control of irrigation and/or suction capabilities of the tube; and/or (m) wherein the at least one input is coupled to a capstan capable of pinching one or both of an irrigation line and a suction line.

In another aspect, a surgical instrument comprises an elongate shaft extending between a proximal end and a distal end; a wrist extending from the distal end of the elongate shaft, the wrist comprising a distal clevis and a proximal clevis, the distal clevis comprising a distal recess; and an end effector extending from the wrist. The end effector comprising a first jaw and a second jaw, and at least one pin joint formed between the first jaw and the second jaw, wherein the at least one pin joint is supported by the distal recess.

The surgical instrument may further include one or more of the following features in any combination: (a) wherein the at least one pin joint is formed by a first pin that extends from the first jaw into an opening in the second jaw; (b) wherein the distal recess is formed by an upper surface of the wrist; (c) wherein the distal recess is cup-shaped; (d) wherein a rolling joint is formed between the proximal clevis and the distal clevis; (e) wherein the rolling comprises a cycloid joint; (f) further comprising an elongate tube extending through the elongate shaft and the wrist, the tube having an outlet in fluid communication with a passage formed by the first and second members; and/or (g) wherein the tube is flexible.

In another aspect, a method of using a multi-functional medical instrument, the method comprises (i) inserting a distal end of the medical instrument into a patient, (ii) using the medical instrument to grip tissue within the patient, and (iii) using the medical instrument to perform a suction or irrigation procedure within the patient.

The method may further include one or more of the following features in any combination: (a) using the first instrument to grip tissue within the patient and the second instrument to grip tissue within the patient; (b) using the first instrument to grip tissue adjacent to a surgical site and the second instrument to grip tissue at the surgical site; (c) maneuvering the second instrument to grip tissue adjacent to the surgical site and maneuvering the first instrument to perform a suction or irrigation procedure at the surgical site; (d) wherein the first instrument remains docked to the first cannula and the second instrument remains docked to the second cannula.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

FIG. 23B illustrates a perspective view of the surgical instrument of FIGS. 22A-C, showing rotation of two jaw halves about a yaw axis and rotation of a surgical effector about a pitch axis.

FIG. 23C illustrates a perspective view of the surgical instrument of FIGS. 22A-C, showing another rotation of two jaw halves about a yaw axis and rotation of a surgical effector about a pitch axis.

DETAILED DESCRIPTION

1. Overview.

Aspects of the present disclosure may be integrated into a robotically-enabled medical system capable of performing a variety of medical procedures, including both minimally invasive, such as laparoscopy, and non-invasive, such as endoscopy, procedures. Among endoscopic procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System—Cart.

Figure 1:
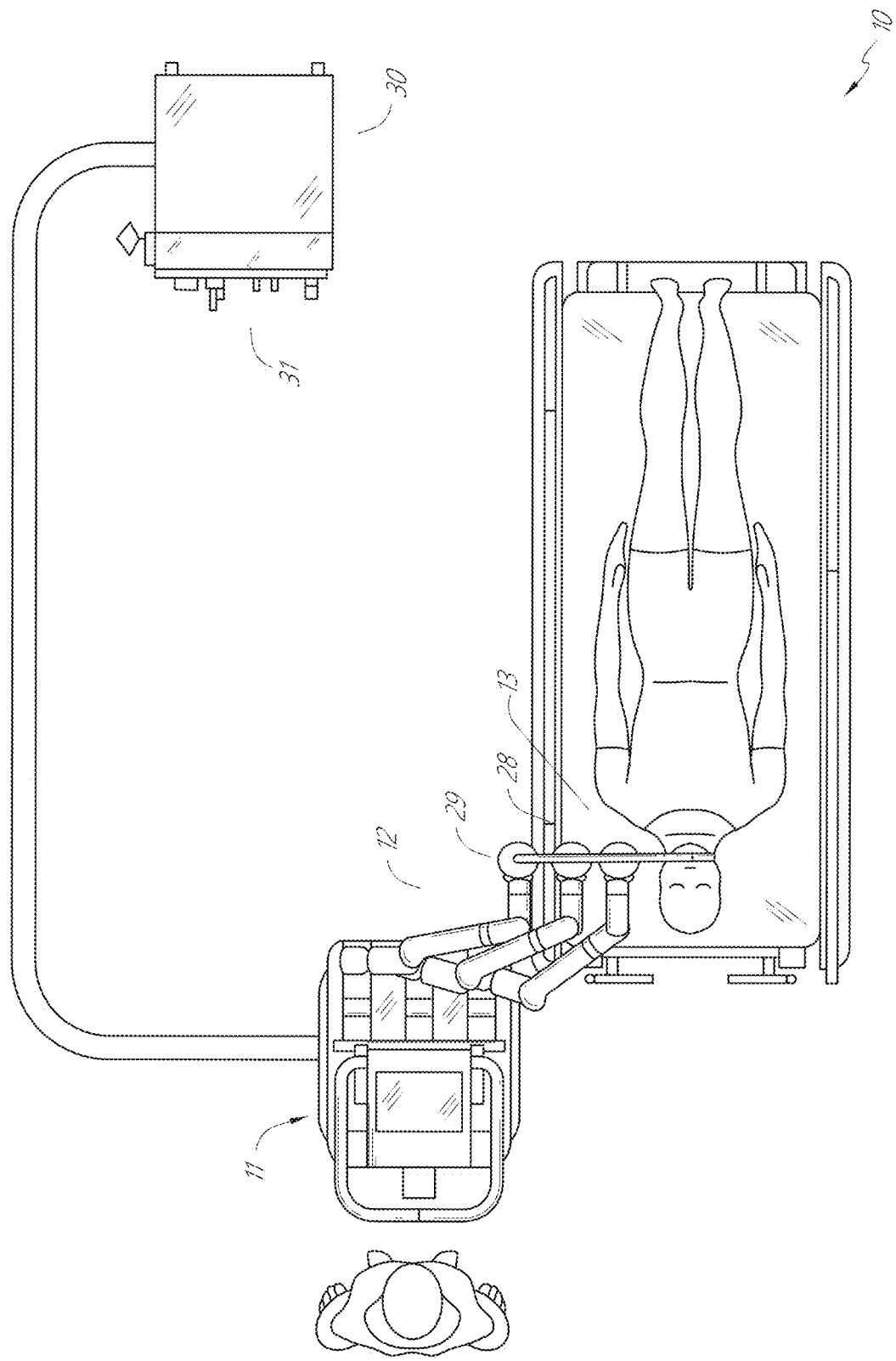
FIG. 1 illustrates an embodiment of a cart-based robotic system arranged for diagnostic and/or therapeutic bronchoscopy.
Figure 2:
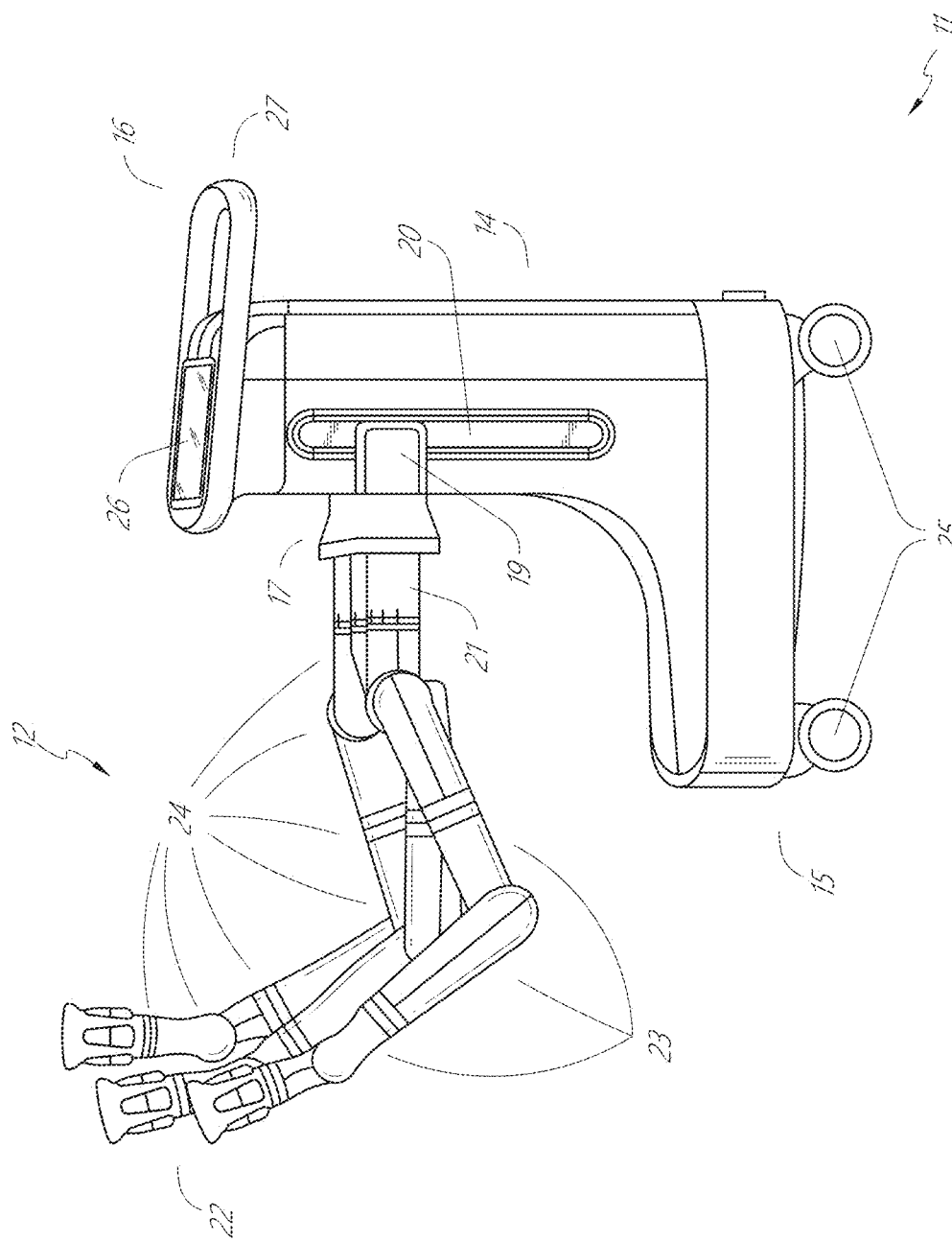
FIG. 2 depicts further aspects of the robotic system of FIG. 1.

The robotically-enabled medical system may be configured in a variety of ways depending on the particular procedure. FIG. 1 illustrates an embodiment of a cart-based robotically-enabled system 10 arranged for a diagnostic and/or therapeutic bronchoscopy. During a bronchoscopy, the system 10 may comprise a cart 11 having one or more robotic arms 12 to deliver a medical instrument, such as a steerable endoscope 13, which may be a procedure-specific bronchoscope for bronchoscopy, to a natural orifice access point (i.e., the mouth of the patient positioned on a table in the present example) to deliver diagnostic and/or therapeutic tools. As shown, the cart 11 may be positioned proximate to the patient's upper torso in order to provide access to the access point. Similarly, the robotic arms 12 may be actuated to position the bronchoscope relative to the access point. The arrangement in FIG. 1 may also be utilized when performing a gastro-intestinal (GI) procedure with a gastroscope, a specialized endoscope for GI procedures. FIG. 2 depicts an example embodiment of the cart in greater detail.

With continued reference to FIG. 1, once the cart 11 is properly positioned, the robotic arms 12 may insert the steerable endoscope 13 into the patient robotically, manually, or a combination thereof. As shown, the steerable endoscope 13 may comprise at least two telescoping parts, such as an inner leader portion and an outer sheath portion, each portion coupled to a separate instrument driver from the set of instrument drivers 28, each instrument driver coupled to the distal end of an individual robotic arm. This linear arrangement of the instrument drivers 28, which facilitates coaxially aligning the leader portion with the sheath portion, creates a "virtual rail" 29 that may be repositioned in space by manipulating the one or more robotic arms 12 into different angles and/or positions. The virtual rails described herein are depicted in the Figures using dashed lines, and accordingly the dashed lines do not depict any physical structure of the system. Translation of the instrument drivers 28 along the virtual rail 29 telescopes the inner leader portion relative to the outer sheath portion or advances or retracts the endoscope 13 from the patient. The angle of the virtual rail 29 may be adjusted, translated, and pivoted based on clinical application or physician preference. For example, in bronchoscopy, the angle and position of the virtual rail 29 as shown represents a compromise between providing physician access to the endoscope 13 while minimizing friction that results from bending the endoscope 13 into the patient's mouth.

The endoscope 13 may be directed down the patient's trachea and lungs after insertion using precise commands from the robotic system until reaching the target destination or operative site. In order to enhance navigation through the patient's lung network and/or reach the desired target, the endoscope 13 may be manipulated to telescopically extend the inner leader portion from the outer sheath portion to obtain enhanced articulation and greater bend radius. The use of separate instrument drivers 28 also allows the leader portion and sheath portion to be driven independently of each other.

For example, the endoscope 13 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 13 may endoscopically deliver tools to resect the potentially cancerous tissue. In some instances, diagnostic and therapeutic treatments can be delivered in separate procedures. In those circumstances, the endoscope 13 may also be used to deliver a fiducial to "mark" the location of the target nodule as well. In other instances, diagnostic and therapeutic treatments may be delivered during the same procedure.

The system 10 may also include a movable tower 30, which may be connected via support cables to the cart 11 to provide support for controls, electronics, fluidics, optics, sensors, and/or power to the cart 11. Placing such functionality in the tower 30 allows for a smaller form factor cart 11 that may be more easily adjusted and/or re-positioned by an operating physician and his/her staff. Additionally, the division of functionality between the cart/table and the support tower 30 reduces operating room clutter and facilitates improving clinical workflow. While the cart 11 may be positioned close to the patient, the tower 30 may be stowed in a remote location to stay out of the way during a procedure.

In support of the robotic systems described above, the tower 30 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 30 or the cart 11, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower 30 may also include a pump, flow meter, valve control, and/or fluid access in order to provide controlled irrigation and aspiration capabilities to the system that may be deployed through the endoscope 13. These components may also be controlled using the computer system of the tower 30. In some embodiments, irrigation and aspiration capabilities may be delivered directly to the endoscope 13 through separate cable(s).

The tower 30 may include a voltage and surge protector designed to provide filtered and protected electrical power to the cart 11, thereby avoiding placement of a power transformer and other auxiliary power components in the cart 11, resulting in a smaller, more moveable cart 11.

The tower 30 may also include support equipment for the sensors deployed throughout the robotic system 10. For example, the tower 30 may include optoelectronics equipment for detecting, receiving, and processing data received from the optical sensors or cameras throughout the robotic system 10. In combination with the control system, such optoelectronics equipment may be used to generate real-time images for display in any number of consoles deployed throughout the system, including in the tower 30. Similarly, the tower 30 may also include an electronic subsystem for receiving and processing signals received from deployed electromagnetic (EM) sensors. The tower 30 may also be used to house and position an EM field generator for detection by EM sensors in or on the medical instrument.

The tower 30 may also include a console 31 in addition to other consoles available in the rest of the system, e.g., console mounted on top of the cart. The console 31 may include a user interface and a display screen, such as a touchscreen, for the physician operator. Consoles in the system 10 are generally designed to provide both robotic controls as well as pre-operative and real-time information of the procedure, such as navigational and localization information of the endoscope 13. When the console 31 is not the only console available to the physician, it may be used by a second operator, such as a nurse, to monitor the health or vitals of the patient and the operation of the system 10, as well as to provide procedure-specific data, such as navigational and localization information. In other embodiments, the console 30 is housed in a body that is separate from the tower 30.

The tower 30 may be coupled to the cart 11 and endoscope 13 through one or more cables or connections (not shown). In some embodiments, the support functionality from the tower 30 may be provided through a single cable to the cart 11, simplifying and de-cluttering the operating room. In other embodiments, specific functionality may be coupled in separate cabling and connections. For example, while power may be provided through a single power cable to the cart 11, the support for controls, optics, fluidics, and/or navigation may be provided through a separate cable.

FIG. 2 provides a detailed illustration of an embodiment of the cart 11 from the cart-based robotically-enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage 17 at various vertical heights relative to the cart base 15. Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of the robotic arms 12 to be angled in a variety of configurations.

In some embodiments, the slot 20 may be supplemented with slot covers that are flush and parallel to the slot surface to prevent dirt and fluid ingress into the internal chambers of the column 14 and the vertical translation interface as the carriage 17 vertically translates. The slot covers may be deployed through pairs of spring spools positioned near the vertical top and bottom of the slot 20. The covers are coiled within the spools until deployed to extend and retract from their coiled state as the carriage 17 vertically translates up and down. The spring-loading of the spools provides force to retract the cover into a spool when the carriage 17 translates towards the spool, while also maintaining a tight seal when the carriage 17 translates away from the spool. The covers may be connected to the carriage 17 using, for example, brackets in the carriage interface 19 to ensure proper extension and retraction of the cover as the carriage 17 translates.

The column 14 may internally comprise mechanisms, such as gears and motors, that are designed to use a vertically aligned lead screw to translate the carriage 17 in a mechanized fashion in response to control signals generated in response to user inputs, e.g., inputs from the console 16.

The robotic arms 12 may generally comprise robotic arm bases 21 and end effectors 22, separated by a series of linkages 23 that are connected by a series of joints 24, each joint comprising an independent actuator, each actuator comprising an independently controllable motor. Each independently controllable joint represents an independent degree of freedom available to the robotic arm 12. Each of the robotic arms 12 may have seven joints, and thus provide seven degrees of freedom. A multitude of joints result in a multitude of degrees of freedom, allowing for "redundant" degrees of freedom. Having redundant degrees of freedom allows the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and robotic arms 12 over the floor. Accordingly, the cart base 15 houses heavier components, such as electronics, motors, power supply, as well as components that either enable movement and/or immobilize the cart 11. For example, the cart base 15 includes rollable wheel-shaped casters 25 that allow for the cart 11 to easily move around the room prior to a procedure. After reaching the appropriate position, the casters 25 may be immobilized using wheel locks to hold the cart 11 in place during the procedure.

Positioned at the vertical end of the column 14, the console 16 allows for both a user interface for receiving user input and a display screen (or a dual-purpose device such as, for example, a touchscreen 26) to provide the physician user with both pre-operative and intra-operative data. Potential pre-operative data on the touchscreen 26 may include pre-operative plans, navigation and mapping data derived from pre-operative computerized tomography (CT) scans, and/or notes from pre-operative patient interviews. Intra-operative data on display may include optical information provided from the tool, sensor and coordinate information from sensors, as well as vital patient statistics, such as respiration, heart rate, and/or pulse. The console 16 may be positioned and tilted to allow a physician to access the console from the side of the column 14 opposite the carriage 17. From this position, the physician may view the console 16, robotic arms 12, and patient while operating the console 16 from behind the cart 11. As shown, the console 16 also includes a handle 27 to assist with maneuvering and stabilizing the cart 11.

Figure 3:
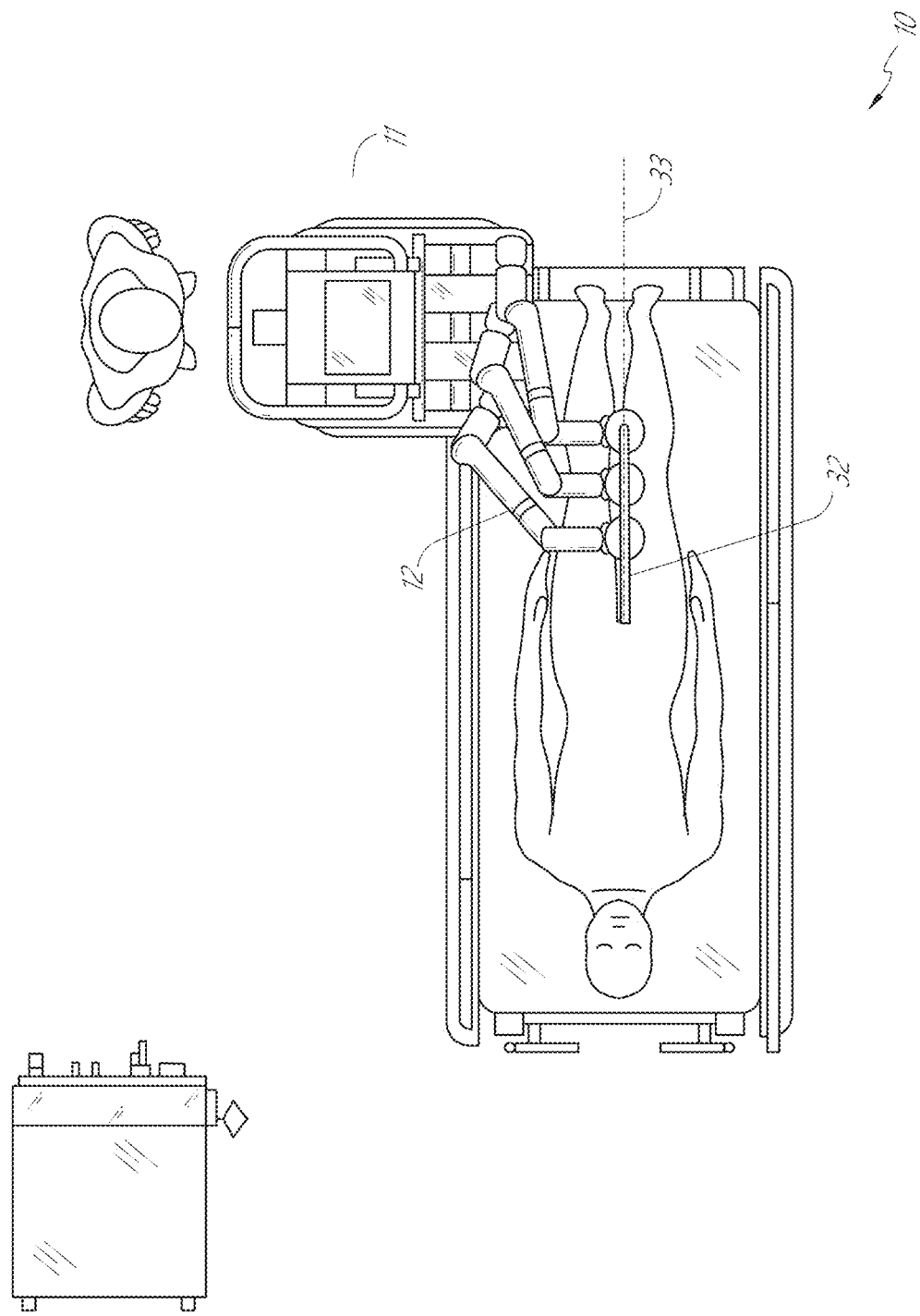
FIG. 3 illustrates an embodiment of the robotic system of FIG. 1 arranged for ureteroscopy.

FIG. 3 illustrates an embodiment of a robotically-enabled system 10 arranged for ureteroscopy. In a ureteroscopic procedure, the cart 11 may be positioned to deliver a ureteroscope 32, a procedure-specific endoscope designed to traverse a patient's urethra and ureter, to the lower abdominal area of the patient. In a ureteroscopy, it may be desirable for the ureteroscope 32 to be directly aligned with the patient's urethra to reduce friction and forces on the sensitive anatomy in the area. As shown, the cart 11 may be aligned at the foot of the table to allow the robotic arms 12 to position the ureteroscope 32 for direct linear access to the patient's urethra. From the foot of the table, the robotic arms 12 may insert the ureteroscope 32 along the virtual rail 33 directly into the patient's lower abdomen through the urethra.

After insertion into the urethra, using similar control techniques as in bronchoscopy, the ureteroscope 32 may be navigated into the bladder, ureters, and/or kidneys for diagnostic and/or therapeutic applications. For example, the ureteroscope 32 may be directed into the ureter and kidneys to break up kidney stone build up using a laser or ultrasonic lithotripsy device deployed down the working channel of the ureteroscope 32. After lithotripsy is complete, the resulting stone fragments may be removed using baskets deployed down the ureteroscope 32.

Figure 4:
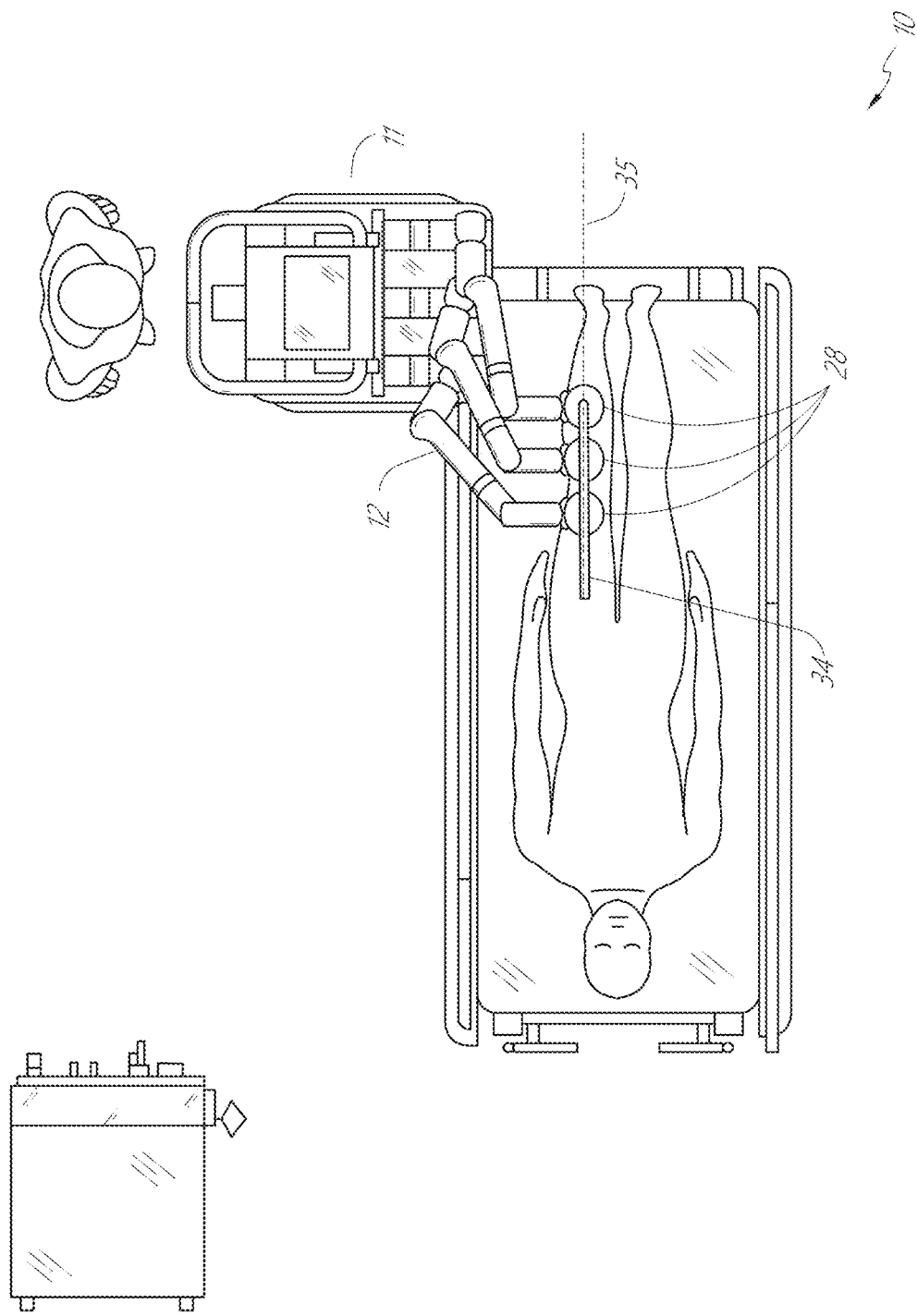
FIG. 4 illustrates an embodiment of the robotic system of FIG. 1 arranged for a vascular procedure.

FIG. 4 illustrates an embodiment of a robotically-enabled system similarly arranged for a vascular procedure. In a vascular procedure, the system 10 may be configured such that the cart 11 may deliver a medical instrument 34, such as a steerable catheter, to an access point in the femoral artery in the patient's leg. The femoral artery presents both a larger diameter for navigation as well as a relatively less circuitous and tortuous path to the patient's heart, which simplifies navigation. As in a ureteroscopic procedure, the cart 11 may be positioned towards the patient's legs and lower abdomen to allow the robotic arms 12 to provide a virtual rail 35 with direct linear access to the femoral artery access point in the patient's thigh/hip region. After insertion into the artery, the medical instrument 34 may be directed and inserted by translating the instrument drivers 28. Alternatively, the cart may be positioned around the patient's upper abdomen in order to reach alternative vascular access points, such as, for example, the carotid and brachial arteries near the shoulder and wrist.

B. Robotic System—Table.

Figure 5:
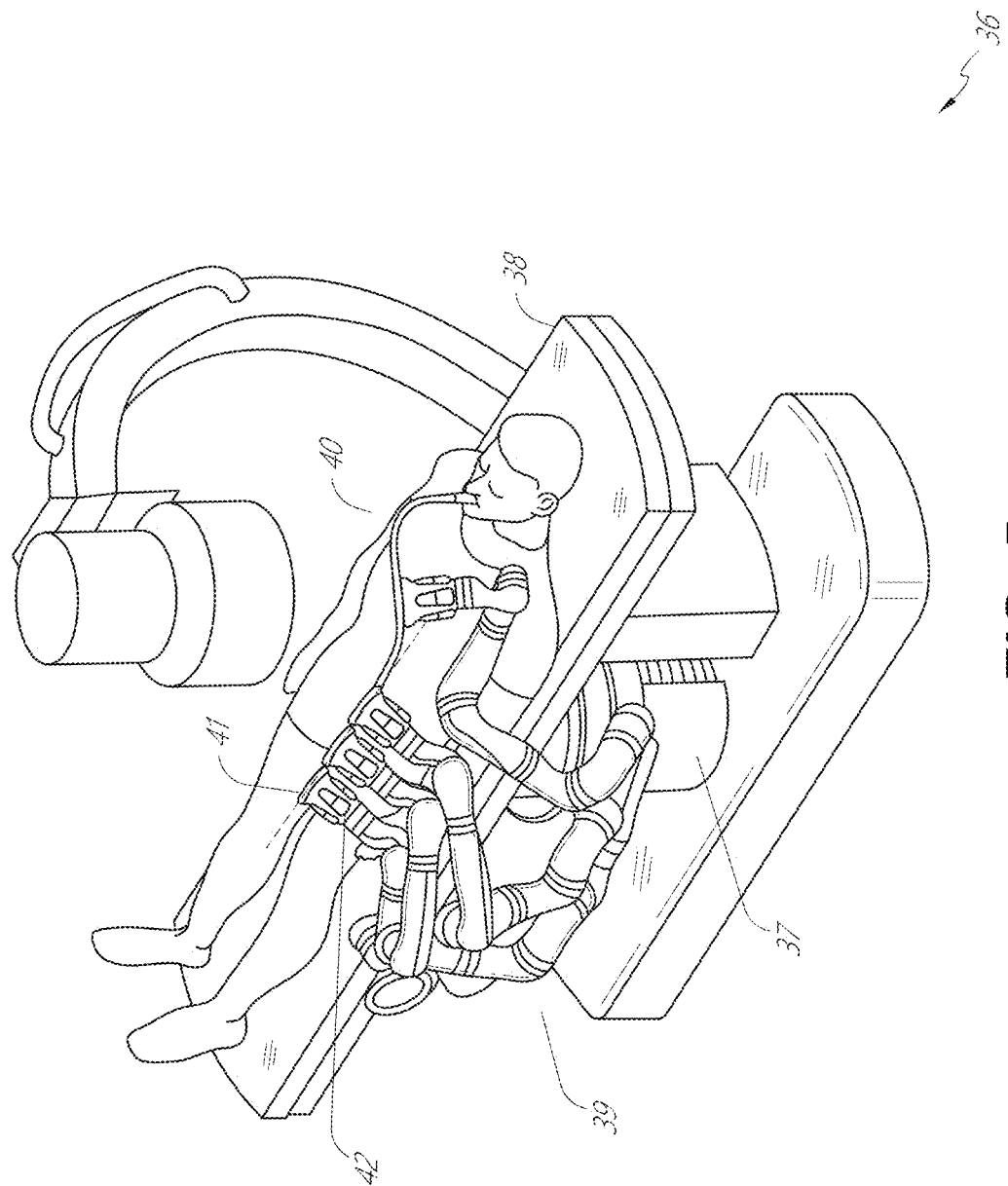
FIG. 5 illustrates an embodiment of a table-based robotic system arranged for a bronchoscopic procedure.

Embodiments of the robotically-enabled medical system may also incorporate the patient's table. Incorporation of the table reduces the amount of capital equipment within the operating room by removing the cart, which allows greater access to the patient. FIG. 5 illustrates an embodiment of such a robotically-enabled system arranged for a bronchoscopic. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipulate an elongated medical instrument, such as a bronchoscope 40 in FIG. 5, through or along a virtual rail 41 formed from the linear alignment of the instrument drivers 42. In practice, a C-arm for providing fluoroscopic imaging may be positioned over the patient's upper abdominal area by placing the emitter and detector around the table 38.

Figure 6:
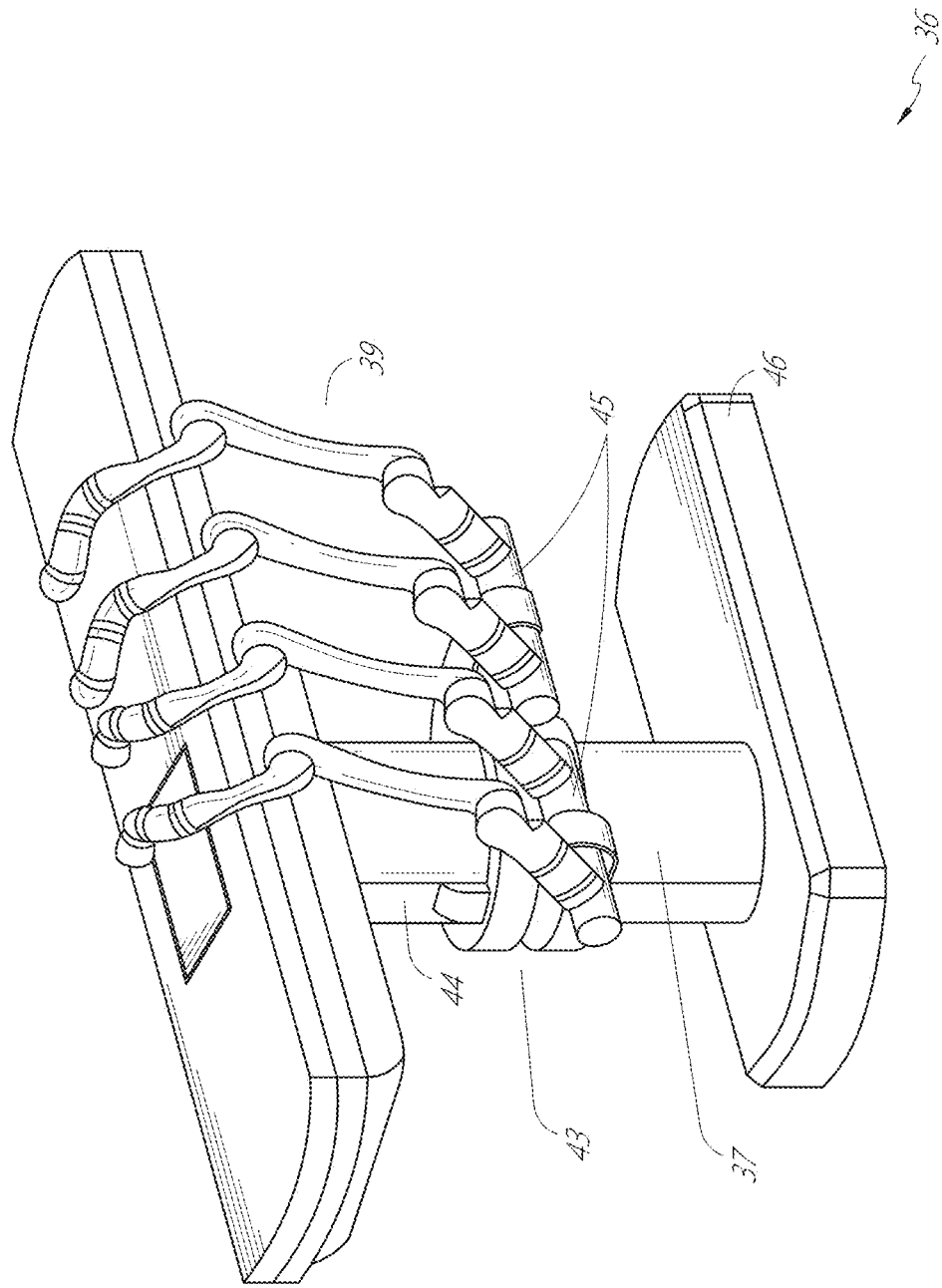
FIG. 6 provides an alternative view of the robotic system of FIG. 5.

FIG. 6 provides an alternative view of the system 36 without the patient and medical instrument for discussion purposes. As shown, the column 37 may include one or more carriages 43 shown as ring-shaped in the system 36, from which the one or more robotic arms 39 may be based. The carriages 43 may translate along a vertical column interface 44 that runs the length of the column 37 to provide different vantage points from which the robotic arms 39 may be positioned to reach the patient. The carriage(s) 43 may rotate around the column 37 using a mechanical motor positioned within the column 37 to allow the robotic arms 39 to have access to multiples sides of the table 38, such as, for example, both sides of the patient. In embodiments with multiple carriages, the carriages may be individually positioned on the column and may translate and/or rotate independently of the other carriages. While the carriages 43 need not surround the column 37 or even be circular, the ring-shape as shown facilitates rotation of the carriages 43 around the column 37 while maintaining structural balance. Rotation and translation of the carriages 43 allows the system 36 to align the medical instruments, such as endoscopes and laparoscopes, into different access points on the patient. In other embodiments (not shown), the system 36 can include a patient table or bed with adjustable arm supports in the form of bars or rails extending alongside it. One or more robotic arms 39 (e.g., via a shoulder with an elbow joint) can be attached to the adjustable arm supports, which can be vertically adjusted. By providing vertical adjustment, the robotic arms 39 are advantageously capable of being stowed compactly beneath the patient table or bed, and subsequently raised during a procedure.

Figure 9:
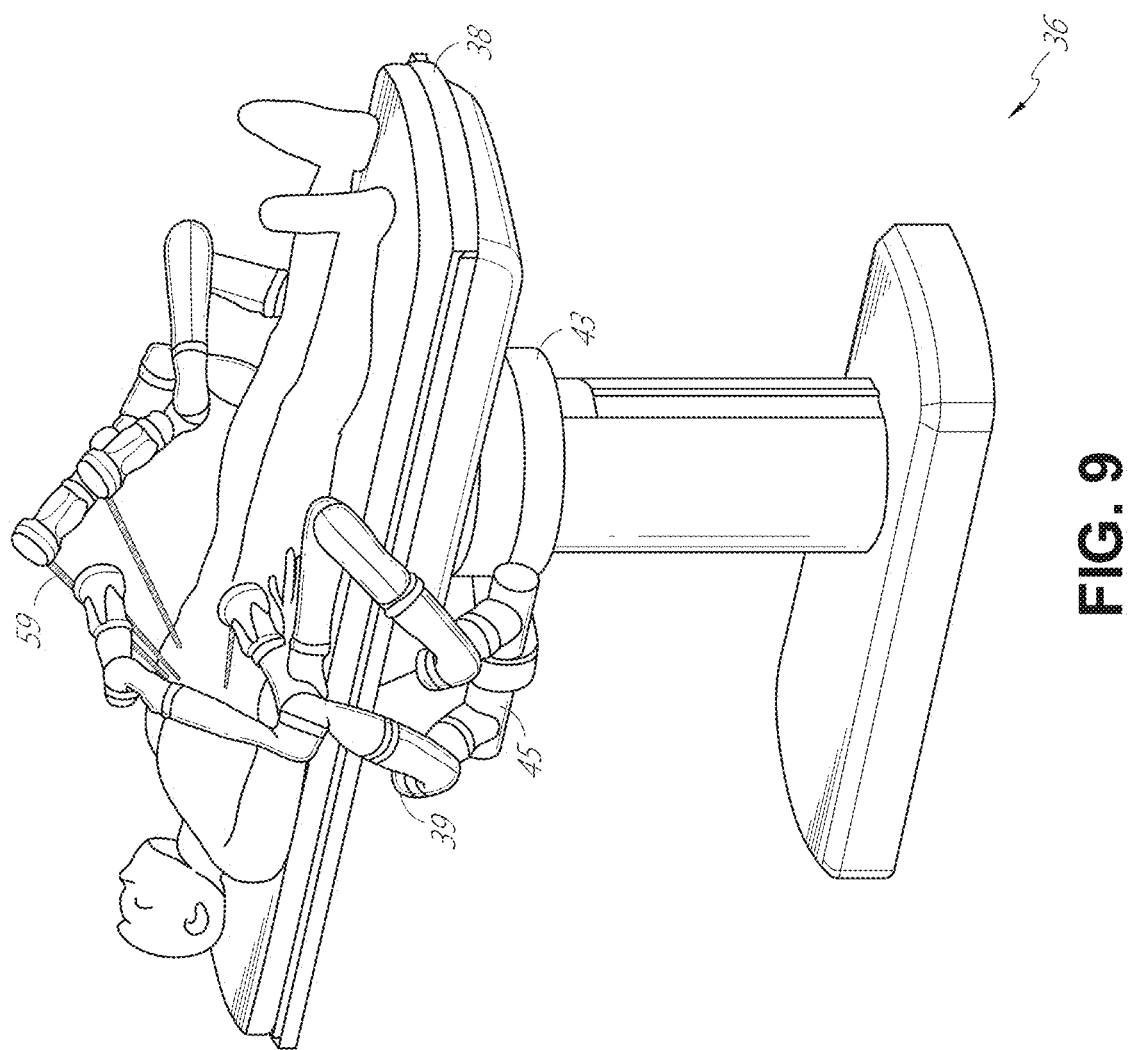
FIG. 9 illustrates an embodiment of a table-based robotic system configured for a laparoscopic procedure.

The robotic arms 39 may be mounted on the carriages through a set of arm mounts 45 comprising a series of joints that may individually rotate and/or telescopically extend to provide additional configurability to the robotic arms 39. Additionally, the arm mounts 45 may be positioned on the carriages 43 such that, when the carriages 43 are appropriately rotated, the arm mounts 45 may be positioned on either the same side of the table 38 (as shown in FIG. 6), on opposite sides of table 38 (as shown in FIG. 9), or on adjacent sides of the table 38 (not shown).

The column 37 structurally provides support for the table 38, and a path for vertical translation of the carriages 43. Internally, the column 37 may be equipped with lead screws for guiding vertical translation of the carriages, and motors to mechanize the translation of the carriages 43 based the lead screws. The column 37 may also convey power and control signals to the carriage 43 and the robotic arms 39 mounted thereon.

The table base 46 serves a similar function as the cart base 15 in cart 11 shown in FIG. 2, housing heavier components to balance the table/bed 38, the column 37, the carriages 43, and the robotic arms 39. The table base 46 may also incorporate rigid casters to provide stability during procedures. Deployed from the bottom of the table base 46, the casters may extend in opposite directions on both sides of the base 46 and retract when the system 36 needs to be moved.

With continued reference to FIG. 6, the system 36 may also include a tower (not shown) that divides the functionality of the system 36 between the table and the tower to reduce the form factor and bulk of the table. As in earlier disclosed embodiments, the tower may provide a variety of support functionalities to the table, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base 46 for potential stowage of the robotic arms 39. The tower may also include a master controller or console that provides both a user interface for user input, such as keyboard and/or pendant, as well as a display screen (or touchscreen) for pre-operative and intra-operative information, such as real-time imaging, navigation, and tracking information. In some embodiments, the tower may also contain holders for gas tanks to be used for insufflation.

Figure 7:
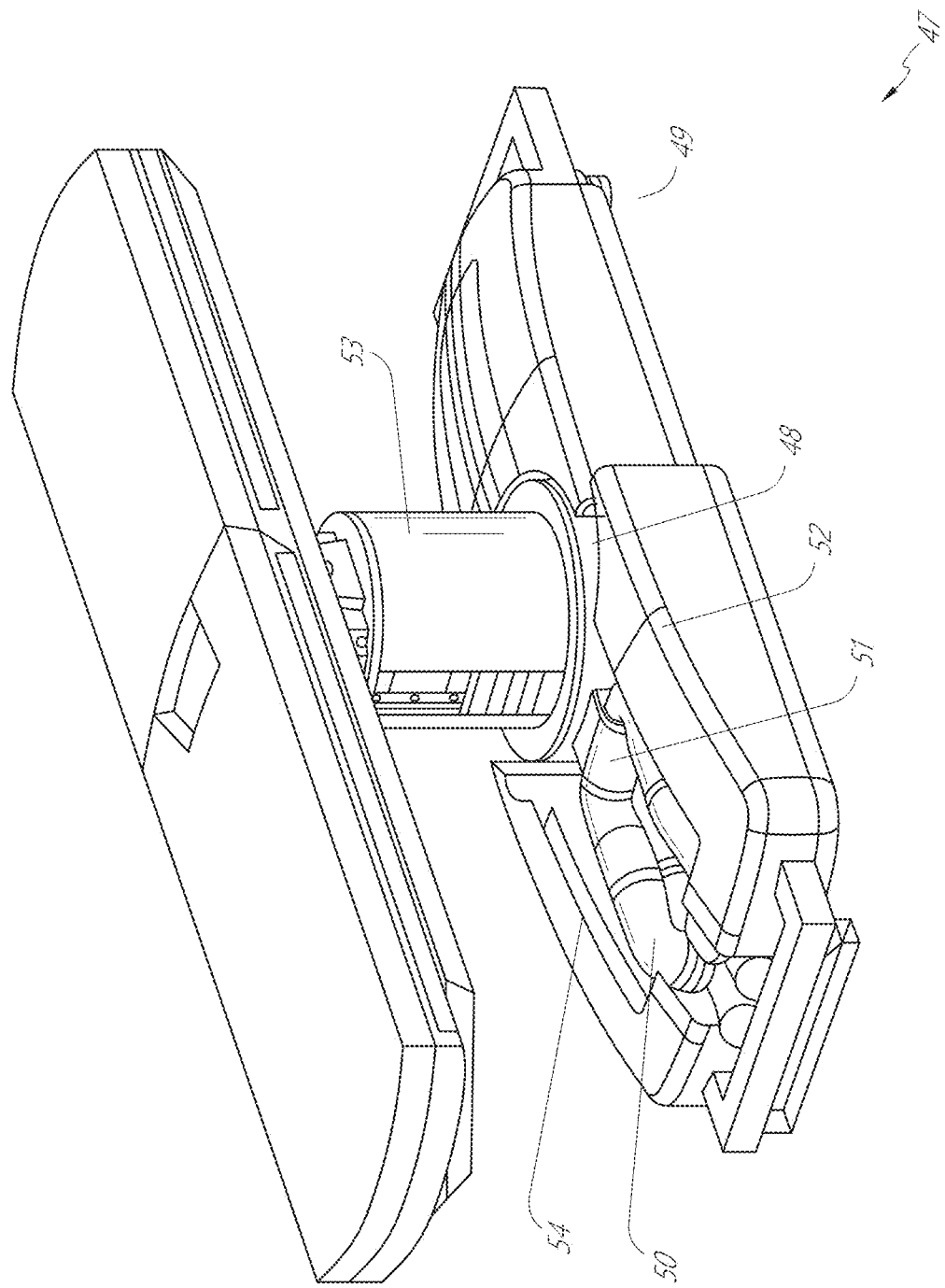
FIG. 7 illustrates an example system configured to stow robotic arm(s).

In some embodiments, a table base may stow and store the robotic arms when not in use. FIG. 7 illustrates a system 47 that stows robotic arms in an embodiment of the table-based system. In the system 47, carriages 48 may be vertically translated into base 49 to stow robotic arms 50, arm mounts 51, and the carriages 48 within the base 49. Base covers 52 may be translated and retracted open to deploy the carriages 48, arm mounts 51, and robotic arms 50 around column 53, and closed to stow to protect them when not in use. The base covers 52 may be sealed with a membrane 54 along the edges of its opening to prevent dirt and fluid ingress when closed.

Figure 8:
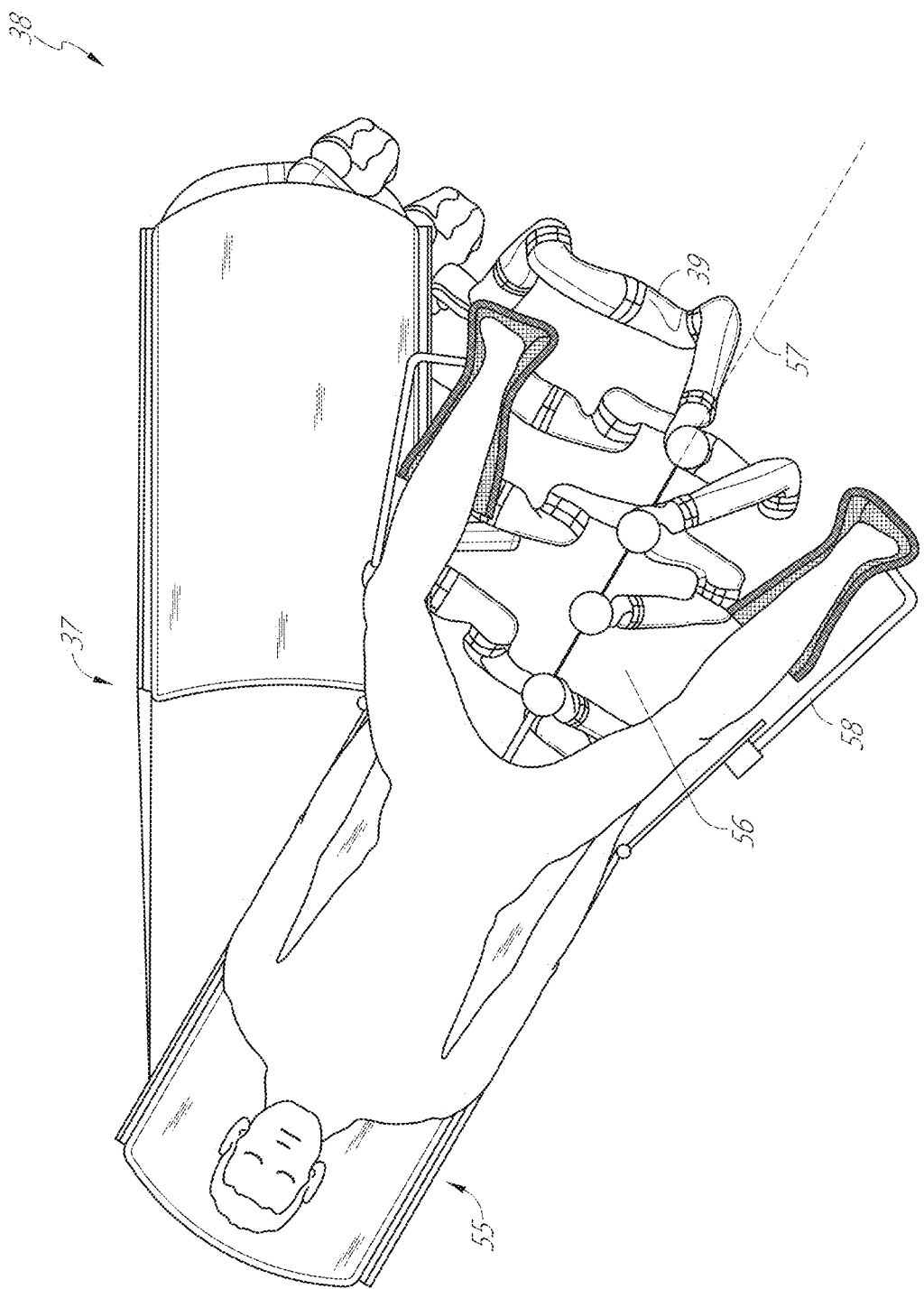
FIG. 8 illustrates an embodiment of a table-based robotic system configured for a ureteroscopic procedure.

FIG. 8 illustrates an embodiment of a robotically-enabled table-based system configured for a ureteroscopic procedure. In a ureteroscopy, the table 38 may include a swivel portion 55 for positioning a patient off-angle from the column 37 and table base 46. The swivel portion 55 may rotate or pivot around a pivot point (e.g., located below the patient's head) in order to position the bottom portion of the swivel portion 55 away from the column 37. For example, the pivoting of the swivel portion 55 allows a C-arm (not shown) to be positioned over the patient's lower abdomen without competing for space with the column (not shown) below table 38. By rotating the carriage 35 (not shown) around the column 37, the robotic arms 39 may directly insert a ureteroscope 56 along a virtual rail 57 into the patient's groin area to reach the urethra. In a ureteroscopy, stirrups 58 may also be fixed to the swivel portion 55 of the table 38 to support the position of the patient's legs during the procedure and allow clear access to the patient's groin area.

In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope. FIG. 9 illustrates an embodiment of a robotically-enabled table-based system configured for a laparoscopic procedure. As shown in FIG. 9, the carriages 43 of the system 36 may be rotated and vertically adjusted to position pairs of the robotic arms 39 on opposite sides of the table 38, such that instrument 59 may be positioned using the arm mounts 45 to be passed through minimal incisions on both sides of the patient to reach his/her abdominal cavity.

Figure 10:
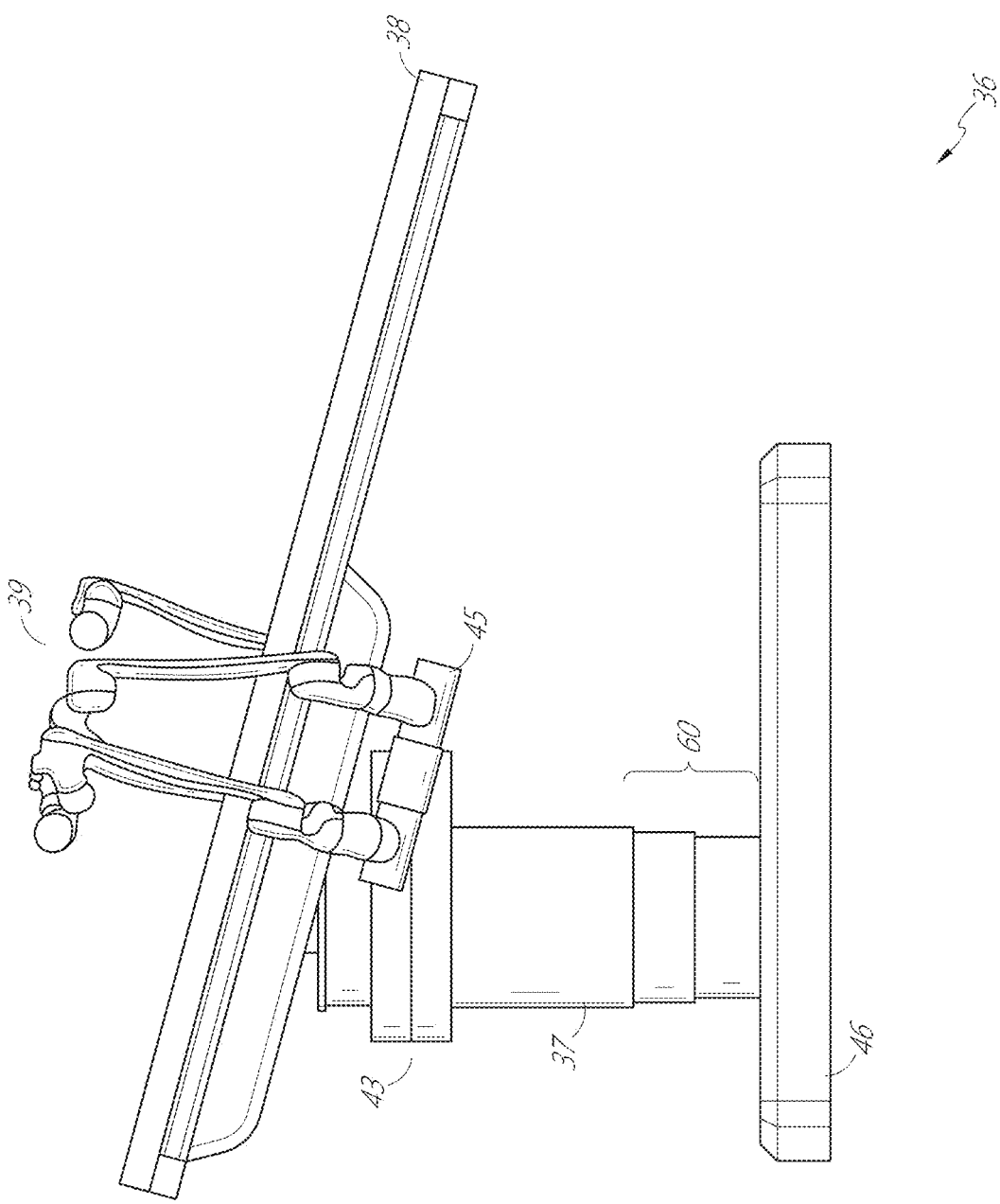
FIG. 10 illustrates an embodiment of the table-based robotic system of FIGS. 5-9 with pitch or tilt adjustment.

To accommodate laparoscopic procedures, the robotically-enabled table system may also tilt the platform to a desired angle. FIG. 10 illustrates an embodiment of the robotically-enabled medical system with pitch or tilt adjustment. As shown in FIG. 10, the system 36 may accommodate tilt of the table 38 to position one portion of the table at a greater distance from the floor than the other. Additionally, the arm mounts 45 may rotate to match the tilt such that the robotic arms 39 maintain the same planar relationship with table 38. To accommodate steeper angles, the column 37 may also include telescoping portions 60 that allow vertical extension of the column 37 to keep the table 38 from touching the floor or colliding with the table base 46.

Figure 11:
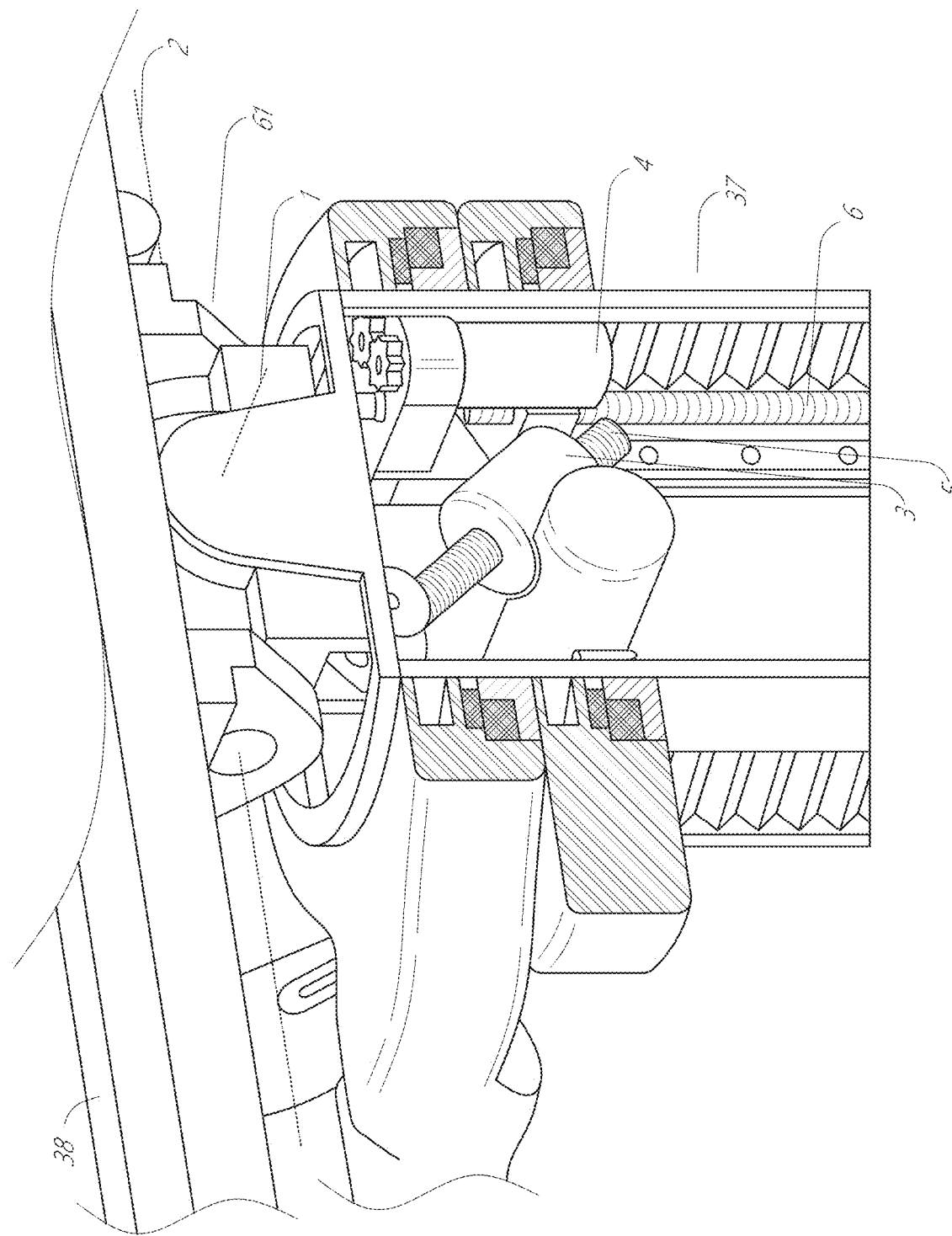
FIG. 11 provides a detailed illustration of the interface between the table and the column of the table-based robotic system of FIGS. 5-10.

FIG. 11 provides a detailed illustration of the interface between the table 38 and the column 37. Pitch rotation mechanism 61 may be configured to alter the pitch angle of the table 38 relative to the column 37 in multiple degrees of freedom. The pitch rotation mechanism 61 may be enabled by the positioning of orthogonal axes 1, 2 at the column-table interface, each axis actuated by a separate motor 3, 4 responsive to an electrical pitch angle command. Rotation along one screw 5 would enable tilt adjustments in one axis 1, while rotation along the other screw 6 would enable tilt adjustments along the other axis 2. In some embodiments, a ball joint can be used to alter the pitch angle of the table 38 relative to the column 37 in multiple degrees of freedom.

For example, pitch adjustments are particularly useful when trying to position the table in a Trendelenburg position, i.e., position the patient's lower abdomen at a higher position from the floor than the patient's lower abdomen, for upper abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

Figure 12:
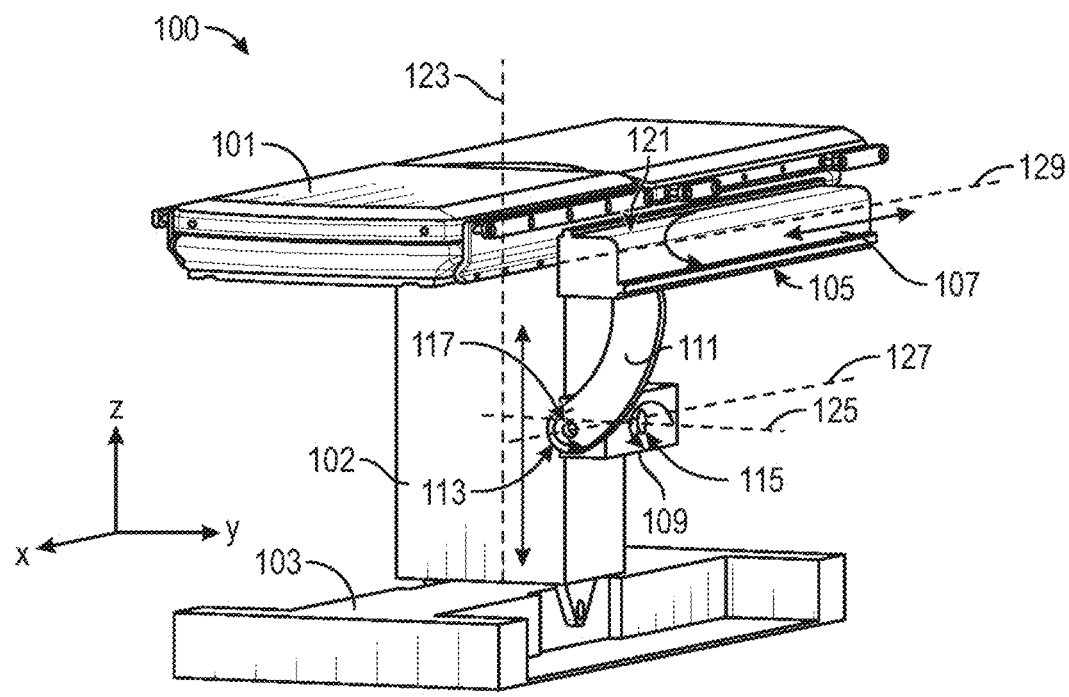
FIG. 12 illustrates an alternative embodiment of a table-based robotic system.
Figure 13:
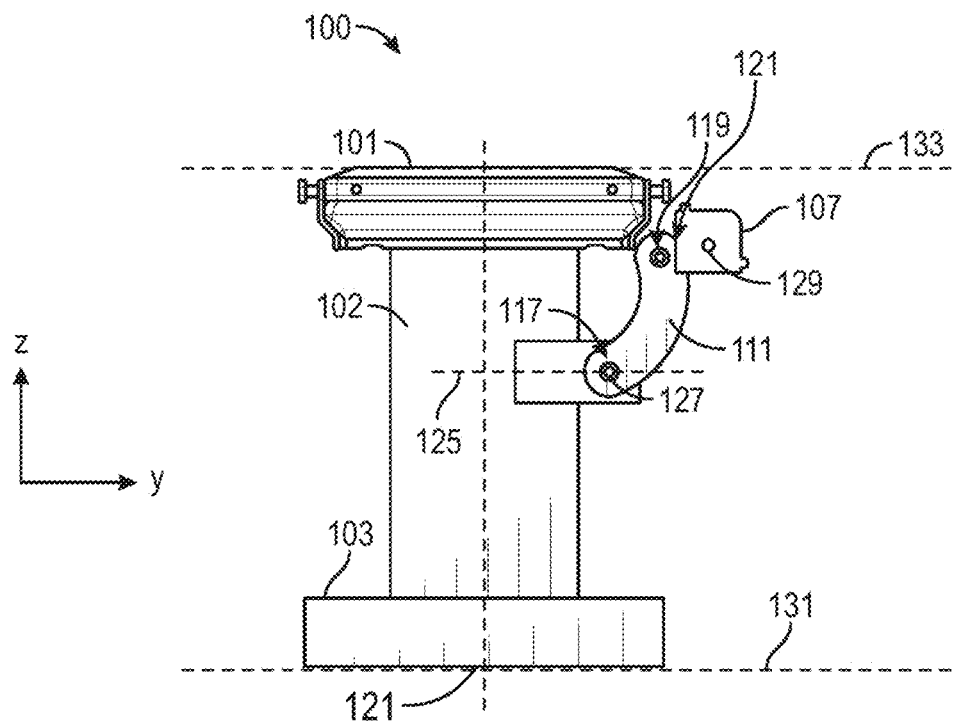
FIG. 13 illustrates an end view of the table-based robotic system of FIG. 12.

FIGS. 12 and 13 illustrate isometric and end views of an alternative embodiment of a table-based surgical robotics system 100. The surgical robotics system 100 includes one or more adjustable arm supports 105 that can be configured to support one or more robotic arms (see, for example, FIG. 14) relative to a table 101. In the illustrated embodiment, a single adjustable arm support 105 is shown, though an additional arm support can be provided on an opposite side of the table 101. The adjustable arm support 105 can be configured so that it can move relative to the table 101 to adjust and/or vary the position of the adjustable arm support 105 and/or any robotic arms mounted thereto relative to the table 101. For example, the adjustable arm support 105 may be adjusted one or more degrees of freedom relative to the table 101. The adjustable arm support 105 provides high versatility to the system 100, including the ability to easily stow the one or more adjustable arm supports 105 and any robotics arms attached thereto beneath the table 101. The adjustable arm support 105 can be elevated from the stowed position to a position below an upper surface of the table 101. In other embodiments, the adjustable arm support 105 can be elevated from the stowed position to a position above an upper surface of the table 101.

The adjustable arm support 105 can provide several degrees of freedom, including lift, lateral translation, tilt, etc. In the illustrated embodiment of FIGS. 12 and 13, the arm support 105 is configured with four degrees of freedom, which are illustrated with arrows in FIG. 12. A first degree of freedom allows for adjustment of the adjustable arm support 105 in the z-direction ("Z-lift"). For example, the adjustable arm support 105 can include a carriage 109 configured to move up or down along or relative to a column 102 supporting the table 101. A second degree of freedom can allow the adjustable arm support 105 to tilt. For example, the adjustable arm support 105 can include a rotary joint, which can allow the adjustable arm support 105 to be aligned with the bed in a Trendelenburg position. A third degree of freedom can allow the adjustable arm support 105 to "pivot up," which can be used to adjust a distance between a side of the table 101 and the adjustable arm support 105. A fourth degree of freedom can permit translation of the adjustable arm support 105 along a longitudinal length of the table.

The surgical robotics system 100 in FIGS. 12 and 13 can comprise a table supported by a column 102 that is mounted to a base 103. The base 103 and the column 102 support the table 101 relative to a support surface. A floor axis 131 and a support axis 133 are shown in FIG. 13.

The adjustable arm support 105 can be mounted to the column 102. In other embodiments, the arm support 105 can be mounted to the table 101 or base 103. The adjustable arm support 105 can include a carriage 109, a bar or rail connector 111 and a bar or rail 107. In some embodiments, one or more robotic arms mounted to the rail 107 can translate and move relative to one another.

The carriage 109 can be attached to the column 102 by a first joint 113, which allows the carriage 109 to move relative to the column 102 (e.g., such as up and down a first or vertical axis 123). The first joint 113 can provide the first degree of freedom ("Z-lift") to the adjustable arm support 105. The adjustable arm support 105 can include a second joint 115, which provides the second degree of freedom (tilt) for the adjustable arm support 105. The adjustable arm support 105 can include a third joint 117, which can provide the third degree of freedom ("pivot up") for the adjustable arm support 105. An additional joint 119 (shown in FIG. 13) can be provided that mechanically constrains the third joint 117 to maintain an orientation of the rail 107 as the rail connector 111 is rotated about a third axis 127. The adjustable arm support 105 can include a fourth joint 121, which can provide a fourth degree of freedom (translation) for the adjustable arm support 105 along a fourth axis 129.

Figure 14:
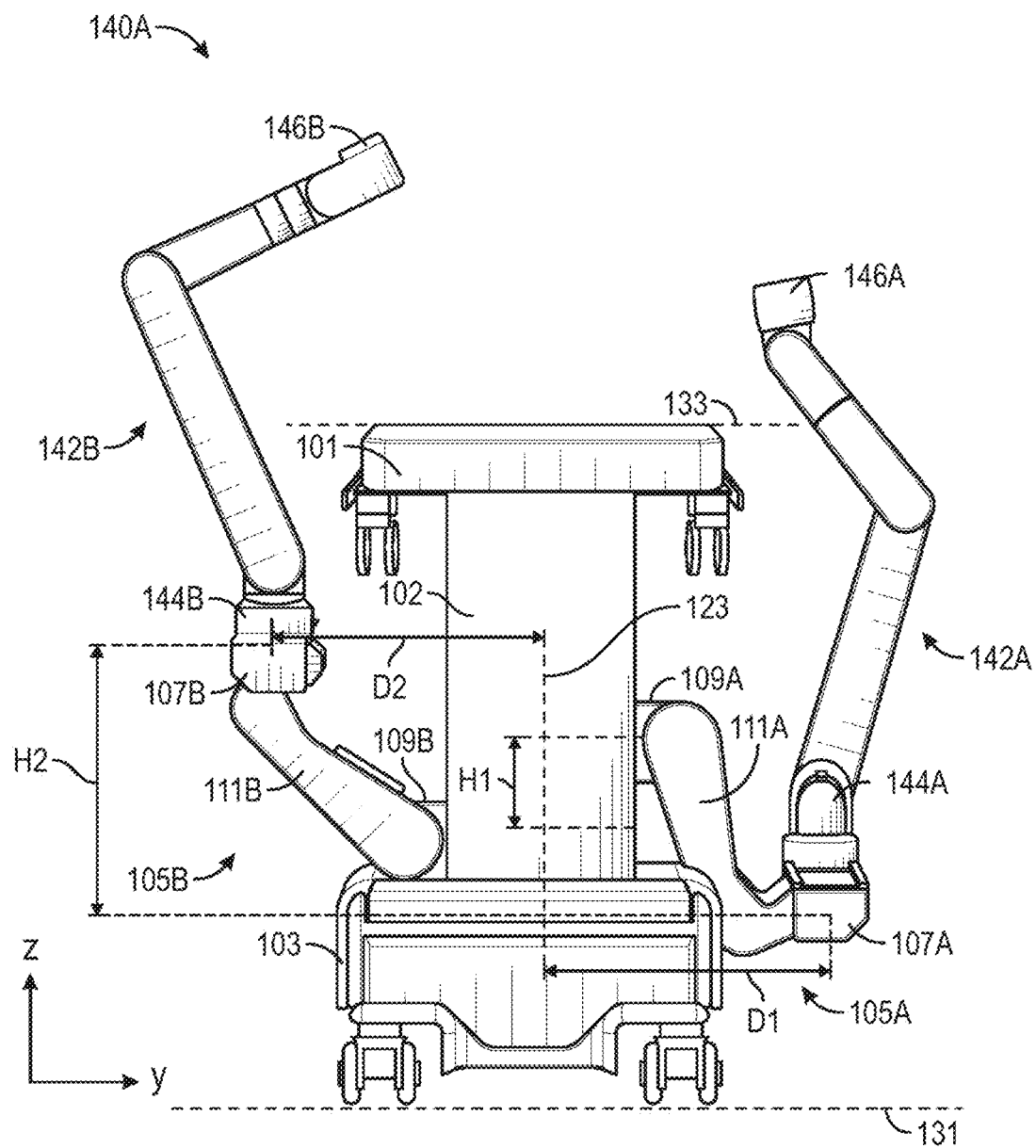
FIG. 14 illustrates an end view of a table-based robotic system with robotic arms attached thereto.

FIG. 14 illustrates an end view of the surgical robotics system 140A with two adjustable arm supports 105A, 105B mounted on opposite sides of a table 101. A first robotic arm 142A is attached to the bar or rail 107A of the first adjustable arm support 105B. The first robotic arm 142A includes a base 144A attached to the rail 107A. The distal end of the first robotic arm 142A includes an instrument drive mechanism 146A that can attach to one or more robotic medical instruments or tools. Similarly, the second robotic arm 142B includes a base 144B attached to the rail 107B. The distal end of the second robotic arm 142B includes an instrument drive mechanism 146B. The instrument drive mechanism 146B can be configured to attach to one or more robotic medical instruments or tools.

In some embodiments, one or more of the robotic arms 142A, 142B comprises an arm with seven or more degrees of freedom. In some embodiments, one or more of the robotic arms 142A, 142B can include eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base 144A, 144B (1-degree of freedom including translation). In some embodiments, the insertion degree of freedom can be provided by the robotic arm 142A, 142B, while in other embodiments, the instrument itself provides insertion via an instrument-based insertion architecture.

C. Instrument Driver & Interface.

The end effectors of the system's robotic arms may comprise (i) an instrument driver (alternatively referred to as "instrument drive mechanism" or "instrument device manipulator") that incorporates electro-mechanical means for actuating the medical instrument and (ii) a removable or detachable medical instrument, which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 15:
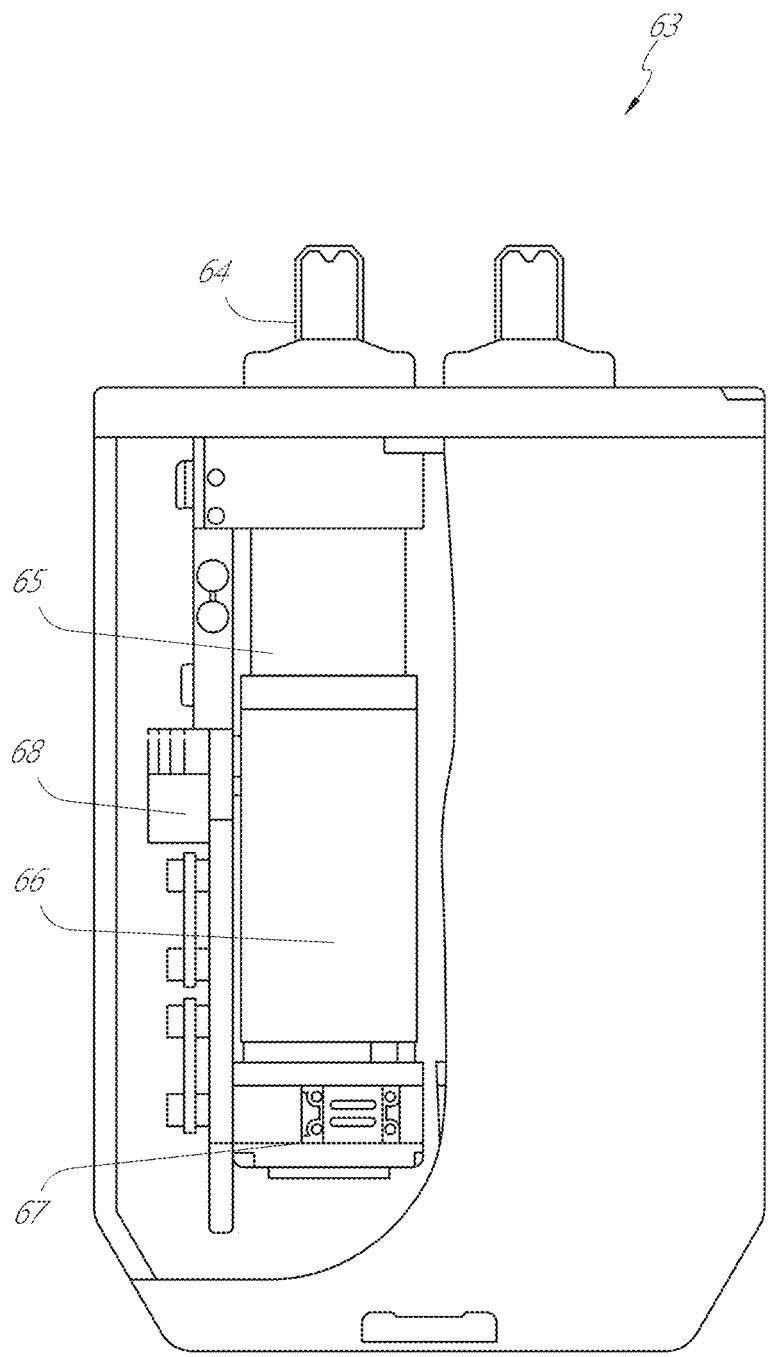
FIG. 15 illustrates an exemplary instrument driver.

FIG. 15 illustrates an example instrument driver. Positioned at the distal end of a robotic arm, instrument driver 62 comprises of one or more drive units 63 arranged with parallel axes to provide controlled torque to a medical instrument via drive shafts 64. Each drive unit 63 comprises an individual drive shaft 64 for interacting with the instrument, a gear head 65 for converting the motor shaft rotation to a desired torque, a motor 66 for generating the drive torque, an encoder 67 to measure the speed of the motor shaft and provide feedback to the control circuitry, and control circuitry 68 for receiving control signals and actuating the drive unit. Each drive unit 63 being independently controlled and motorized, the instrument driver 62 may provide multiple (four as shown in FIG. 15) independent drive outputs to the medical instrument. In operation, the control circuitry 68 would receive a control signal, transmit a motor signal to the motor 66, compare the resulting motor speed as measured by the encoder 67 with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise of a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 16:
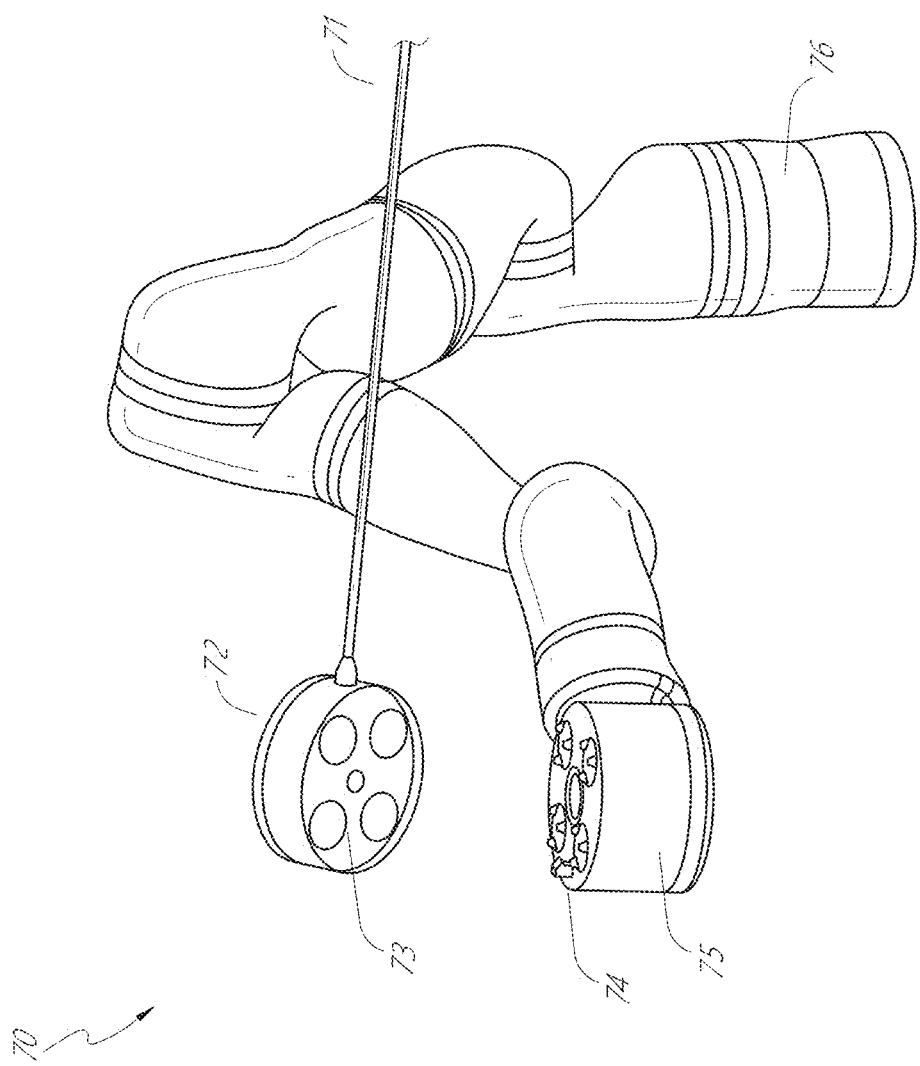
FIG. 16 illustrates an exemplary medical instrument with a paired instrument driver.

FIG. 16 illustrates an example medical instrument with a paired instrument driver. Like other instruments designed for use with a robotic system, medical instrument 70 comprises an elongated shaft 71 (or elongate body) and an instrument base 72. The instrument base 72, also referred to as an "instrument handle" due to its intended design for manual interaction by the physician, may generally comprise rotatable drive inputs 73, e.g., receptacles, pulleys or spools, that are designed to be mated with drive outputs 74 that extend through a drive interface on instrument driver 75 at the distal end of robotic arm 76. When physically connected, latched, and/or coupled, the mated drive inputs 73 of instrument base 72 may share axes of rotation with the drive outputs 74 in the instrument driver 75 to allow the transfer of torque from the drive outputs 74 to the drive inputs 73. In some embodiments, the drive outputs 74 may comprise splines that are designed to mate with receptacles on the drive inputs 73.

The elongated shaft 71 is designed to be delivered through either an anatomical opening or lumen, e.g., as in endoscopy, or a minimally invasive incision, e.g., as in laparoscopy. The elongated shaft 71 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector extending from a jointed wrist formed from a clevis with at least one degree of freedom and a surgical tool or medical instrument, such as, for example, a grasper or scissors, that may be actuated based on force from the tendons as the drive inputs rotate in response to torque received from the drive outputs 74 of the instrument driver 75. When designed for endoscopy, the distal end of a flexible elongated shaft may include a steerable or controllable bending section that may be articulated and bent based on torque received from the drive outputs 74 of the instrument driver 75.

Torque from the instrument driver 75 is transmitted down the elongated shaft 71 using tendons along the elongated shaft 71. These individual tendons, such as pull wires, may be individually anchored to individual drive inputs 73 within the instrument handle 72. From the handle 72, the tendons are directed down one or more pull lumens along the elongated shaft 71 and anchored at the distal portion of the elongated shaft 71, or in the wrist at the distal portion of the elongated shaft. During a surgical procedure, such as a laparoscopic, endoscopic or hybrid procedure, these tendons may be coupled to a distally mounted end effector, such as a wrist, grasper, or scissor. Under such an arrangement, torque exerted on drive inputs 73 would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at the distal end of the elongated shaft 71, where tension from the tendon causes the grasper to close.

In endoscopy, the tendons may be coupled to a bending or articulating section positioned along the elongated shaft 71 (e.g., at the distal end) via adhesive, control ring, or other mechanical fixation. When fixedly attached to the distal end of a bending section, torque exerted on the drive inputs 73 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing therebetween may be altered or engineered for specific purposes, wherein tighter spiraling exhibits lesser shaft compression under load forces, while lower amounts of spiraling results in greater shaft compression under load forces, but limits bending. On the other end of the spectrum, the pull lumens may be directed parallel to the longitudinal axis of the elongated shaft 71 to allow for controlled articulation in the desired bending or articulable sections.

In endoscopy, the elongated shaft 71 houses a number of components to assist with the robotic procedure. The shaft 71 may comprise a working channel for deploying surgical tools (or medical instruments), irrigation, and/or aspiration to the operative region at the distal end of the shaft 71. The shaft 71 may also accommodate wires and/or optical fibers to transfer signals to/from an optical assembly at the distal tip, which may include an optical camera. The shaft 71 may also accommodate optical fibers to carry light from proximally-located light sources, such as light emitting diodes, to the distal end of the shaft 71.

At the distal end of the instrument 70, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 16, the drive shaft axes, and thus the drive input axes, are orthogonal to the axis of the elongated shaft 71. This arrangement, however, complicates roll capabilities for the elongated shaft 71. Rolling the elongated shaft 71 along its axis while keeping the drive inputs 73 static results in undesirable tangling of the tendons as they extend off the drive inputs 73 and enter pull lumens within the elongated shaft 71. The resulting entanglement of such tendons may disrupt any control algorithms intended to predict movement of the flexible elongated shaft 71 during an endoscopic procedure.

Figure 17:
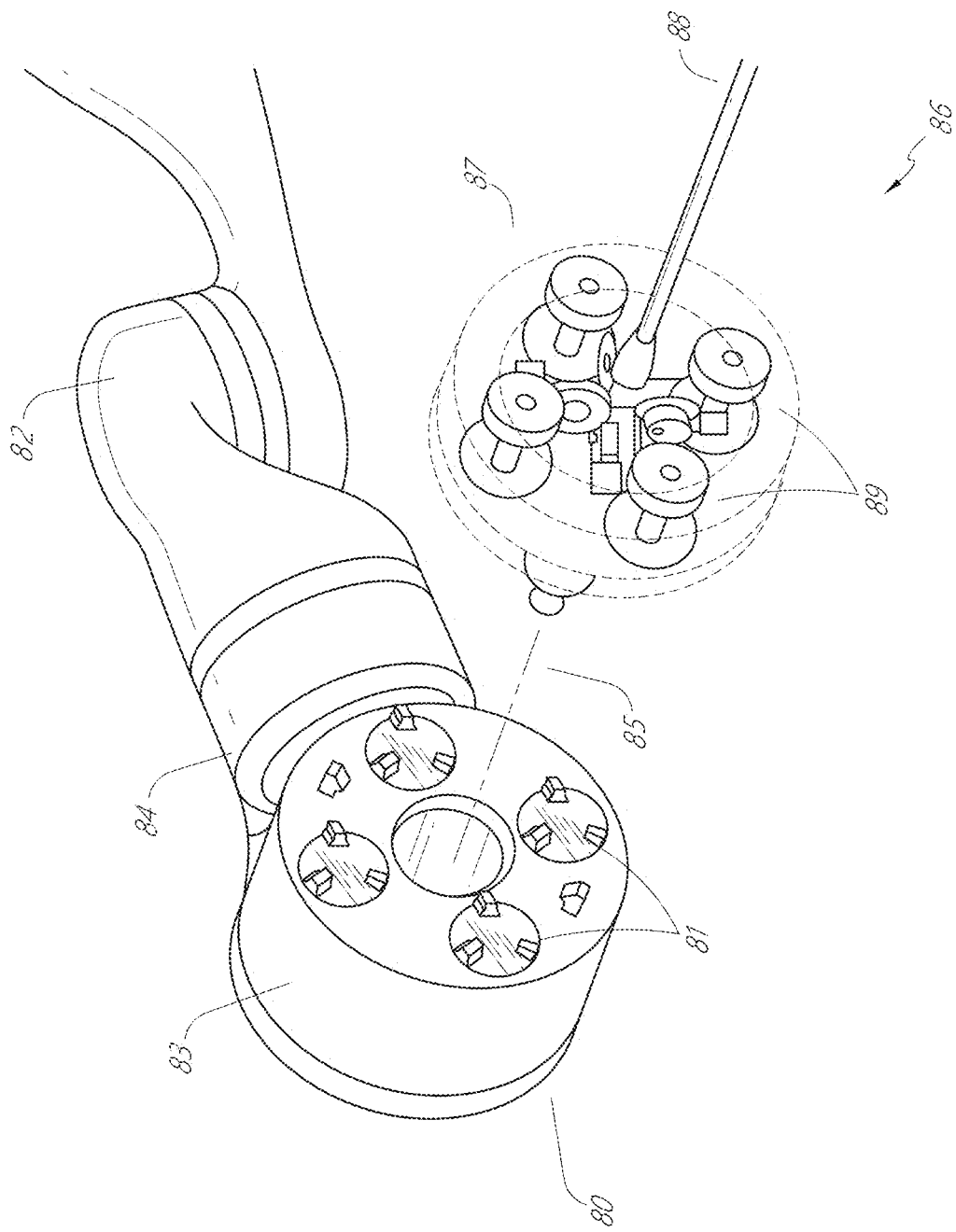
FIG. 17 illustrates an alternative design for an instrument driver and instrument where the axes of the drive units are parallel to the axis of the elongated shaft of the instrument.

FIG. 17 illustrates an alternative design for an instrument driver and instrument where the axes of the drive units are parallel to the axis of the elongated shaft of the instrument. As shown, a circular instrument driver 80 comprises four drive units with their drive outputs 81 aligned in parallel at the end of a robotic arm 82. The drive units, and their respective drive outputs 81, are housed in a rotational assembly 83 of the instrument driver 80 that is driven by one of the drive units within the assembly 83. In response to torque provided by the rotational drive unit, the rotational assembly 83 rotates along a circular bearing that connects the rotational assembly 83 to the non-rotational portion 84 of the instrument driver 80. Power and controls signals may be communicated from the non-rotational portion 84 of the instrument driver 80 to the rotational assembly 83 through electrical contacts that may be maintained through rotation by a brushed slip ring connection (not shown). In other embodiments, the rotational assembly 83 may be responsive to a separate drive unit that is integrated into the non-rotatable portion 84, and thus not in parallel to the other drive units. The rotational mechanism 83 allows the instrument driver 80 to rotate the drive units, and their respective drive outputs 81, as a single unit around an instrument driver axis 85.

Like earlier disclosed embodiments, an instrument 86 may comprise an elongated shaft portion 88 and an instrument base 87 (shown with a transparent external skin for discussion purposes) comprising a plurality of drive inputs 89 (such as receptacles, pulleys, and spools) that are configured to receive the drive outputs 81 in the instrument driver 80. Unlike prior disclosed embodiments, the instrument shaft 88 extends from the center of the instrument base 87 with an axis substantially parallel to the axes of the drive inputs 89, rather than orthogonal as in the design of FIG. 16.

When coupled to the rotational assembly 83 of the instrument driver 80, the medical instrument 86, comprising instrument base 87 and instrument shaft 88, rotates in combination with the rotational assembly 83 about the instrument driver axis 85. Since the instrument shaft 88 is positioned at the center of instrument base 87, the instrument shaft 88 is coaxial with instrument driver axis 85 when attached. Thus, rotation of the rotational assembly 83 causes the instrument shaft 88 to rotate about its own longitudinal axis. Moreover, as the instrument base 87 rotates with the instrument shaft 88, any tendons connected to the drive inputs 89 in the instrument base 87 are not tangled during rotation. Accordingly, the parallelism of the axes of the drive outputs 81, drive inputs 89, and instrument shaft 88 allows for the shaft rotation without tangling any control tendons.

Figure 18:
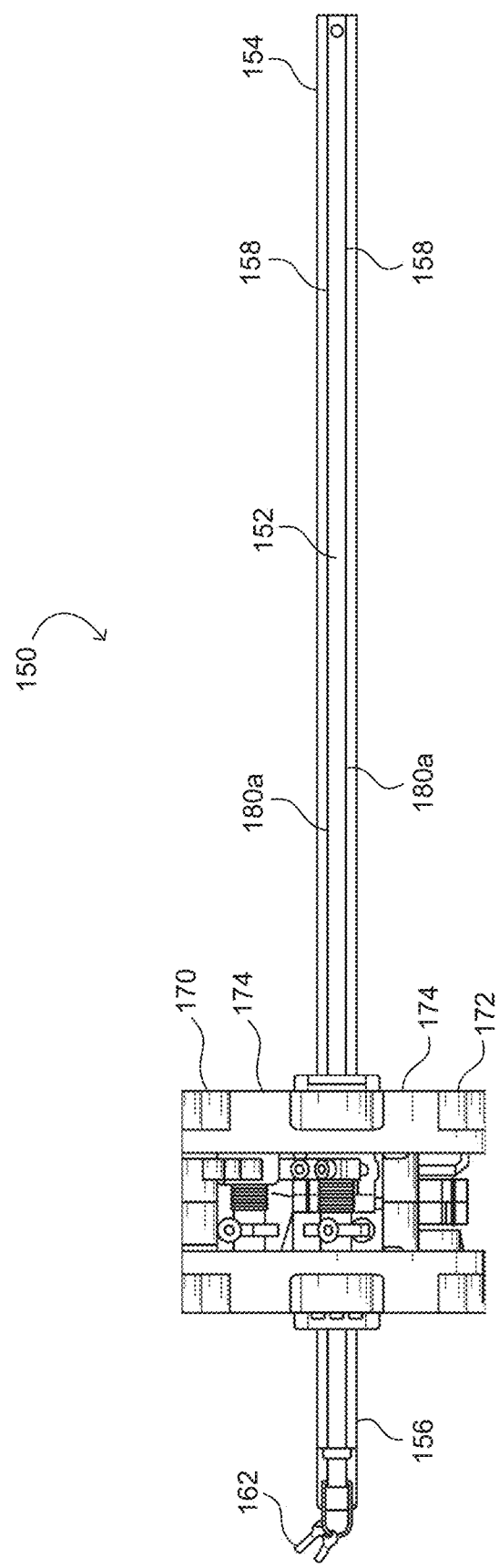
FIG. 18 illustrates an instrument having an instrument-based insertion architecture.

FIG. 18 illustrates an instrument having an instrument based insertion architecture in accordance with some embodiments. The instrument 150 can be coupled to any of the instrument drivers discussed above. The instrument 150 comprises an elongated shaft 152, an end effector 162 connected to the shaft 152, and a handle 170 coupled to the shaft 152. The elongated shaft 152 comprises a tubular member having a proximal portion 154 and a distal portion 156. The elongated shaft 152 comprises one or more channels or grooves 158 along its outer surface. The grooves 158 are configured to receive one or more wires or cables 180 therethrough. One or more cables 180 thus run along an outer surface of the elongated shaft 152. In other embodiments, cables 180 can also run through the elongated shaft 152. Manipulation of the one or more cables 180 (e.g., via an instrument driver) results in actuation of the end effector 162.

The instrument handle 170, which may also be referred to as an instrument base, may generally comprise an attachment interface 172 having one or more mechanical inputs 174, e.g., receptacles, pulleys or spools, that are designed to be reciprocally mated with one or more torque couplers on an attachment surface of an instrument driver.

In some embodiments, the instrument 150 comprises a series of pulleys or cables that enable the elongated shaft 152 to translate relative to the handle 170. In other words, the instrument 150 itself comprises an instrument-based insertion architecture that accommodates insertion of the instrument, thereby minimizing the reliance on a robot arm to provide insertion of the instrument 150. In other embodiments, a robotic arm can be largely responsible for instrument insertion.

E. Controller.

Any of the robotic systems described herein can include an input device or controller for manipulating an instrument attached to a robotic arm. In some embodiments, the controller can be coupled (e.g., communicatively, electronically, electrically, wirelessly and/or mechanically) with an instrument such that manipulation of the controller causes a corresponding manipulation of the instrument e.g., via master slave control.

Figure 19:
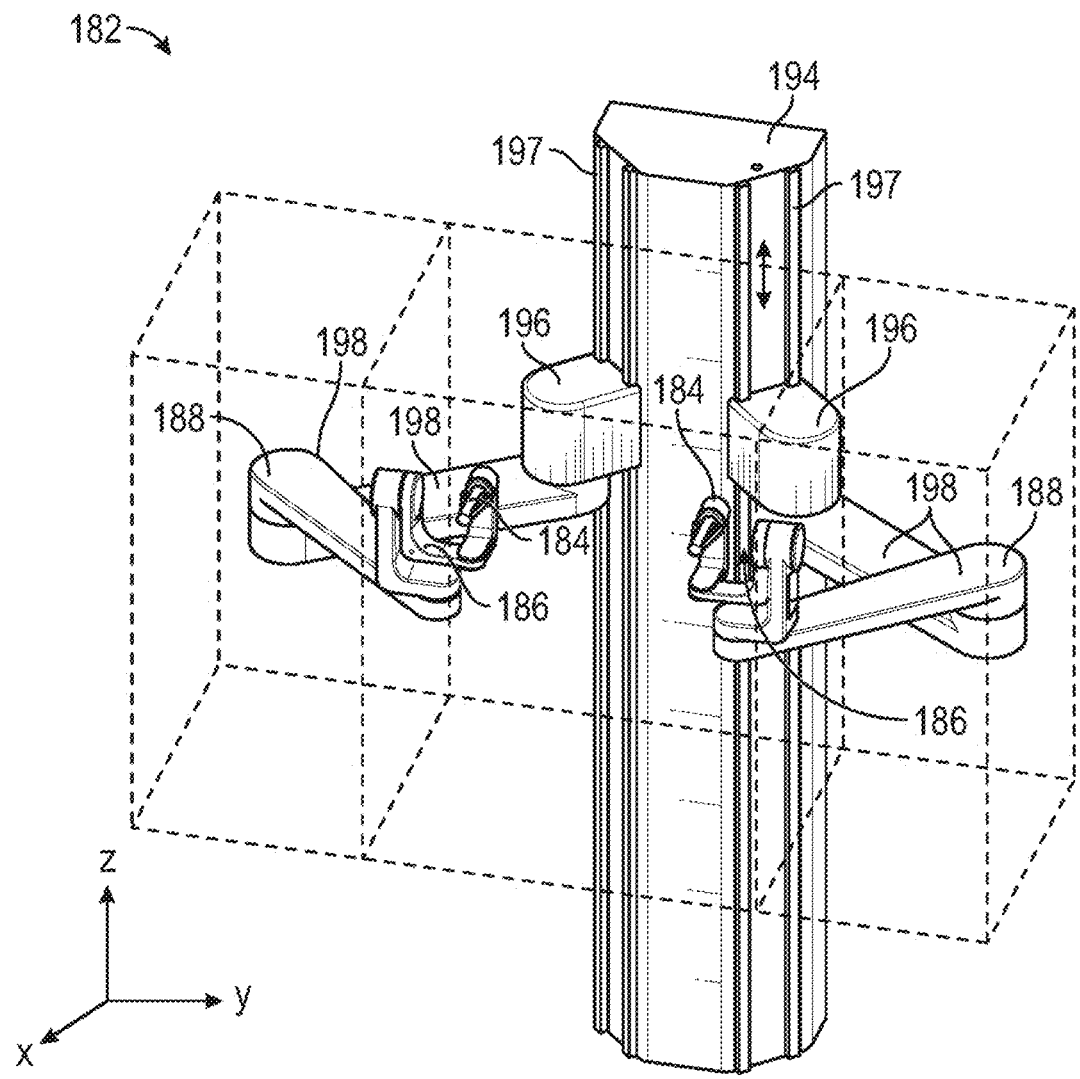
FIG. 19 illustrates an exemplary controller.

FIG. 19 is a perspective view of an embodiment of a controller 182. In the present embodiment, the controller 182 comprises a hybrid controller that can have both impedance and admittance control. In other embodiments, the controller 182 can utilize just impedance or passive control. In other embodiments, the controller 182 can utilize just admittance control. By being a hybrid controller, the controller 182 advantageously can have a lower perceived inertia while in use.

In the illustrated embodiment, the controller 182 is configured to allow manipulation of two medical instruments, and includes two handles 184. Each of the handles 184 is connected to a gimbal 186. Each gimbal 186 is connected to a positioning platform 188.

As shown in FIG. 19, each positioning platform 188 includes a SCARA arm (selective compliance assembly robot arm) 198 coupled to a column 194 by a prismatic joint 196. The prismatic joints 196 are configured to translate along the column 194 (e.g., along rails 197) to allow each of the handles 184 to be translated in the z-direction, providing a first degree of freedom. The SCARA arm 198 is configured to allow motion of the handle 184 in an x-y plane, providing two additional degrees of freedom.

In some embodiments, one or more load cells are positioned in the controller. For example, in some embodiments, a load cell (not shown) is positioned in the body of each of the gimbals 186. By providing a load cell, portions of the controller 182 are capable of operating under admittance control, thereby advantageously reducing the perceived inertia of the controller while in use. In some embodiments, the positioning platform 188 is configured for admittance control, while the gimbal 186 is configured for impedance control. In other embodiments, the gimbal 186 is configured for admittance control, while the positioning platform 188 is configured for impedance control. Accordingly, for some embodiments, the translational or positional degrees of freedom of the positioning platform 188 can rely on admittance control, while the rotational degrees of freedom of the gimbal 186 rely on impedance control.

F. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as pre-operative mapping, computer vision, real-time EM tracking, and robot command data may be used individually or in combination to achieve a radiation-free operating environment. In other cases, where radiation-based imaging modalities are still used, the pre-operative mapping, computer vision, real-time EM tracking, and robot command data may be used individually or in combination to improve upon the information obtained solely through radiation-based imaging modalities.

Figure 20:
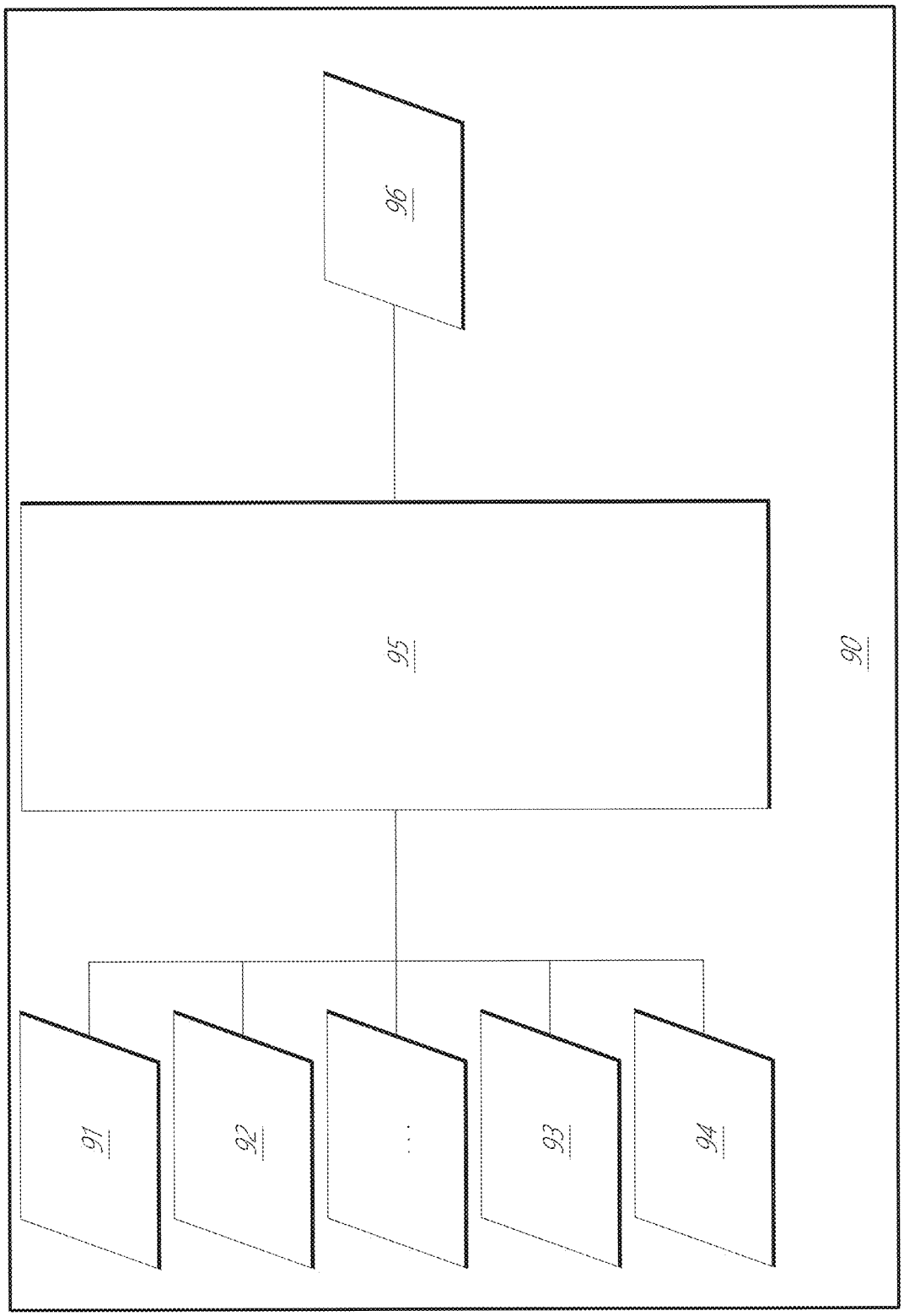
FIG. 20 depicts a block diagram illustrating a localization system that estimates a location of one or more elements of the robotic systems of FIGS. 1-10, such as the location of the instrument of FIGS. 16-18, in accordance to an example embodiment.

FIG. 20 is a block diagram illustrating a localization system 90 that estimates a location of one or more elements of the robotic system, such as the location of the instrument, in accordance to an example embodiment. The localization system 90 may be a set of one or more computer devices configured to execute one or more instructions. The computer devices may be embodied by a processor (or processors) and computer-readable memory in one or more components discussed above. By way of example and not limitation, the computer devices may be in the tower 30 shown in FIG. 1, the cart 11 shown in FIGS. 1-4, the beds shown in FIGS. 5-14, etc.

As shown in FIG. 20, the localization system 90 may include a localization module 95 that processes input data 91-94 to generate location data 96 for the distal tip of a medical instrument. The location data 96 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 91-94 are now described in greater detail. Pre-operative mapping may be accomplished through the use of the collection of low dose CT scans. Pre-operative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as model data 91 (also referred to as "preoperative model data" when generated using only preoperative CT scans). The use of center-line geometry is discussed in U.S. patent application Ser. No. 14/523,760, published as U.S. Pat. Pub. No. 2015/0119637 on Apr. 30, 2015, issued as U.S. Pat. No. 9,763,741 on Sep. 19, 2017, the contents of which are herein incorporated in its entirety. Network topological models may also be derived from the CT-images, and are particularly appropriate for bronchoscopy.

In some embodiments, the instrument may be equipped with a camera to provide vision data (or image data) 92. The localization module 95 may process the vision data to enable one or more vision-based (or image-based) location tracking modules or features. For example, the preoperative model data may be used in conjunction with the vision data 92 to enable computer vision-based tracking of the medical instrument (e.g., an endoscope or an instrument advance through a working channel of the endoscope). For example, using the preoperative model data 91, the robotic system may generate a library of expected endoscopic images from the model based on the expected path of travel of the endoscope, each image linked to a location within the model. Intra-operatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 95 may identify circular geometries in the preoperative model data 91 that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 92 to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 95 may use real-time EM tracking to generate a real-time location of the endoscope in a global coordinate system that may be registered to the patient's anatomy, represented by the preoperative model. In EM tracking, an EM sensor (or tracker) comprising of one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 93. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intra-operatively "registered" to the patient anatomy (e.g., the preoperative model) in order to determine the geometric transformation that aligns a single location in the coordinate system with a position in the pre-operative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 94 may also be used by the localization module 95 to provide localization data 96 for the robotic system. Device pitch and yaw resulting from articulation commands may be determined during pre-operative calibration. Intra-operatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 20 shows, a number of other input data can be used by the localization module 95. For example, although not shown in FIG. 20, an instrument utilizing shape-sensing fiber can provide shape data that the localization module 95 can use to determine the location and shape of the instrument.

The localization module 95 may use the input data 91-94 in combination(s). In some cases, such a combination may use a probabilistic approach where the localization module 95 assigns a confidence weight to the location determined from each of the input data 91-94. Thus, where the EM data may not be reliable (as may be the case where there is EM interference) the confidence of the location determined by the EM data 93 can be decrease and the localization module 95 may rely more heavily on the vision data 92 and/or the robotic command and kinematics data 94.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Suction Irrigator Grasper Instrument.

Figure 21:
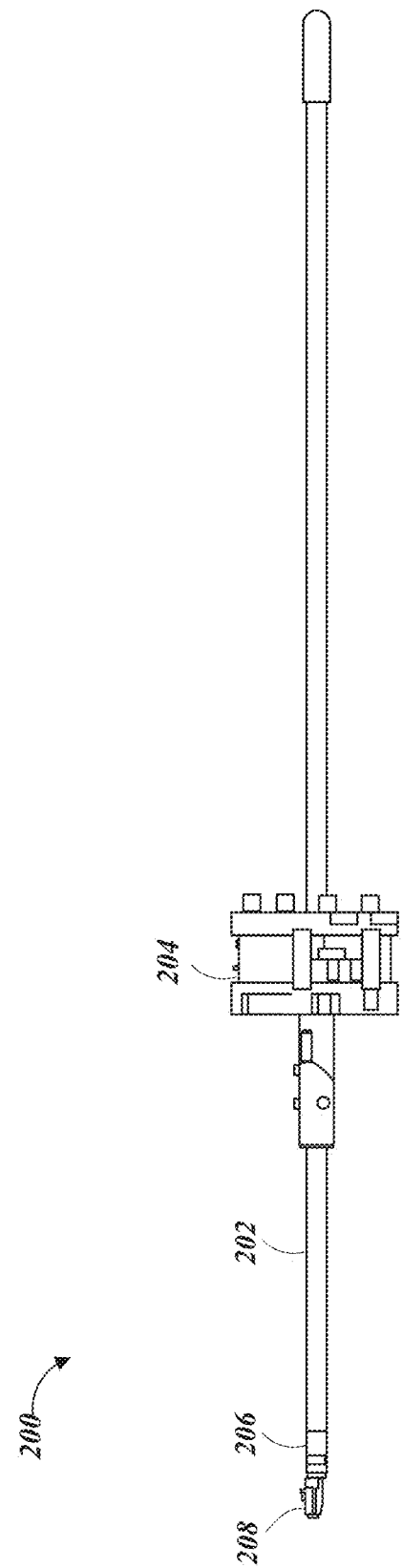
FIG. 21 illustrates a side view of a surgical instrument.
Figure 22C:
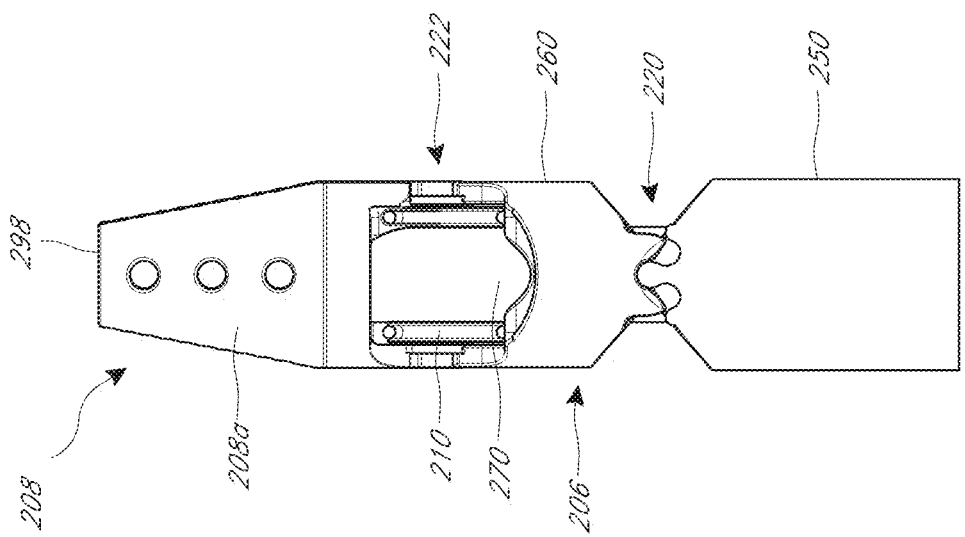
FIG. 22C illustrates a front view of an embodiment of the surgical instrument shown in FIGS. 22A-22B.
Figure 22B:
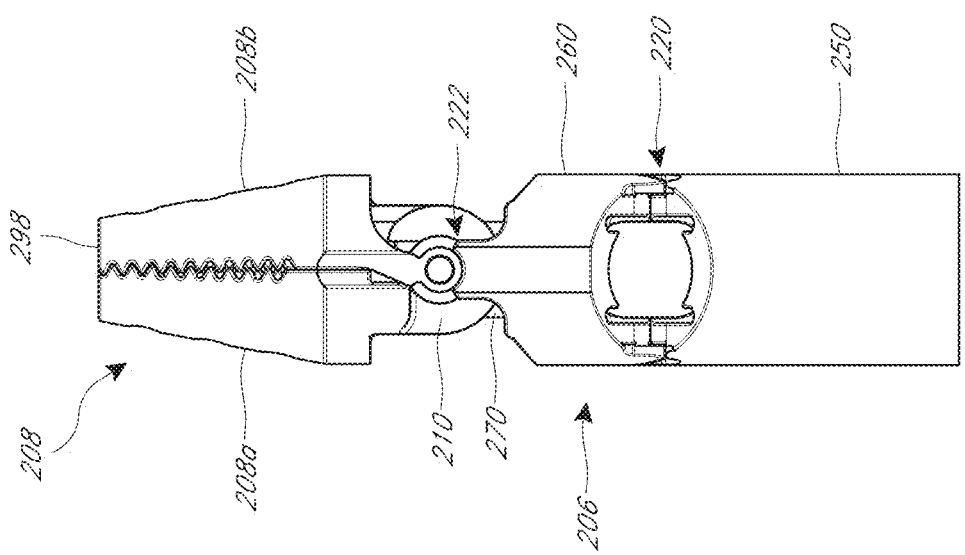
FIG. 22B illustrates a side view of an embodiment of the surgical instrument shown in FIG. 22A.
Figure 22A:
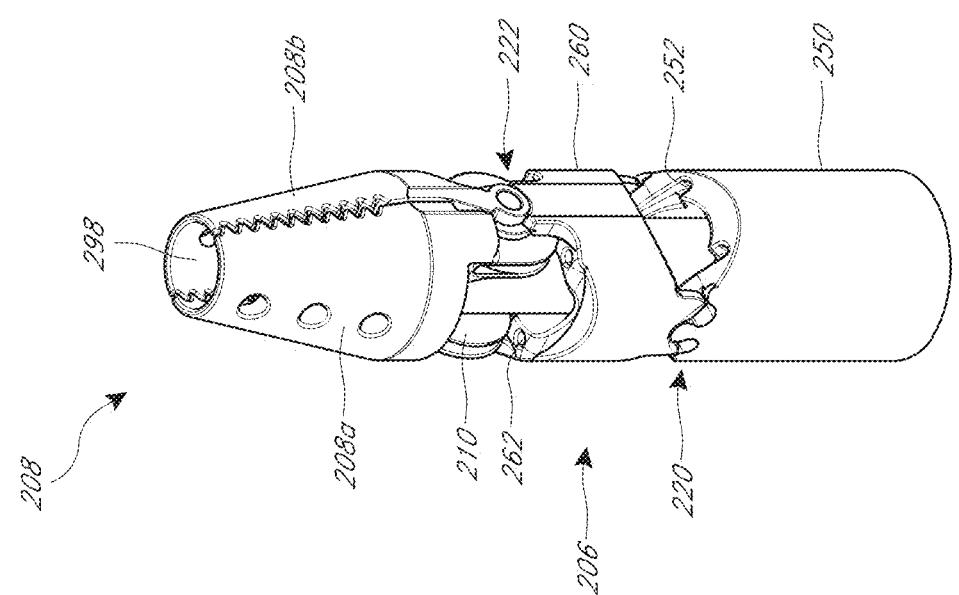
FIG. 22A illustrates a perspective view of an embodiment of a surgical instrument.

FIG. 21 illustrates a side view of an embodiment of a multi-functional surgical instrument 200. The surgical instrument 200 can include an elongate shaft 202, a handle 204, a wrist 206, and a surgical effector 208. FIGS. 22A-C illustrate enlarged views of an example surgical effector 208 of a surgical instrument 200, such as the surgical instrument 200 of FIG. 21.

FIG. 22A illustrates an enlarged perspective view of the end effector or surgical effector 208 of the surgical instrument 200. FIG. 22B illustrates a side view of an embodiment of the surgical effector 208 shown in FIG. 22A. FIG. 22C illustrates a front view of the embodiment of the surgical effector 208 shown in FIGS. 22A-22B.

As shown in FIGS. 22A-C, the surgical wrist 206 can include a proximal clevis 250 and a distal clevis 260. The term "clevis" can include any type of connector that can support a joint, such as a pin or rolling joint. The wrist 206 can be mechanically coupled to the surgical effector 208. The distal clevis 260 can be located distally in relation to the proximal clevis 250. Likewise, the surgical effector 208 can be located distally in relation to the distal clevis 260. The distal clevis 260 may be mechanically coupled to the surgical effector 208 by distal joints 222, which will be described in more detail below. The proximal clevis 250 may be mechanically coupled to the distal clevis 260 by proximal joints 220.

Figure 23A:
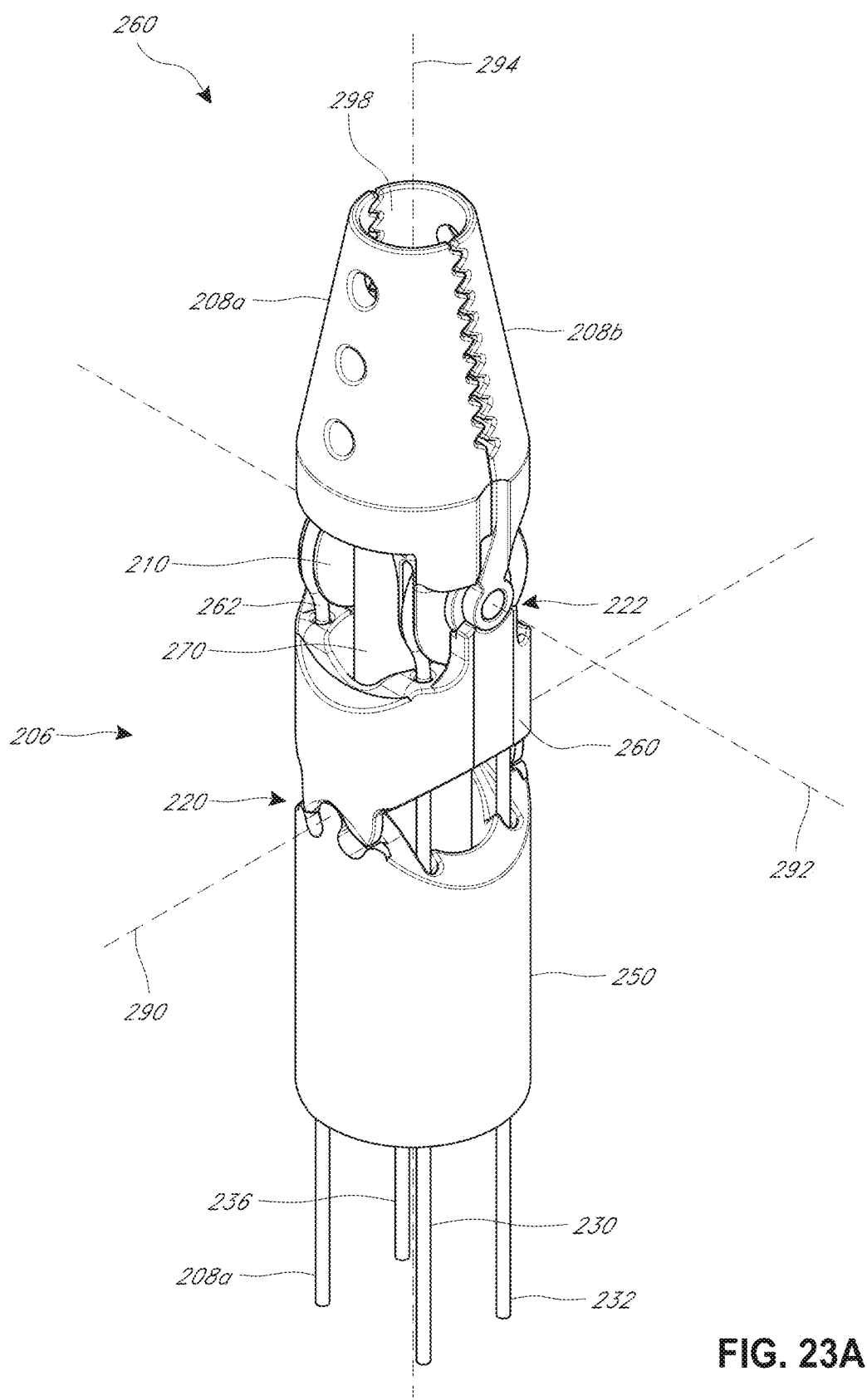
FIG. 23A illustrates a perspective view of the cables of a surgical instrument.

FIG. 23A shows an illustration of the surgical wrist 206 with four cable segments including a first cable segment 230, a second cable segment 232, a third cable segment 234 and a fourth cable segment 236. The surgical effector 208 can actuate in multiple degrees of movement. In the illustrated embodiment, the surgical effector 208 has degrees of movement about a pitch axis 290 and a yaw axis 292 as will be described in more detail below. In some embodiments, the surgical effector 208 can have N+1 cable segments and N degrees of freedom of movement. For example, the surgical effector 208 can be a two degree-of-freedom wrist, pivotable around the pitch axis 290 and the yaw axis 292. In some embodiments, as shown in FIG. 23A, the surgical effector 208 can comprise at least four cable segments 230, 232, 234, 236 to control at least three degrees of freedom, such as, for example, pitch, yaw and grip of the surgical effector 208.

As shown in greater detail in FIG. 23A, the wrist 206 can include four cable segments including the first cable segment 230, the second cable segment 232, the third cable segment 234 and the fourth cable segment 236. In some embodiments, the cable segments can be portions of the same cable. For example, the first cable segment 230 and the second cable segment 232 can be portions of the same cable. Likewise, in some embodiments, the third cable segment 234 and the fourth cable segment 236 can be portions of the same cable. The cable segments 230, 232, 234, 236 can extend along the elongate shaft 202, extend through the proximal clevis 250, and extend through the distal clevis 260. In some embodiments, the cables 230, 232, 234, 236 can pass through elements (e.g. distal clevis 260 and proximal clevis 250) on an axis substantially parallel to a longitudinal axis 294 of the shaft, allowing other elements, especially those with large or limited bending radii, to occupy said space.

Positioning the cable segments 230, 232, 234, 236 through the walls of the wrist 206 allows for additional components to be added to the surgical instrument 200 without increasing the diameter of the instrument 200. For example, a tube 270 for suction and/or irrigation may be positioned within the working lumen of the surgical instrument 200. For example, in certain embodiments, the outer diameter of the surgical instrument 200 can be reduced to less than 6 mm, such as between 5 mm and 6 mm. With reference to FIGS. 26A-26D and 27A-27D, the surgical instrument 200 described herein can also include passages 252, 262 formed in the walls of the wrist 206 to direct the cable segments 230, 232, 234, 236 through the surgical instrument 200. As shown in FIGS. 26A-26D and 27A-27D, the passages 252, 262 can be formed within the walls of the distal clevis 260 and/or the proximal clevis 250 of the instrument 200. These passages can be used instead of pulleys, which can further reduce the size of the surgical instrument.

As shown in FIG. 23A, the proximal clevis 250 can have proximal passages 252 and the distal clevis 260 can have distal passages 262. The proximal passages 252 and distal passages 262 can receive the cable segments 230, 232, 234, 236, as shown in FIG. 23A. Each of the cable segments 230, 232, 234, 236 can be configured to engage the passages 252 and distal passages 262, as shown in FIG. 23A. The cable segments 230, 232, 234, 236 can engage at least a portion of the surgical effector 208. The surgical effector 208 can have effector redirect surfaces 210 configured to engage the cable segments 230, 232, 234, 236, as shown in FIGS. 24A and 25A-25C.

In the embodiment in FIGS. 22A-22C, the proximal clevis 250 can be configured to be mechanically attached to the distal end of the elongate shaft 202 (not shown). The proximal clevis 250 can include proximal passages 252, as shown in FIGS. 23A-C and FIGS. 26A-F, that redirect the cable segments 230, 232, 234, 236 through the proximal clevis 250 towards the distal clevis 260. Similarly, the distal clevis 260 can comprise distal passages 262, as shown in FIGS. 23A-C and FIGS. 27A-F, that redirect the cable segments 230, 232, 234, 236 through the distal clevis 260 towards the surgical effector 208.

The proximal passages 252 of the proximal clevis 250 and the distal passages 262 of the distal clevis 260 can be configured to reduce, or in some cases, prevent tangling or abrasion of the cable segments 230, 232, 234, 236. The proximal passages 252 can also be configured to reduce the amount of friction between the cable segments 230, 232, 234, 236 and the proximal clevis 250. The distal passages 262 can also be configured to reduce the amount of friction between the cable segments 230, 232, 234, 236 and the distal clevis 260. In some embodiments, the proximal passages 252 and/or the distal passages 262 can form holes that extend at least partially through the walls of the proximal clevis 250 and distal clevis 260.

Figure 25B:
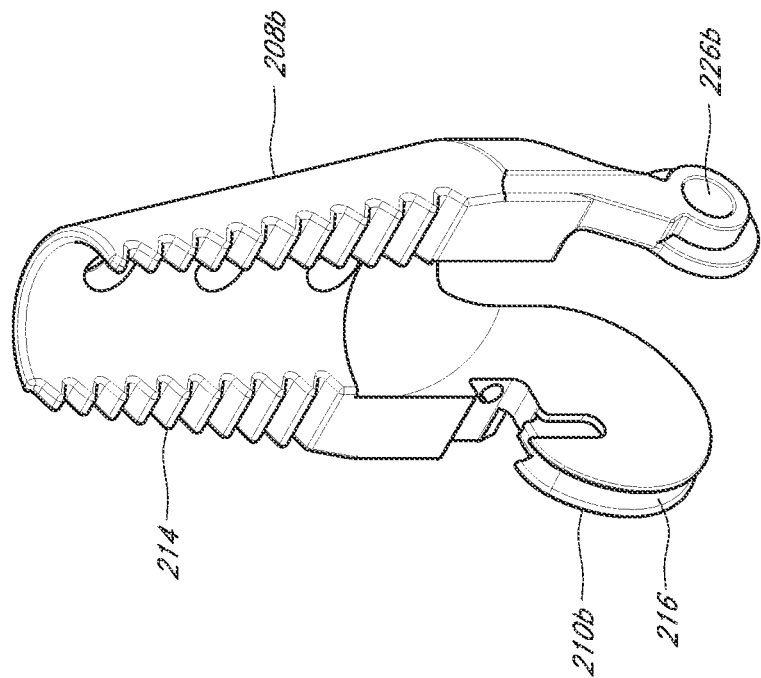
FIG. 25B illustrates another perspective view of a first jaw half of the surgical effector of a surgical instrument of FIG. 24.
Figure 25A:
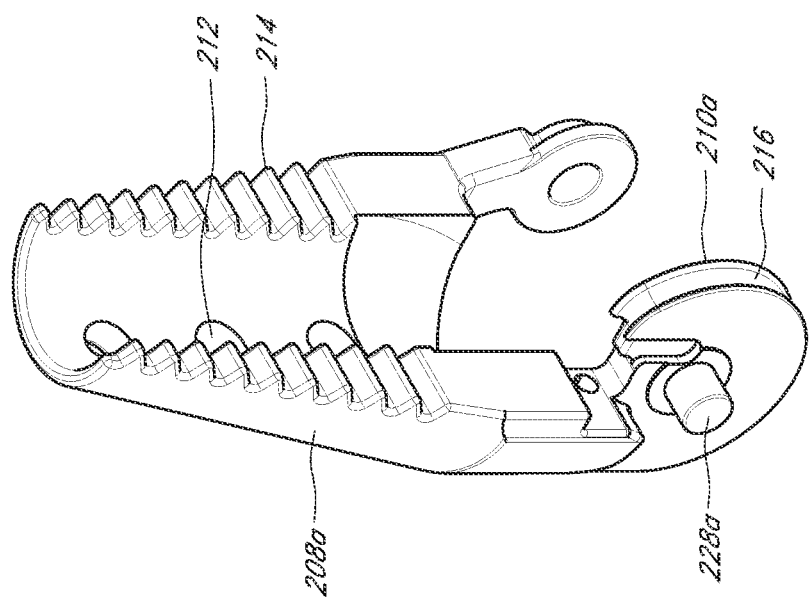
FIG. 25A illustrates a perspective view of a first jaw half of the surgical effector of a surgical instrument of FIG. 24.

As shown in FIG. 23A and FIGS. 25A and 25B, the surgical effector 208 can include a first jaw half 208a and a second jaw half 208b. As shown in FIG. 23A, the first cable segment 230 and the second cable segment 232 can be routed on a first side of the surgical effector 208 on the first jaw half 208a, while the third cable segment 234 and the fourth cable segment 236 can be routed on a second side of the surgical effector 208 on the second jaw half 208b. In such a configuration, the first cable segment 230 and the second cable segment 232 can advantageously engage the effector redirect surfaces 210 of the first jaw half 208a to rotate the first jaw half 208a about the yaw axis 292. The third cable segment 234 and fourth cable segment 236 can advantageously engage effector redirect surfaces 210 of the second jaw half 208b to rotate the second jaw half 208b about the yaw axis 292.

Also shown in FIG. 23A, the first cable segment 230 and the second cable segment 232 can be routed on a first side of the wrist 206, while the third cable segment 234 and the fourth cable segment 236 can be routed on a second side of the wrist 206.

The first cable segment 230 and the second cable segment 232 can be routed on a first side of the distal clevis 260, while the third cable segment 234 and the fourth cable segment 236 can be routed on a second side of the distal clevis 260. The first cable segment 230 and third cable segment 234 can be routed on a first side of the proximal clevis 250, while the second cable segment 232 and fourth cable segment 236 can be routed on a second side of the proximal clevis 250.

FIG. 23B illustrates a perspective view of the surgical instrument 200 of FIGS. 22A-22C, showing rotation of the surgical effector 208 about a yaw axis 292 and rotation of a surgical effector 208 about a pitch axis 290. FIG. 23C illustrates a perspective view of the surgical instrument of FIGS. 22A-22C, showing another rotation of the surgical effector 208 about a yaw axis 292 and rotation of a surgical effector 208 about a pitch axis 290.

In some embodiments, the yaw motion of each jaw half 208a, 208b of the surgical effector 208 can be actuated by a combination of cable segment actuations. For example, the lengthening of cable segment 230 matched with a shortening of cable segment 232 can cause the first jaw half 208a to rotate about the yaw axis 292 about the distal joints 222 in a first direction. In some embodiments, the yaw motion of each half 208a, 208b can be actuated by applying tension (such as pulling) of cable segment 232 matched by a slackening of cable segment 230, which can cause the first jaw 208a to rotate about the yaw axis 292 about the distal joints 222, in a first direction. The second cable segment 232 can have tension applied, such as pulling, to actuate the first jaw half 208a of the surgical effector 208 in a second direction about the yaw axis 292, where the second direction is opposite the first direction.

The second jaw half 208b can be actuated by a combination of cable segment actuations of the third and fourth cable segments 234, 236 in a similar manner as the first jaw half 208a as described above. For example, the third cable segment 234 can have tension applied, such as pulling, to actuate the second jaw half 208b of the surgical effector 208 in a first direction about the yaw axis 292. The fourth cable segment 236 can have tension applied, such as pulling, to actuate the second jaw half 208b of the surgical effector 208 in a second direction about the yaw axis 292, where the second direction is opposite the first direction.

Each of the cable segments 230, 232, 234, 236 can be independently actuated. In some embodiments, each of the cable segments 230, 232, 234, 236 are independent, separate cable segments that are not connected (such that none would be considered as part of the same cable). In other embodiments, the first cable segment 230 and second cable segment 232 may be considered as part of the same cable, while the third cable segment 234 and fourth cable segment 236 may be considered as part of the same cable.

In some embodiments, the term "independently actuated" can mean that the cable segments 230, 232, 234, 236 (e.g., the first cable segment 230 and the third cable segment 234) can move independently and/or at different rates from one another. In some embodiments, the independent cable segments move in equal but opposite amounts about the effector redirect surfaces 210 of the surgical effector 208. In some embodiments, neither of the cables or cable segments that are shared around effector redirect surfaces 210 engage with or intersect with one another. In some embodiments, neither of the cables or cable segments that are shared around a effector redirect surface 210 are directly connected to one another, such as via a crimp.

The cable segments 230, 232, 234, 236 can be further configured so that retracting or advancing a cable segment 230, 232, 234, 236 can actuate the surgical effector 208 to move in a first degree of movement. In one embodiment, shown in FIGS. 23A, 23B, 23C and 24, the surgical effector 208 can have three degrees of movement created by rotation of the about the pitch axis 290 and the yaw axis 292, respectively, as well as the opening and closing of the first and second jaw halves 208a, 208b. The surgical effector 208 of the illustrated embodiment includes a first jaw half 208a and a second jaw half 208b that are operatively connected to the cable segments 230, 232, 234, 236 via effector redirect surfaces 210.

In some embodiments, pitch motion of the surgical effector 208 can be actuated by a combination of cable segment actuations, such as an even lengthening of the third and fourth cable segments 234, 236 matched with an even shortening of the first and second cable segments 230, 232, which can cause the distal clevis 260 to rotate about the pitch axis 290 about the proximal joints 220 in a first direction. In some embodiments, pitch motion of the surgical effector 208 can be actuated by a combination of cable segment actuations, such as applying tension (such as pulling) of cable segments 230, 232, matched with an even slackening of cable segments 234, 236, which can cause the distal clevis 260 to rotate about the pitch axis 290 about the proximal joints 220, in a first direction.

Similarly, pitch motion of the surgical effector 208 can be actuated by a combination of cable segment actuations, such as an even lengthening of cable segments 230, 232 matched with an even shortening of cable segments 234, 236, which can cause the distal clevis 260 to rotate about the pitch axis 290 about the proximal joints 220 in a second direction. In some embodiments, pitch motion of the surgical effector 208 can be actuated by a combination of cable segment actuations, such as applying tension (such as pulling) of cable segments 234, 236 matched with an even slackening of cable segments 230, 232, which can cause the distal clevis 260 to rotate about the pitch axis 290 about the proximal joints 220, in a second direction.

FIGS. 22A-C and FIG. 23A illustrate the surgical effector 208 in an example "neutral" state, i.e., the first yaw angle 282, the second yaw angle 284, and the pitch angle 296 (shown in FIG. 23C) are not offset from the central axis 294, with no cable segments being advanced or retracted. The first yaw angle 282 can be manipulated by advancing/retracting the first cable segment 230 and retracting/advancing the second cable segment 232.

FIG. 23C illustrates the two jaw halves 208a and 208b of the surgical effector 208 rotated at the first yaw angle 282 and the second yaw angle 284 about the yaw axis 292. FIGS. 23B and 23C demonstrate the potential yaw and pitch movement of the surgical effector 208 in accordance with some embodiments.

FIGS. 23B and 23C illustrate the two jaw halves 208a and 208b of the surgical effector 208 rotated at the first yaw angle 282 and the second yaw angle 284 about the yaw axis 292. As shown in FIGS. 23B, the two jaw halves 208a and 208b of the surgical effector 208 can be rotated about the yaw axis 292 at the distal joint 222 together, such that they can be rotated in the same direction. As shown in FIG. 23C, the two jaw halves 208a, 208b of the surgical effector 208 can be rotated about the yaw axis 292 at the distal joints 222 independently, such that the two jaw halves 208a, 208b can be rotated away from each other in opposite directions.

Although the cable segments 230, 232, 234, 236 are not shown in FIGS. 23B and 23C, advancing the first cable 230 and/or retracting the second cable 232 that engages with the effector redirect surfaces 210 of the first jaw half 208a causes the first jaw half 208a to rotate about the yaw axis 292 such that the first yaw angle 282 increases. On the other hand, retracting the first cable segment 230 and/or advancing the second cable segment 232 that engages with the effector redirect surfaces 210 of the first jaw half 208a causes the first jaw half 208a to rotate about the yaw axis 292 such that the first yaw angle 282 decreases.

Similarly, the second yaw angle 284 can be manipulated by advancing/retracting the third cable 234 and retracting/advancing the fourth cable 236. Advancing the third cable 234 and/or retracting the fourth cable 236 that engages with the effector redirect surfaces 210 of the second jaw half 208b causes the second jaw half 208b to rotate about the yaw axis 292 such that the second yaw angle 284 increases. On the other hand, retracting the third cable 234 and/or advancing the fourth cable 236 that engages with the effector redirect surfaces 210 of the second jaw half 208b causes the second jaw half 208b to rotate about the yaw axis 292 such that the second yaw angle 284 decreases.

FIGS. 23B and 23C illustrate the distal clevis 260 of the surgical effector 208 rotated at the pitch angle 296 about the pitch axis 290 at the proximal joints 220.

Although the cable segments 230, 232, 234, 236 are not shown in FIGS. 23B and 23C, the pitch angle 296 of the surgical effector 208 can be manipulated by retracting/advancing the first cable segment 230 and the second cable segment 232 and advancing/retracting the third cable segment 234 and the fourth cable segment 236. On the other hand, advancing both the first cable segment 230 and the second cable segment 232 and retracting both the third cable segment 234 and the fourth cable segment 236 can cause the surgical effector 208 to rotate about the pitch axis 290 such that the pitch angle 296 decreases.

The above description is a configuration controlling the degrees of freedom in which each movement is asynchronous and controlled independently. However, in certain robotic surgical operations the degrees of freedom are changed simultaneously. One skilled in the art will note that simultaneous motion about the three controllable degrees of freedom can be accomplished by a more complex control scheme for advancing and retracting the four cable segments 230, 232, 234, 236. In some embodiments, the four cable segments 230, 232, 234, 236 are formed of a metal, while in other embodiments, the four cable segments 230, 232, 234, 236 are formed of a non-metal. In one embodiment, this control scheme involves a computer-based control system that stores computer program instructions of a master device configured to interpret the motions of the user into corresponding actions of the surgical effector 208 at the surgical site. The computer program may be configured to measure the electric load required to rotate the input controllers to compute the length and/or movement of the cable segments. The computer program may be further configured to compensate for changes in cable segment elasticity, such as if the cables are a polymer, by increasing/decreasing the amount of rotation needed for the input controllers to change the length of a cable segment. The tension may be adjusted by increasing or decreasing the rotation of all the input controllers in coordination. The tension can be increased by simultaneously increasing rotation, and the tension can be decreased by simultaneously decreasing rotation. The computer program may be further configured to maintain a minimum level of tension in the cables. If the tension in any of the cables is sensed to drop below a minimum tension threshold, then the computer program may increase rotation of all input controllers in coordination until the cable tension in all cables is above the minimum tension threshold. If the tension in all of the cables is sensed to rise above a maximum tension threshold, then the computer program may decrease rotation of all input controllers in coordination until the cable tension in any of the cables is below the maximum tension threshold. The computer program may be further configured to recognize the grip strength of the operator based on the load of the motors actuating the input controllers coupled to the cable segments, particularly in a situation where the working members are holding on to an object or are pressed together. More generally, the computer program may be further configured to control the translation and rotation of the surgical instrument via the robotic arm, which in certain embodiments can include an instrument driver 75 with drive outputs 74 as described above with reference to FIG. 16. Torque received from the drive outputs 74 of the instrument driver 75 can be used to separately and/or independently actuate cable segments 230, 232, 234, 236. In certain embodiments, each of the drive outputs 74 can be used to actuate a single cable segment.

A. Suction Irrigator Grasper.

Figure 24A:
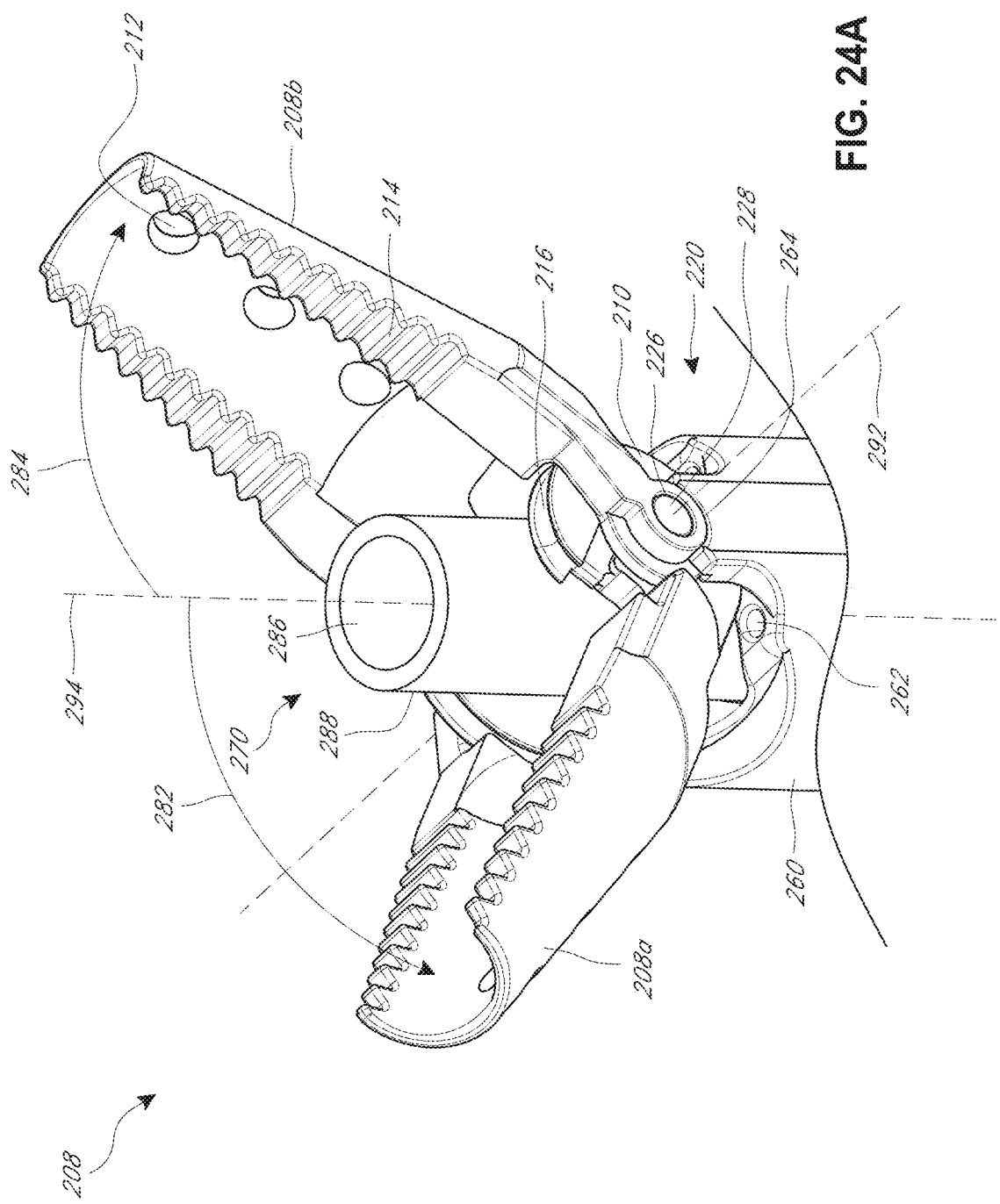
FIG. 24A illustrates a perspective view of the surgical effector of a surgical instrument, showing rotation of two jaw halves about a yaw axis.

FIG. 24A illustrates a perspective view of the surgical effector 208, showing rotation of two jaw halves 208a, 208b about a yaw axis 292. FIG. 25A illustrates a perspective view of a first jaw half 208a of the surgical effector 208. FIG. 25B illustrates a perspective view of a second jaw half 208b of the surgical effector 208. The second jaw half 208b can be a mirror image of the first jaw half 208a.

The instrument 200 can further include a tube 270, as shown in FIGS. 22A-C, 23A-C, 24A and 25C. The tube 270 extends at least partially between the first jaw half 208a and the second jaw half 208b. The tube 270 may extend through the elongate shaft 202, through the proximal clevis 250, through the distal clevis 240, and/or at least partially through the surgical effector 208. In certain embodiments, the outer diameter of the tube 270 can be than less than 6 mm, such as between 4 mm and 5 mm. The tube 270 may be in fluid communication with an irrigation and fluid source. The tube 270 may help form a suction and/or irrigation path through the middle of the instrument 200.

Figure 24B:
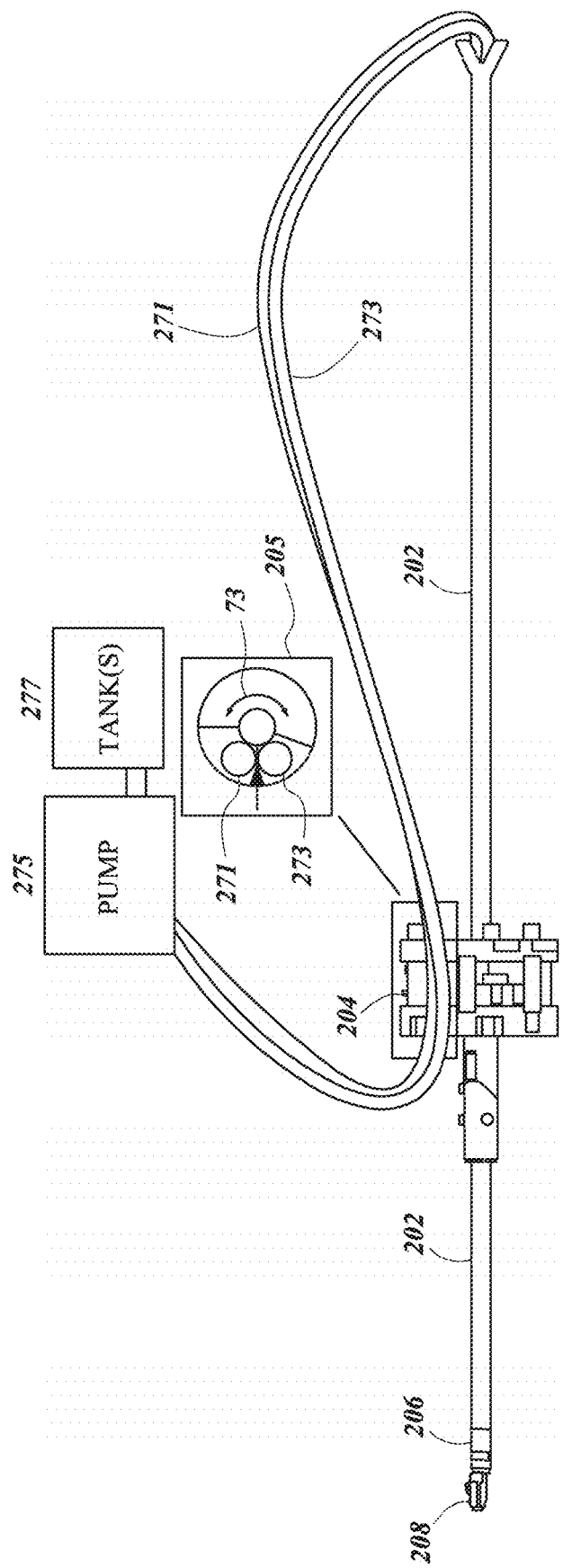
FIG. 24B illustrates a side view of the surgical instrument of FIG. 24A, with the entire shaft and suction/irrigation lines shown.

FIG. 24B illustrates a side view of the surgical instrument of FIG. 24A, with the entire shaft and suction/irrigation lines shown. From this view, one can see how the tube 270 is in fluid communication with both a liquid/irrigation line 271 and a suction line 273 at its proximal most end. A pump 275 can couple the liquid/irrigation line 271 to a source of liquid that may be in a tank 277 and a suction line 273 to an output tank. In addition, from this view, one can see a cross-section 205 of a portion of the handle 204, which shows one or more inputs that advantageously enable robotic control of the irrigation and suction capabilities of the tube 270. In the present embodiment, the handle 204 includes an input 73 that can be controlled by a drive mechanism 146A (as shown in FIG. 14). The input 73 is capable of clockwise and counter-clockwise rotation (illustrated by the arrow in 205) and operably coupled to a capstan that controls whether the liquid/irrigation line 271 or the suction line 273 is operable. In some embodiments, rotation of the capstan associated with the input 73 in a first direction causes the liquid/irrigation line 271 to be compressed (e.g,. via a pinch valve), thereby enabling suction to take place. Likewise, rotation of the capstan in a second direction causes the suction line 273 to be cut off (e.g., via a pinch valve), thereby enabling irrigation to take place. In other words, in some embodiments, a single input 73 of the handle 204 can advantageously control at least two functions—irrigation and suction—robotically. While the present embodiment pertains to robotic control of the irrigation and suction capabilities of the tube 270, in some embodiments, the instrument can also be detached from a drive mechanism of a robotic arm and used manually.

The tube 270 may have a proximal end (not shown) and a distal end 288. the tube 270 may have a proximal end that terminates at the proximal clevis 250. As best seen in FIG. 24A, the distal end 288 of the tube 270 may extend distally relative to the distal clevis 260 and may extend at least partially through the surgical effector 208. The tube 270 can be secured to the wrist 206 at various points. In some embodiments, the tube 270 may be secured to the distal clevis 260 and/or the proximal clevis 250. In some embodiments, the distal end 288 of the tube 270 may also be secured to the wrist 206. In other embodiments, the distal end 288 of the tube 270 can remain free and loose. The proximal end (not shown) of the tube 270 may be in fluid communication with a suction and/or irrigation source. In some embodiments, the tube may be between 3 and 7 millimeters in length, such as between 4 and 6 millimeters in length.

As shown in FIGS. 22A-C and 23A-B, the first and second jaw halves 208a, 208b can be in a closed position where the two jaw halves 208a, 208b are positioned closely together. The jaw halves 208a, 208b may form a passage 298 when in the closed position. The surgical effector 208 can form a nozzle or passage 298. The first and second jaw halves 208a, 208b need not be completely closed to form a passage 298 in fluid communication with the tube 270.

The tube 270 may have an outlet 286 on the distal end 288 in fluid communication with a passage or lumen 298 formed by an interior of the first and second jaw halves 208a, 208b. The tube 270 may act as a suction irrigation lumen when the first and second jaw halves 208a, 208b are in the open position, as shown in FIG. 24A and FIG. 23C, and in the closed position, as shown FIGS. 22A-C and FIG. 23B.

Each of the jaw half 208a, 208b may include a series of holes 212 to assist with suction and/or irrigation. The holes 212 can prevent or inhibit the passage 298 formed by the first and second jaw halves 208a, 208b from forming a complete vacuum during suctioning. The advantage is that the holes 212 may prevent tissue from being sucked in, such that the tissue will not be entirely sucked through the tube 270 in communication with the suction source.

The tube 270 may be made of various materials. The tube 270 may be flexible or rigid. In some embodiments, the tube 270 may be independently articulable and in some embodiments can be coupled to one or more control cables. In other embodiments, the tube 270 may not be independently articulable, such that the tube 270 follows the articulation of the wrist 206 and/or surgical effector 208. For example, as shown in FIGS. 23B and 23C, as the surgical effector 208, the distal clevis 260, and/or the proximal clevis 250 may bend or rotate, the tube 270 may bend to follow the direction of the surgical effector 208, the distal clevis 260, and/or the proximal clevis 250. In some embodiments, some portions of the tube 270 may be pinched by the surgical effector 208.

The surgical effector 208 can also act as a grasper or gripper. As previously discussed, the first and second jaw halves 208a, 208b may rotate towards each other or away from each other, between the opened and closed position, or may be moved or rotated together in the same direction. The first and second jaw halves 208a, 208b may be rotated, as described previously, between the open position, as shown in FIG. 23C and 24A, and the closed position, as shown in FIGS. 22A-C and FIG. 23B. As shown in FIGS. 23C and 24A, the first and second jaw halves 208a, 208b can be in an open position where the distal ends of the two jaw halves 208a, 208b are separated from each other or are positioned away from each other. The first and second jaw halves 208a, 208b in the open position may be positioned around tissue to receive tissue within a patient. The first and second jaw halves 208a, 208b may be rotated about the yaw axis 292 in a closed position where the first and second jaw halves 208a, 208b are configured to clamp tissue to grasp or grip tissue within a patient. The first and second jaw halves 208a, 208b need not be completely closed to grip the tissue, when tissue is positioned between two jaw halves 208a, 208b.

As best shown in FIGS. 24A, and 25A-B, each of the first and second jaw halves 208a, 208b may have ridges or teeth 214 positioned on an interior face of the first and second jaw halves 208a, 208b. The teeth 214 may be capable of complementary engagement. For example, the first and second jaw halves 208a, 208b may have teeth 214 that interdigitate or intermesh with each other. The structure and complementary engagement of the teeth 214 may minimize the profile of the teeth 214 and/or the jaw halves 208a, 208b. The teeth 214 may serve to easily grip the tissue within a patient. In some embodiments, the teeth 214 are pyramidal, saw tooth, or other structures. Furthermore, the teeth 214 may be intermeshed with one another such that the first and second jaw halves 208a, 208b may form a nozzle for the suction and irrigation, as described previously.

Figure 25C:
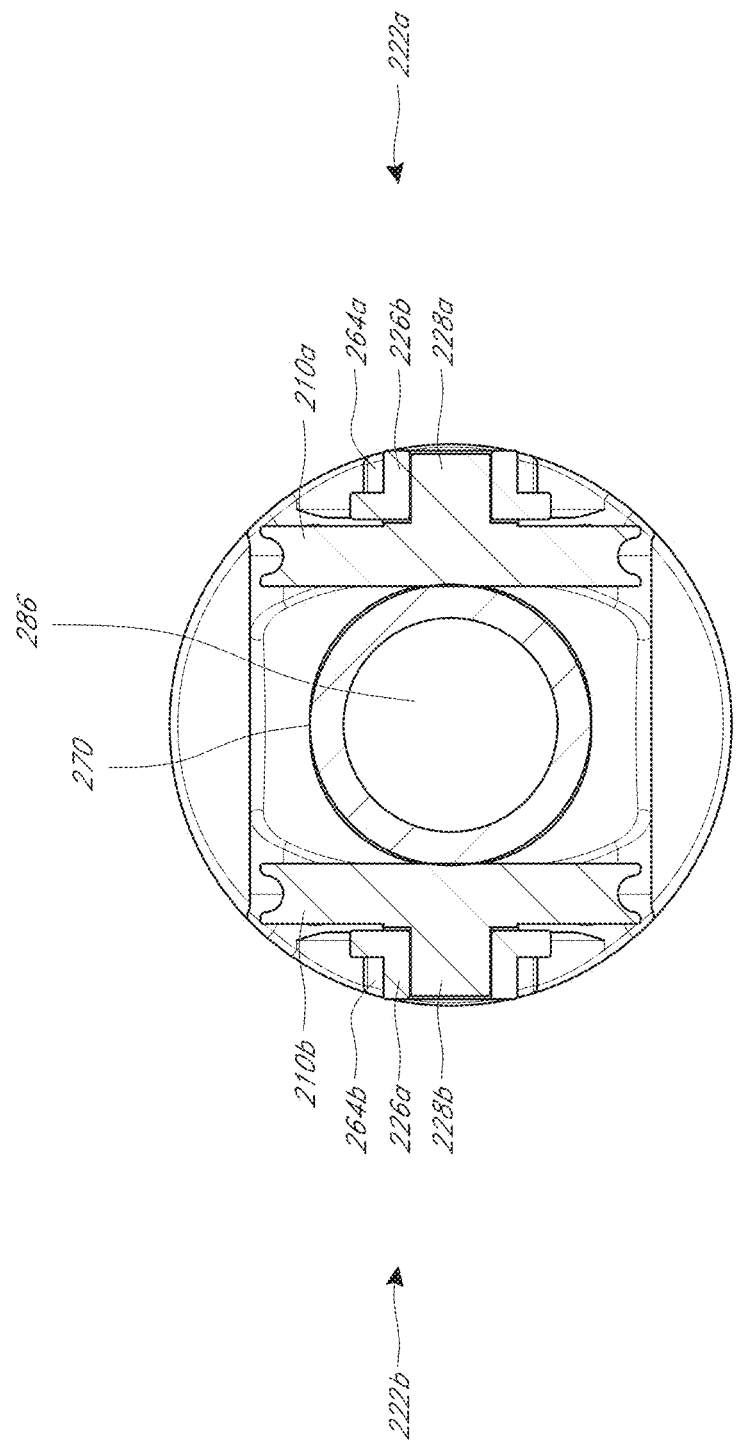
FIG. 25C illustrates a cross sectional view of the connection of a surgical effector and distal clevis of FIG. 24.

FIGS. 25A and 25B illustrate the first jaw half 208a of the surgical effector 208. The second half 208b may be a mirror image of the first jaw half 208a. FIG. 25C illustrates a cross sectional view of connection of a surgical effector 208 and distal clevis 260 of FIGS. 22A-24A at the distal joints 222a, 222b.

The proximal end of each jaw half 208a, 208b 208a, 208b may have a pin 228a on one side and an annular pin 226 on a second side. Each of the first jaw and the second jaw half 208a, 208b may have a pin 228a, 228b to allow pivoting about a yaw axis 292. Each of the first jaw and the second jaw halves 208a, 208b may have an annular pin 226a, 226b, which may each have a hole configured to receive the pin 228a, 228b of the other jaw half 208a, 208b. For example, the first pin 228a of the first jaw half 208a may be inserted into and extend through an opening of the second annular pin 226b of the second jaw half 208b. Similarly, the second pin 228b of the second jaw half 208 may be inserted into and extend through the first annular pin 226a of the first jaw half 208a.

In some embodiments, the annular pins 226a, 226b of the jaw halves 208a, 208b may include holes or openings through a distal wall of the jaw halves 208a, 208b. The annular pins 226a, 226b of the jaw halves 208a, 208b may be shaped and configured to receive the pins 228a, 228b of the jaw halves 208a, 208b. The first jaw and the second jaw 208a, 208b interlock with each other to form pivot pin joints 218a, 218b positioned on the both sides of the surgical effector 208. The pivot pin structure couples the first jaw 208a and the second jaw 208b.

B. Distal Joints and Distal Clevis.

As shown in FIGS. 22A-24A, the distal joints 222 may be formed by the intersection or connection of the surgical effector 208 and distal clevis 260. The distal joints 222 may be positioned on the sides of the instrument 200. The distal clevis 260 forms in part distal joints 222 about which the first and second jaw halves 208a, 208b can rotate. Similarly, the proximal clevis forms in part proximal joints 220 about which the wrist 206 can rotate with respect to the elongate shaft 202, which will be discussed more below. The distal joints 222 may be a different type of joint from the proximal joints 220, which will also be discussed more below. For example, the distal joints 222 may be pin joints and the proximal joints 220 may be rolling joints. By providing different types of joints, the instrument can be provided with different advantages along its length. For example, as discussed below, the distal joints 222 are designed as pin joints that can provide additional space for the inner tube 270 at a distal region of the instrument.

Figure 26A:
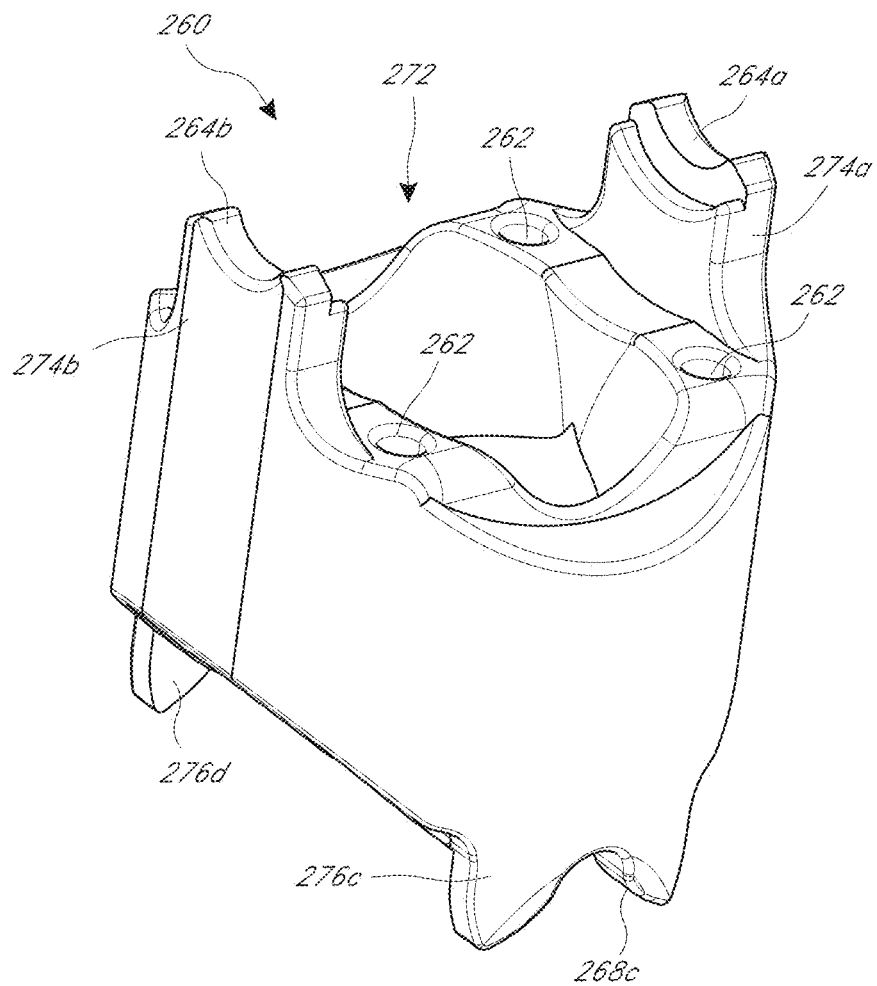
FIG. 26A illustrates a top, perspective view of the a distal clevis of a wrist of a surgical instrument.
Figure 26B:
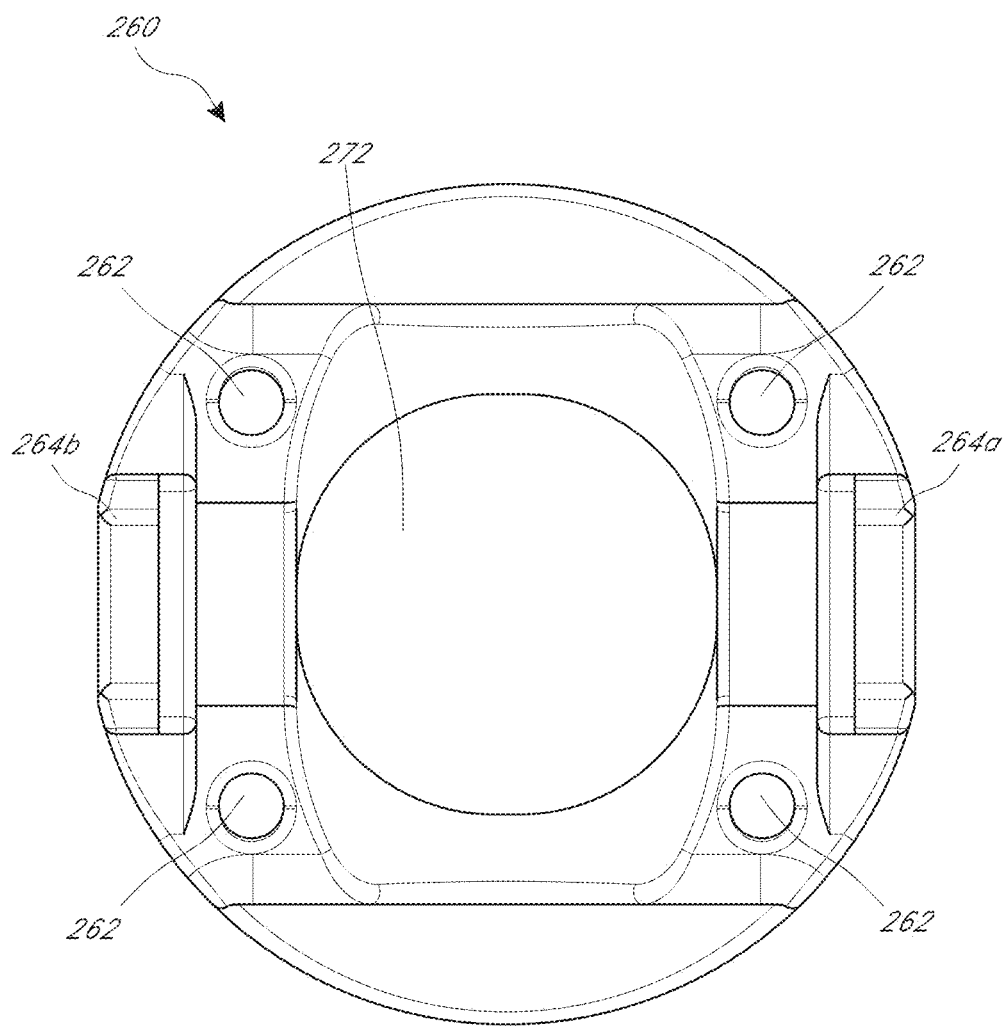
FIG. 26B illustrates a top view of a distal clevis of FIG. 26A.
Figure 26C:
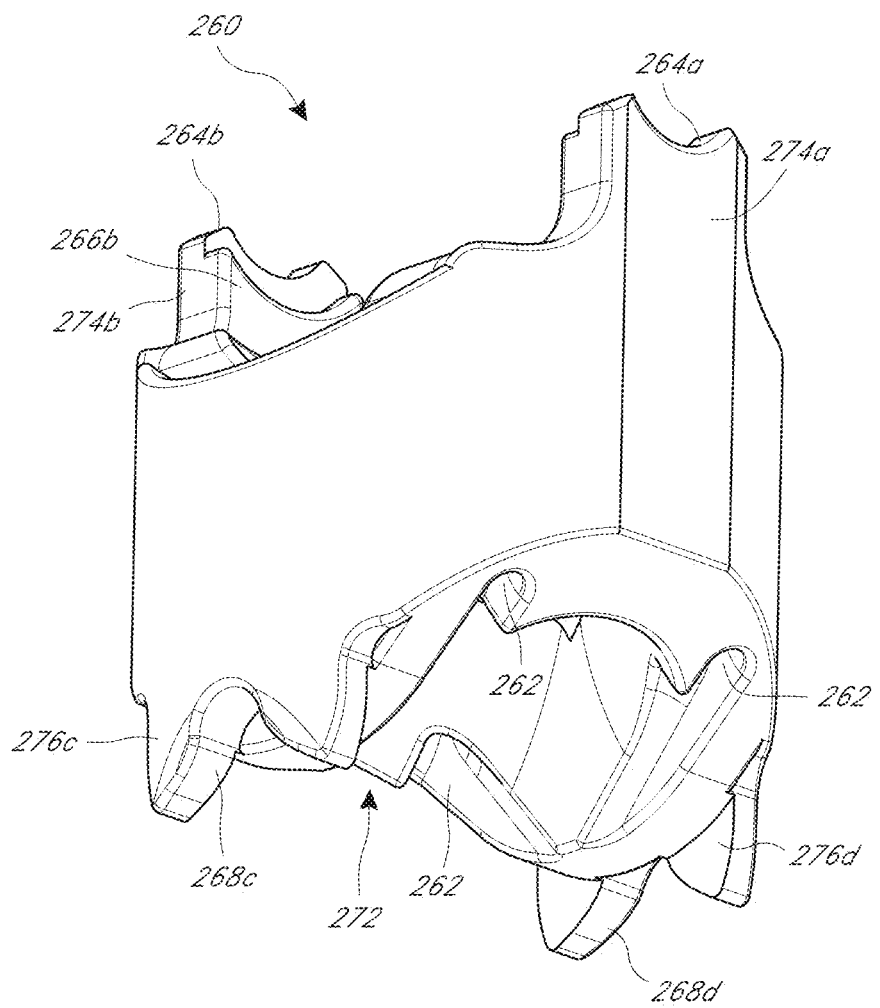
FIG. 26C illustrates a bottom, perspective view of a distal clevis of FIG. 26A.
Figure 26D:
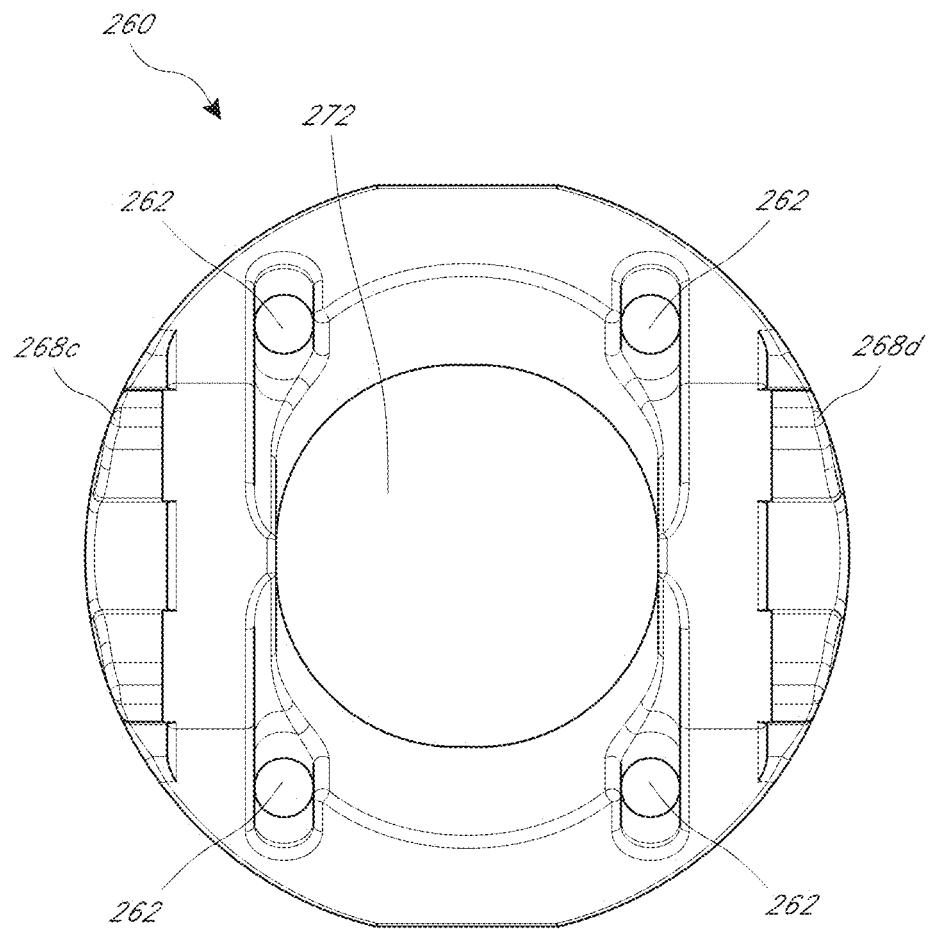
FIG. 26D illustrates a bottom view of a distal clevis of FIG. 26A.
Figure 26E:
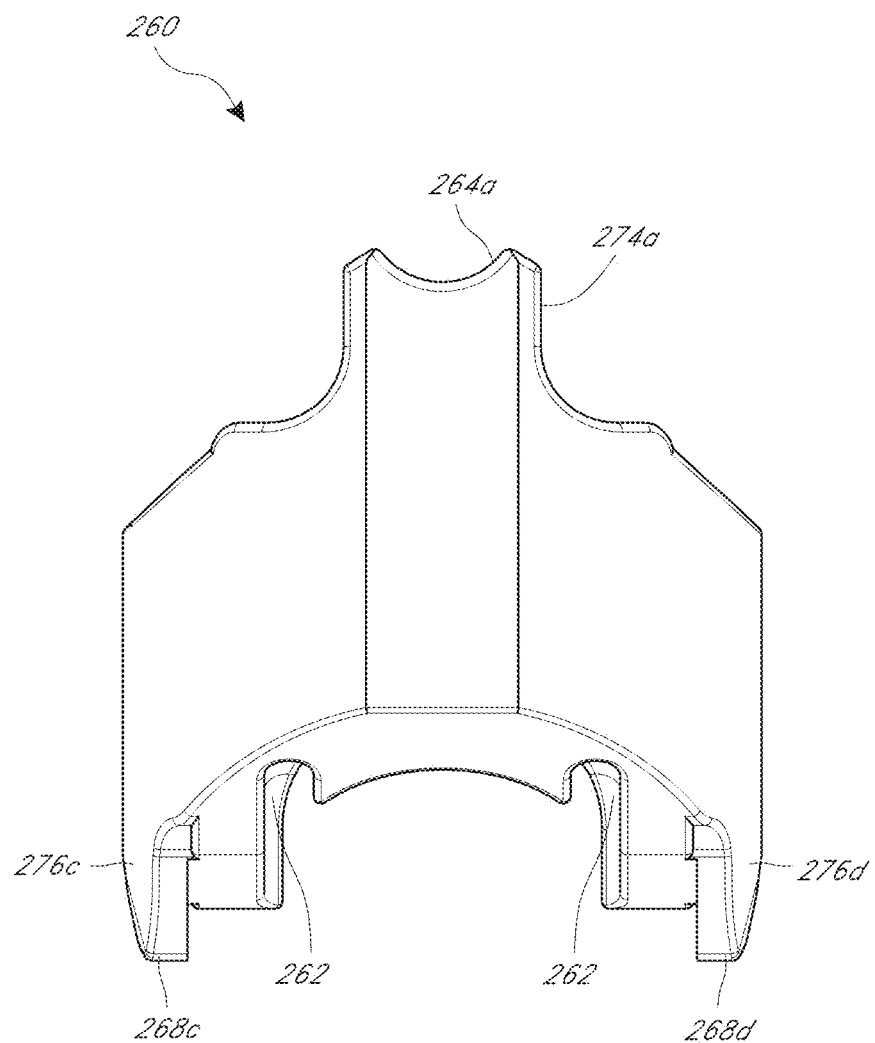
FIG. 26E illustrates a side view of a distal clevis of FIG. 26A.
Figure 26F:
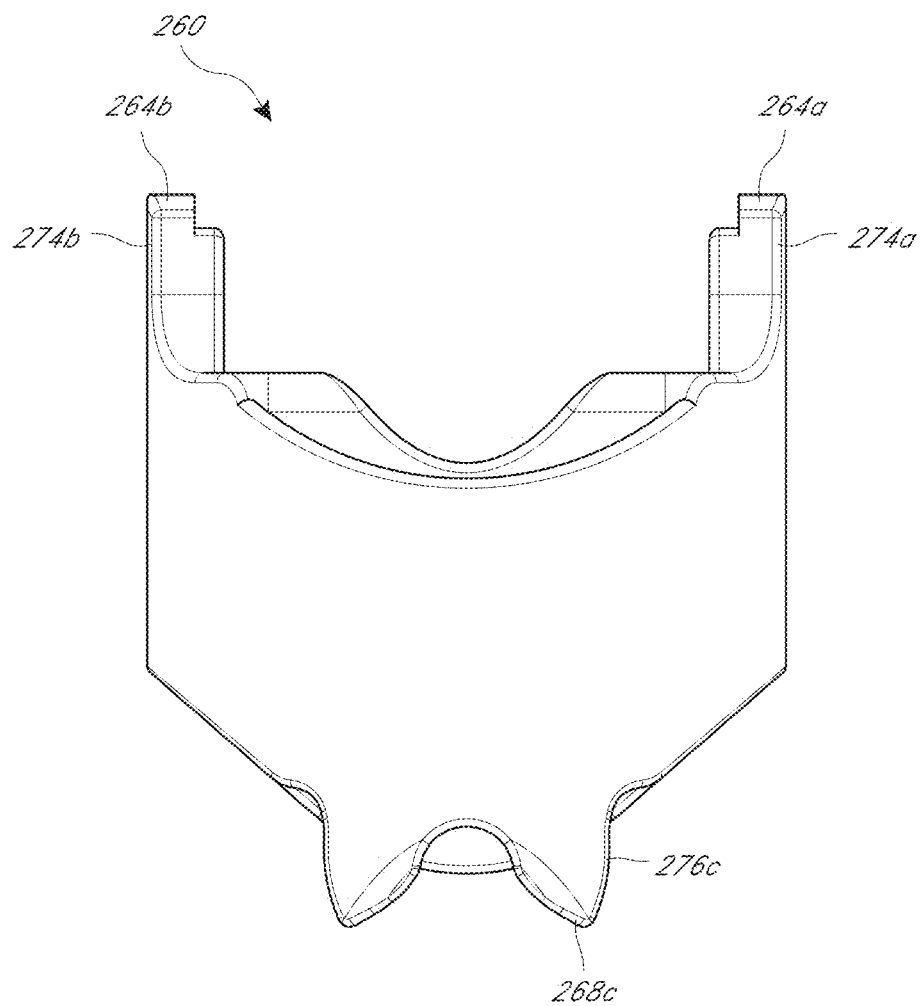
FIG. 26F illustrates a side view of a distal clevis of FIG. 26A.

FIG. 26A shows a top/distal face perspective view of an embodiment of the distal clevis 260. FIG. 26B illustrates the distal face of the distal clevis 260. FIG. 26C illustrates the bottom/proximal face, perspective view of the distal clevis 260. FIG. 26D illustrates the proximal face of the distal clevis 260. FIG. 26E illustrates a side view of the distal clevis 260. FIG. 26F illustrates a side view of the distal clevis 260. As best seen in FIGS. 26A-F, the distal clevis 260 can include two distal arms 274a, 274b and distal passages 262. The two distal arms 274a, 274b can extend distally from side portions of the distal clevis 260 towards the surgical effector 208. Each arm 274 may include distal recesses 264a, 264b on the upper or distal surfaces of each distal arm 274a, 274b. The distal clevis 260 may have distal recesses 264a, 264b formed on the upper or distal surfaces of the distal clevis 260. The distal recesses 264a, 264b may be curved surfaces, openings, or recesses configured to receive pivot pin joints 218a, 218b, which are formed by the interlocked jaw halves 208a, 208b of the surgical effector 208.

The pivot pin joints 218a, 218b of the surgical effector 208 may be positioned within or on the distal recesses 264a, 264b of the distal clevis 260 to form distal joints 222 on either side of the instrument 200. The distal recesses 264a, 264b may be curved surfaces to support at least one pivot axis, such as the yaw axis 292.

The distal recesses 264a, 264b may be cup-shaped or u-shaped. The distal recesses 264a, 264b may be openings shaped to receive the pivot pin joints 218a, 218b of the surgical effector 208, as described previously. The distal recesses 264a, 264b may be configured to define a rotation axis at the distal joints 222. In some embodiments, the rotation axis associated with the distal clevis 260 and the distal joints 222 can be a yaw axis 292, as shown in FIGS. 23A-B and FIGS. 24A-25B.

As shown in FIGS. 24A and 25C, the proximal joints 220 may be partial pin joints. The pivot pin joints 218a, 218b may rest on or within the distal recesses 264a, 264b to form proximal joints 220. Each side of the instrument 200 may therefore have nesting joints or coaxial joints where the pin 228 is received by the annular pin 226 to form a pivot pin joint 218, which in turn acts as pin received by the distal recesses 264a, 264b to form a proximal joint 220. As shown in FIG. 25C, the first pin 228a of the first jaw half 208a is received by the annular pin 226b of the second jaw half 208b to form a first pivot pin joint 218a, which in turn acts as a pin that is received by the distal recess 264a of the distal clevis 260. The first pin 228a of the first jaw half 208a received by the second annular pin 226b of the second jaw half 208b may be the a pivot pin that is pivotably supported within the distal recess 264a, which may be a cup shaped opening. Similarly, the second pin 228b of the second jaw half 208b received by the annular pin 226a of the first jaw half 208a that is pivotably supported within the distal recess 264b, which may be a cup shaped opening.

In order to maintain the jaw halves 208a, 208b of the surgical effector 208 on the distal recesses 264a, 264b, tension in the cable segments (not shown in FIG. 24A) attached to the surgical effector redirect surfaces 210 on the jaw halves 208a, 208b help to hold the jaw halves 208a, 208b in the distal recesses 264a, 264b. The jaw halves 208a, 208b are attached to the distal clevis 260 in this manner so that the jaw halves 208a, 208b are supported on both sides of the distal clevis 260 while also keeping the center of the instrument 200 open for the flexible irrigation suction tube 270.

By allowing the jaw halves 208a, 208b to reside on the distal recesses 264a, 264b, this helps to conserve internal space and volume, as the distal clevis 260 does not need to go on the outside of the pivot pin joints 218a, 218b (as shown in FIG. 25C). This advantageously helps to provide internal space for the tube 270, which can have an outer diameter less than 6 mm, such as 4 mm to 5 mm. This configuration allows the cable segments to operate towards the outer diameter of the instrument 200 and allows the center opening 272 of the distal clevis 260 to remain clear and open for the tube 270.

With continued reference to FIGS. 26A-F, the distal clevis 260 can include two proximal arms 276c, 276d. The two proximal arms 276c, 276d can extend proximally from front and back portions of the distal clevis 260 towards the proximal clevis (not shown). Each proximal arm 276c, 276d may include proximal surfaces 268c, 268d on the bottom or proximal end of each proximal arm 276c, 276d. The distal clevis 260 may have proximal surfaces 268c, 268d formed on the bottom or proximal end of the distal clevis 260. The proximal surfaces 268c, 268d may be a curved surface, a rolling surface, an opening, or recess. The proximal surfaces 268c, 268d may be configured to engage with the proximal clevis 250.

The proximal surfaces 268c, 268d may be configured toenable a rotation axis at the proximal joints 220. In some embodiments, the rotation axis associated with the proximal clevis 250 and the distal clevis 260 can be the pitch axis 290, as shown in FIGS. 23A-B and FIGS. 24A-25B.

The distal clevis 260 may be open or hollow with a central opening 272 that may be positioned and configured such that an elongate rod or tube 270 can be inserted into the opening 272.

As discussed previously and as shown in FIG. 23A, the distal passages 262 may receive cables 230, 232, 234, 236. As shown in FIG. 23A, the cable segments 230, 232, 234, 236 extend through the distal clevis 260 toward the proximal clevis 250.

As shown in FIGS. 26A-F, the distal passages 262 may be positioned within the walls of the distal clevis 260, which allows a space for the opening 272. The distal passages 262 can include one or more surfaces extending about or around the opening 272 extending through a bottom portion or proximal end of the distal clevis 260, as shown in FIGS. 26C-26D. In some embodiments, the distal passages 262 are part of one or more surfaces that form a perimeter of the opening 272 of the distal clevis 260. The distal passages 262 can be angled, curved or sloped such that they can reduce friction between the cable segments (not shown in FIGS. 26A-F) and the distal clevis 260 when the cable segments are retracted or advanced to actuate the surgical effector 208 as described above. In some embodiments, the distal passages 262 are configured to increase cable life by maximizing a radius of curvature. The distal passages 262 can also be configured to prevent the cable segments from tangling or twisting. In some embodiments, the distal passages 262 can comprise of at least one moveable component such as a rotatable ball or surface configured to engage the cable segments. In some embodiments, the cable segments can be configured to engage at least a portion of the distal passages 262. In some embodiments, the cable segments can be configured to engage the entire portion of distal passages 262. In some embodiments, the distal passages 262 of the distal clevis 260 may be coated with a material to reduce friction between the distal passages 262 and the cable segments. As shown in FIGS. 26A-F, the distal passages 262 may extend through the distal clevis 260, from the distal end to the proximal end of the distal clevis 260.

As previously discussed, FIG. 23A illustrates an embodiment of a configuration of the cable segments 230, 232, 234, 236 after extending through the distal clevis 260 and the distal passages 262. After extending through the distal passages 262, the cable segments extend around the effector redirect surfaces 210 of the surgical effector 208. In some embodiments, the cable segments actively engage at least a portion of a plurality of grooves 216 of the surgical effector surfaces 210, as shown in FIG. 23A.

In some embodiments, the cable segments actively engage the entire portion of the plurality of grooves 216 of the surgical effector surfaces 210. As shown in FIGS. 23A, 24A, and 25A-B, each of the plurality of grooves 216 of the surgical effector surfaces 210 can be configured to engage two cable segments. For example, in the embodiment shown in FIG. 23A, the first cable segment 230 and the second cable segment 232 engage the surgical effector surfaces 210 of the first jaw 208a, while the third cable segment 234 and the fourth cable segment 236 engage the surgical effector surfaces 210 of the second jaw 208b. In some embodiments, the cable segments 230, 232, 234, 236 can be configured such that they do not intersect one another.

The cable segments 230, 232, 234, 236 can be further configured so that retracting or advancing a cable segment extending about a first side of the first jaw half 208a operatively coupled to the first jaw half 208a actuates the first jaw half 208a in a first direction of movement, and advancing or retracting a second cable segment extending about a second side of the first jaw half 208b actuates the first jaw half 208a in a second direction of movement. The cable segments 230, 232, 234, 236 can be further configured to engage with the second jaw half 208b and actuate the second jaw half 208b in a similar manner as the first jaw half 208a. In some embodiments, the first jaw half 208a may be actuated by the first cable segment 230 and the second cable segment 232. In some embodiments, the second jaw half 208b may be actuated by the third cable segment 234 and the fourth cable segment 236.

C. Proximal Joints and Proximal Clevis.

Figure 27A:
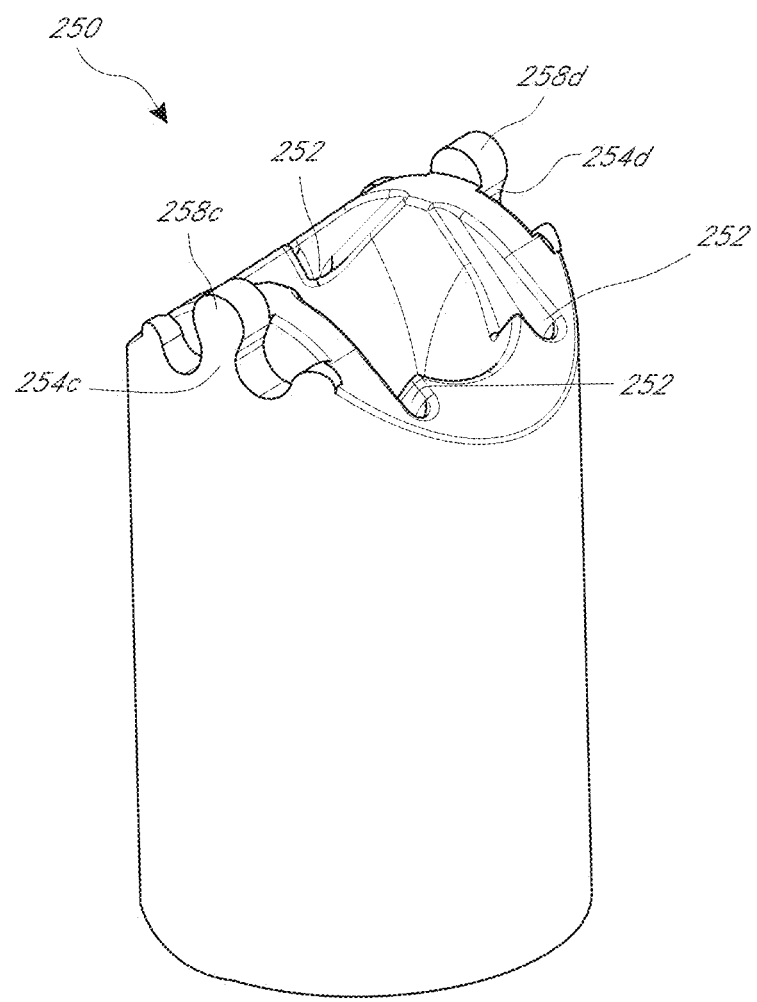
FIG. 27A illustrates a top, perspective view of the a proximal clevis of a wrist of a surgical instrument.
Figure 27B:
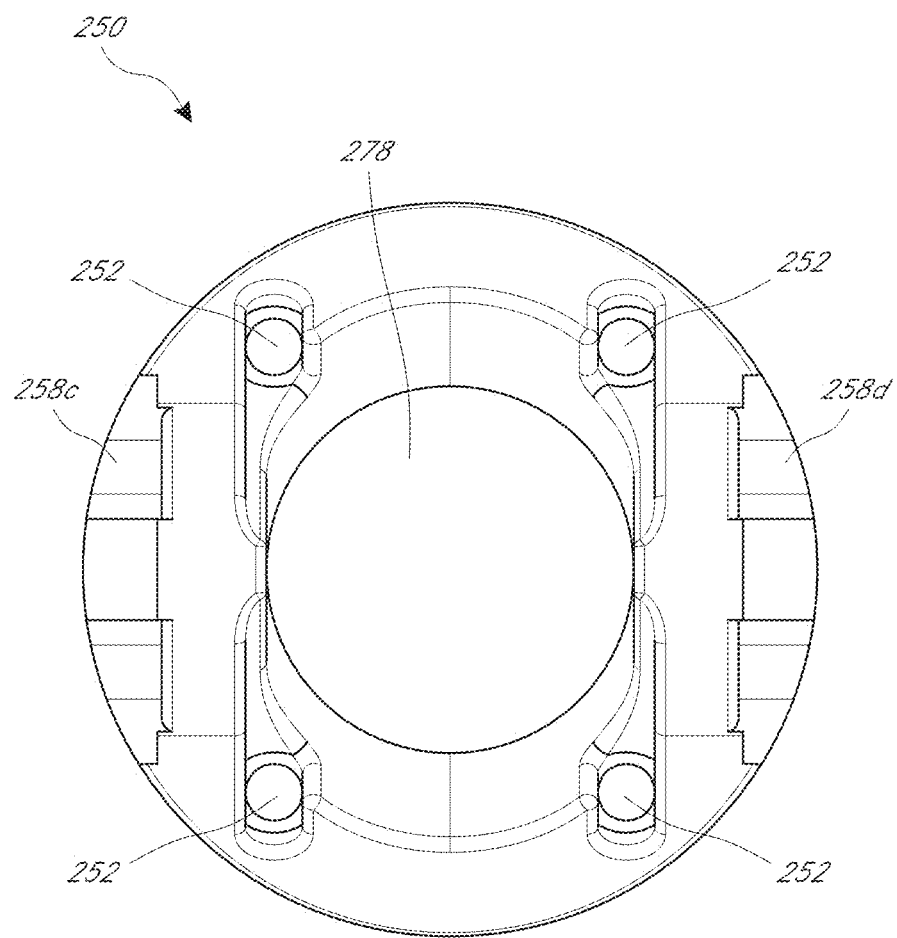
FIG. 27B illustrates a top view of a proximal clevis of FIG. 27A.
Figure 27C:
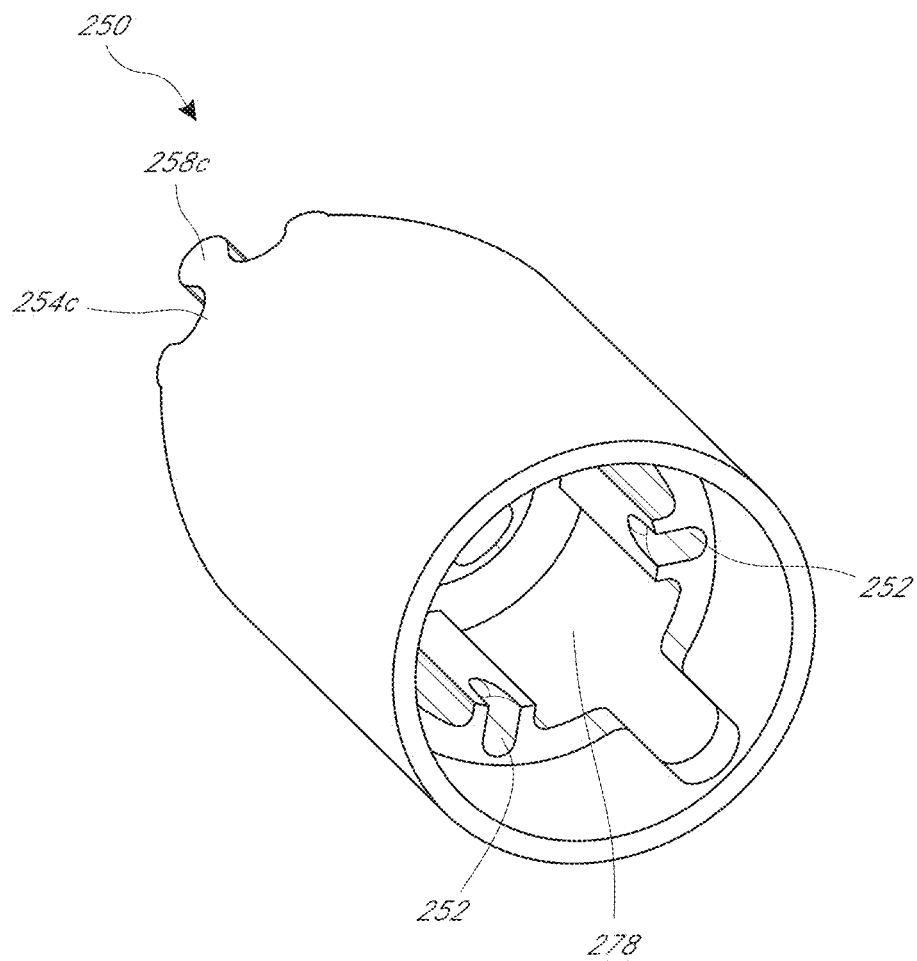
FIG. 27C illustrates a bottom, perspective view of a proximal clevis of FIG. 27A.
Figure 27D:
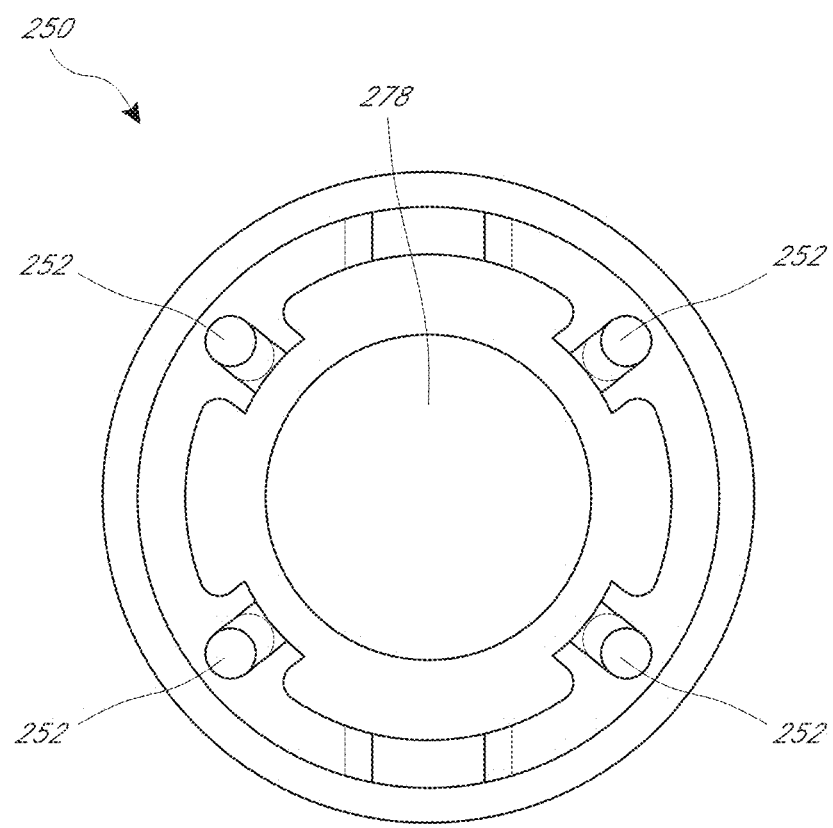
FIG. 27D illustrates a bottom view of a proximal clevis of FIG. 27A.
Figure 27E:
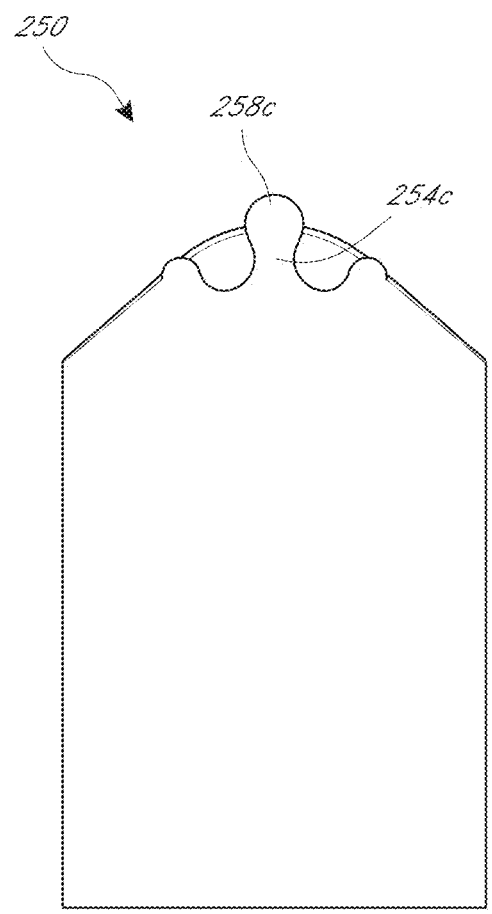
FIG. 27E illustrates a front view of a proximal clevis of FIG. 27A.
Figure 27F:
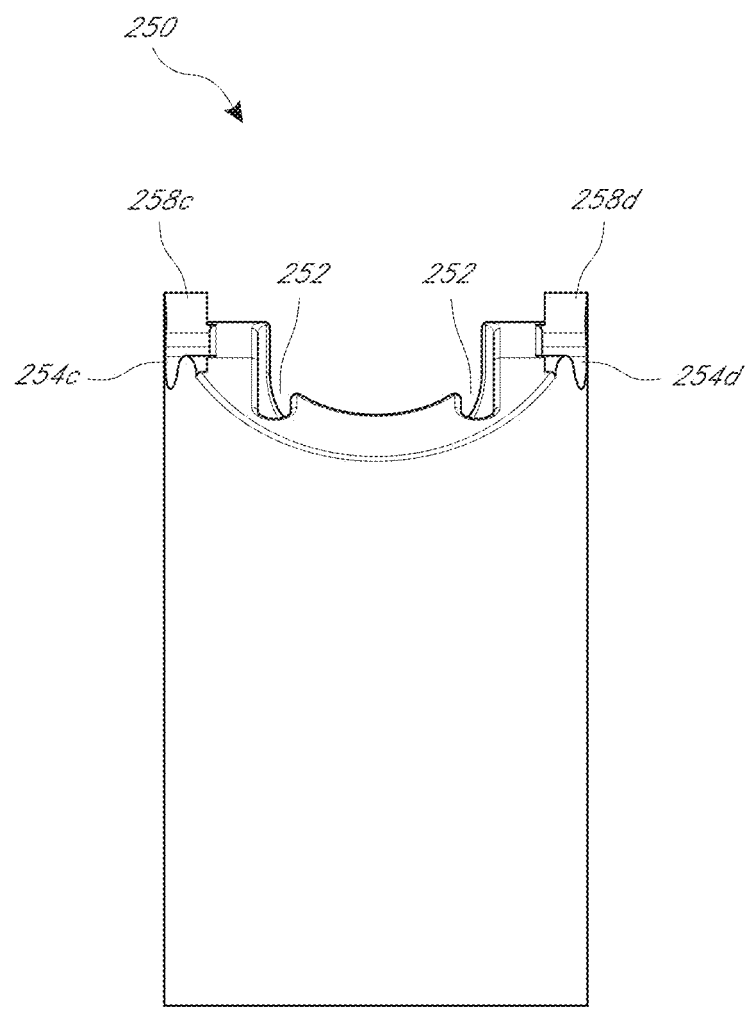
FIG. 27F illustrates a side view of a proximal clevis of FIG. 27A.

FIG. 27A illustrates a distal, perspective view of the proximal clevis of a wrist of a surgical instrument. FIG. 27B illustrates a distal view of the proximal clevis 250. FIG. 27C illustrates a proximal, perspective view of the proximal clevis 250. FIG. 27D illustrates a bottom view of the proximal clevis 250. FIG. 27E illustrates a side view of the proximal clevis 250. FIG. 27F illustrates a front view of the proximal clevis 250. As discussed previously, the proximal clevis forms in part proximal joints 220 about which the wrist 206 can pivot with respect to the elongate shaft 202, which will be discussed more below.

The proximal clevis 250 can include of two distal arms 254c, 254d. The two distal arms 254c, 254d can extend distally from front and back portions of the proximal clevis 250 towards the distal clevis (not shown). Each distal arm 254c, 254d may include distal recesses 264a, 264b on the upper or distal surfaces of each distal arm 254c, 254d. The distal arms 254c, 254d can extend distally from the front and back portions of the proximal clevis 250 towards the distal clevis (not shown). The distal arms 254c, 254d may align with the proximal arms 268c, 268d of the distal clevis 260.

The proximal clevis 250 may have distal surfaces 258c, 258d formed on the upper or distal surfaces of the proximal clevis 250. The distal surfaces 258c, 258d may be a curved surface, rolling surface, or a protrusion configured to engage with the proximal surfaces 268c, 268d of the distal clevis 260. The distal surfaces 258c, 258d may be configured to engage with the distal clevis 260.

The distal surfaces 258c, 258d may be configured to enable a rotation axis at the proximal joints 220. In some embodiments, the rotation axis associated with the proximal clevis 250 and the distal clevis 260 can be a pitch axis 290, as shown in FIGS. 23A-B and FIGS. 24A-25B.

The proximal clevis 250 may be open or hollow with a central opening 278 that may be positioned and configured such that an elongate rod or tube 270 can be inserted into the opening 278.

As discussed previously and as shown in FIG. 23A, the proximal passages 252 may receive cables 230, 232, 234, 236. As shown in FIG. 23A, the cable segments 230, 232, 234, 236 extend through the distal clevis 260 toward the proximal clevis 250.

As shown in FIGS. 27A-F, the proximal passages 252 may be positioned within the walls of the proximal clevis 250, which allows a space for the opening 278. The proximal passages 252 can include one or more surfaces extending about or around the opening 278 extending through a bottom portion or proximal end of the proximal clevis 250, as shown in FIGS. 27C-27D. In some embodiments, the proximal passages 252 are part of one or more surfaces that form a perimeter of the opening 278 of the proximal clevis 250. The proximal passages 252 can be angled, curved or sloped such that they can reduce friction between the cable segments and the proximal clevis 250 when the cable segments are retracted or advanced to actuate the surgical effector 208 as described above. In some embodiments, the proximal passages 252 are configured to increase cable life by maximizing a radius of curvature. The proximal passages 252 can also be configured to prevent the cable segments from tangling or twisting. In some embodiments, the proximal passages 252 can include of at least one moveable component such as a rotatable ball or surface configured to engage the cable segments (not shown). In some embodiments, the cable segments can be configured to engage at least a portion of the proximal passages 252. In some embodiments, the cable segments can be configured to engage the entire portion of proximal passages 252. In some embodiments, the proximal passages 252 of the proximal clevis 250 may be coated with a material to reduce friction between the proximal passages 252 and the cable segments. As shown in FIG. 25B, the proximal passages 252 may extend through the proximal clevis 250, from the distal end to the proximal end of the proximal clevis 250.

As shown in FIGS. 22A-24A, the proximal joints 220 may be formed by the intersection or connection of the distal clevis 260 and the proximal clevis 250. The proximal joints 220 may be positioned on the front and back of the instrument 200. The proximal joints 220 may be formed between the proximal clevis 250 and the distal clevis 260.

In some embodiments, the proximal joints 220 may be rolling joints or cycloidal joints that allows the cable segments to operate towards the outer diameter of the instrument 200 and allows the center opening 272 of the distal clevis 260 and the center opening 278 of the proximal clevis 250 of the instrument 200 to be open for the tube 270.

The proximal joints 220 may be formed by the intersection or connection of the proximal end of the distal clevis 260 with the distal end of the proximal clevis 250.

As previously discussed, the distal clevis 260 may have proximal surfaces 268c, 268d formed on the bottom or proximal end of the distal clevis 260. The proximal surfaces 268c, 268d may be a curved surface, a rolling surface, an opening, or a recess configured to receive or engage with the proximal clevis 250.

As previously discussed, the proximal clevis 250 may have distal surfaces 258c, 258d formed on the top or distal end of the proximal clevis 250. The distal surfaces 258c, 258d may be a curved surface, a rolling surface, or a protrusion configured to be inserted within or engage with the distal clevis 260.

As shown in FIGS. 23B-C, the proximal joints 220 allow the distal clevis 260 to rotate about the pitch axis 290 relative to the proximal clevis 250. The proximal joints 220 allow the distal clevis 260 and/or the wrist 206 to pivot with respect to the proximal clevis 250 and/or the elongate shaft 202.

As described previously and shown in FIG. 23A, the cable segments 230, 232, 234, 236 can be configured to extend through the proximal clevis 250. As described previously, the cable segments 230, 232, 234, 236 can be configured to actively engage at least a portion of a plurality of grooves 216 of the surgical effector surfaces 210.

D. Example Method of Use.

During laparoscopic surgery, surgeons may need a suction/irrigator tool to flush a liquid and/or remove pooling liquid at a surgical site. Often times, multiple tools (e.g., a grasper and a separate suction/irrigator) may be needed. But the use of multiple tools can be undesired due to space and time constraints, the need for an additional incision, the need for an additional assistant, and the cost of an additional tool. As described previously, the surgical instrument 200 provides a multi-functional instrument that can serve as both a grasper and a suction/irrigator. Accordingly, in some embodiments, it can serve at least three functions.

The surgical instrument 200 described above provides a number of advantages over other devices, including allowing a surgeon to quickly reach a surgical site to provide irrigation or clear it of pooling blood. In addition, when compared to manual procedures, the robotically-controlled, multi-functional surgical instrument 200 can reduce the need of having an assistant use a manual suction irrigator in addition to a grasper. Furthermore, the use of the robotically-controlled multi-functional surgical instrument 200 reduces the need for tool exchange.

Figure 28:
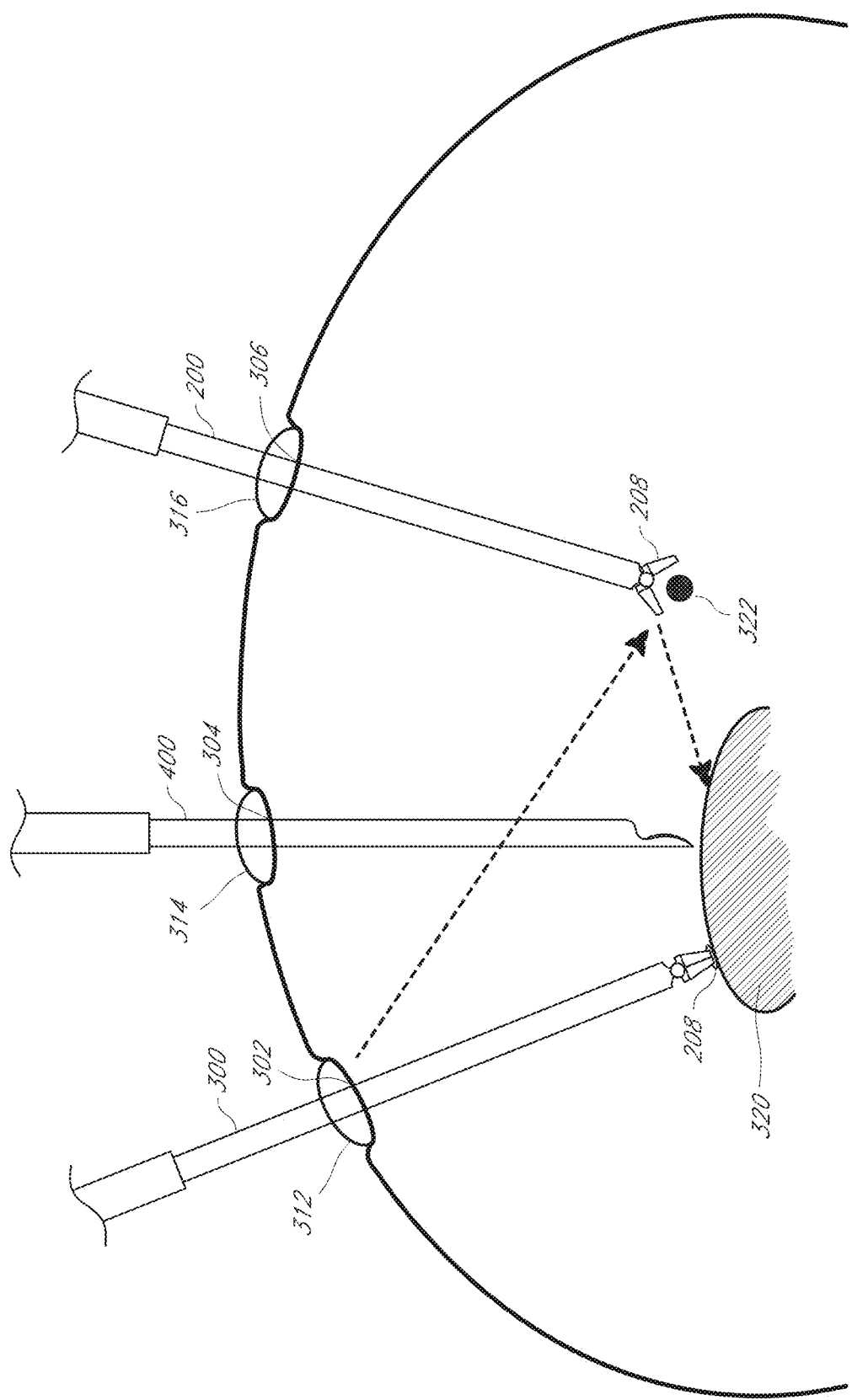
FIG. 28 illustrates a method of use of a surgical instrument at a surgical site.

FIG. 28 illustrates a method of use of a surgical instrument 200 at a surgical site 320. The surgical instrument 200 may include inserting a distal end of the surgical instrument 200 into a patient, using the surgical instrument 200 to grip tissue within the patient, and using the surgical instrument 200 to perform a suction and/or irrigation procedure within the patient.

Another exemplary method of using an surgical instrument 200 described above includes:

a) Forming a first incision 302, a second incision 304, and a third incision 306;

b) Inserting a first cannula 312 through the first incision 302, a second cannula 314 through the second incision 304 and a third cannula 316 through the third incision 306;

c) Inserting a first instrument 300 through the first cannula 312, wherein the first instrument 300 includes a grasper (e.g., a bipolar grasper) for holding tissue at a surgical site 320;

d) Inserting a second instrument 400 through the second cannula 314, wherein the second instrument 400 includes a cutting instrument (e.g., a monopolar curved shear) for performing a procedure at the surgical site 320;

e) Inserting a third instrument 200 through the third cannula 316, wherein the third instrument 200 includes a surgical instrument 200 as described above (e.g., a suction irrigation grasper) for holding adjacent tissue 322 adjacent to the surgical site 320;

f) Detecting a need for suction or irrigation at the surgical site 320;

g) Maneuvering the first instrument 300 such that it holds the adjacent tissue 322 adjacent to the surgical site 320 (denoted by the perforated arrow extending from the first instrument 300 to the adjacent tissue 322);

h) Maneuvering the third surgical instrument 200 such that it performs a suction or irrigation procedure at the surgical site 320 (denoted by the perforated arrow extending from the third instrument 200 to the surgical site 320), wherein each of the first instrument 300, second instrument 400 and third instrument 200 remain docked to their respective cannulas.

Note that the method described above provides a number of advantages. First, as the instruments can be robotically controlled, there is a lesser need for an additional assistant to control a manual suction or irrigation instrument, which may require an additional port. Second, as the instruments all remain docked to their respective cannulas, there is no need to undock and swap instruments, which can be time consuming. During an operation, it can be crucial to get to a site of internal bleeding as quickly as possible (e.g., for vacuuming). The use of a multi-functional instrument 200 such as the suction irrigation grasper helps to get to such a site rapidly and with ease, without needing to swap tools.

3. Implementing Systems and Terminology.

Implementations disclosed herein provide system, methods, and apparatus for robotically-enabled medical systems. Various implementations described herein include robotically-enabled medical systems with a wrist comprising one or more pulleys shared by cable segments.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The robotic motion actuation functions described herein may be stored as one or more instructions on a processor-readable or computer-readable medium. The term "computer-readable medium" refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A multi-functional surgical instrument, comprising:
   an elongate shaft extending between a proximal end and a distal end;
   a wrist extending from the distal end of the elongate shaft, wherein the wrist includes a distal clevis having a first curved surface, wherein the first curved surface defines at least one pivot axis;
   an end effector extending from the pivot axis of the wrist, the end effector comprising a first jaw and a second jaw, the first and second jaw being moveable between an open position in which ends of the first and second jaws are separated from each other and a closed position in which the ends of the first and second jaws are closer to each other as compared to the open position, wherein the end effector further includes a first outer pin and a first inner pin, wherein the first outer pin receives the first inner pin therein to movably connect the first and second jaws together, and wherein the first outer pin is received against the first curved surface such that the end effector is configured to pivot about the at least one pivot axis; and
   a tube extending through the elongate shaft and the wrist, the tube having an outlet in fluid communication with a nozzle cooperatively formed by an interior surface of the first and second jaws when the first and second jaws are in the closed position, wherein each of the first and second jaws are movable relative to the tube.

2. The multi-functional surgical instrument of claim 1, wherein the wrist further comprises a proximal clevis, wherein the distal clevis forms in part a first joint about which the first and second jaw can rotate and the proximal clevis forms a second joint about which the wrist can pivot with respect to the elongate shaft.

3. The multi-functional surgical instrument of claim 2, wherein the first joint is a different type of joint from the second joint.

4. The multi-functional surgical instrument of claim 1, wherein the ends of the first and second jaws define a portion of the nozzle therethrough, in the closed position.

5. The multi-functional surgical instrument of claim 1, wherein the first jaw defines a hole in fluid communication with the nozzle.

6. The multi-functional surgical instrument of claim 1, wherein the distal clevis has a second curved surface further defining the at least one pivot axis, wherein the end effector further includes a second outer pin and a second inner pin, wherein the second outer pin receives the second inner pin therein to movably connect the first and second jaws together, and wherein the second outer pin is received against the second curved surface such that the end effector is configured to pivot about the at least one pivot axis.

7. The multi-functional surgical instrument of claim 6, wherein the first and second outer pins extend along the at least one pivot axis.

8. The multi-functional surgical instrument of claim 7, wherein the first and second inner pins extend along the at least one pivot axis.

9. The multi-functional surgical instrument of claim 8, wherein each of the first and second outer pins and each of the first and second inner pins are coaxial with the at least one pivot axis.

10. The multi-functional surgical instrument of claim 1, wherein the first outer pin and the first inner pin extend along the at least one pivot axis.

11. The multi-functional surgical instrument of claim 10, wherein each of the first outer pin and the first inner pin are coaxial with the at least one pivot axis.

12. A surgical instrument, comprising:
    an elongate shaft extending between a proximal end and a distal end;
    a wrist extending from the distal end of the elongate shaft, the wrist comprising a distal clevis and a proximal clevis, the distal clevis comprising a plurality of distal arms each extending distally from a respective side portion of the distal clevis, wherein each distal arm comprises a distal recess formed by an upper distal surface of the respective distal arm and the distal recess is distally open to form a generally U-shape having an open portion;
    an end effector extending from the wrist, the end effector comprising a first jaw and a second jaw, and at least one pin joint formed between the first jaw and the second jaw, wherein the at least one pin joint is supported by the distal recess; and
    a cable segment extending along the wrist and attached to the end effector, wherein the cable segment is proximally drawn in tension to thereby maintain the at least one pin joint proximally against the distal recess.

13. The surgical instrument of claim 12, wherein the at least one pin joint is formed by a first pin that extends from the first jaw into an opening in the second jaw.

14. The surgical instrument of claim 12, wherein the first jaw and the second jaw rotate relative to each other about the pin joint.

15. The surgical instrument of claim 14, wherein the pin joint collectively rotates relative to the distal recess.

16. The surgical instrument of claim 12, wherein the first jaw and the second jaw are interlocked to form the at least one pin joint.

17. The surgical instrument of claim 12, wherein the at least one pin joint includes a first outer pin and a first inner pin, wherein the first outer pin receives the first inner pin therein to movably connect the first and second jaws together, and wherein the first outer pin is received proximally against the distal recess.

18. A surgical instrument, comprising:
    an elongate shaft extending between a proximal end and a distal end;
    a wrist extending from the distal end of the elongate shaft, the wrist including a distal clevis having a first curved surface, wherein the first curved surface defines a pivot axis; and
    an end effector extending from the wrist, including:
      a first jaw having a first outer pin and a first inner pin, wherein each of the first outer pin and the first pin extend along the pivot axis,
      a second jaw having a first inner pin and a second outer pin, wherein each of the second outer pin and the second inner pin pins extend along the pivot axis,
      a space between the first and second inner pins,
      wherein the first and second outer pins respectively receive the first and second inner pins therein to movably connect the first and second jaws together, and
      wherein the first outer pin is received against the first curved surface such that the end effector is configured to pivot about the pivot axis.

19. The surgical instrument of claim 18, further comprising a tube extending through the elongate shaft and the space between the first and second inner pins, and wherein the end effector further includes an outlet in fluid communication with the tube.

\* \* \* \* \*